(12) United States Patent
Hoffman et al.

(10) Patent No.: US 12,264,138 B2
(45) Date of Patent: Apr. 1, 2025

(54) PROCESS FOR THE PREPARATION OF MICROBIOCIDAL OXADIAZOLE DERIVATIVES

(71) Applicant: SYNGENTA CROP PROTECTION AG, Basel (CH)

(72) Inventors: Thomas James Hoffman, Stein (CH); Regis Jean Georges Mondiere, Stein (CH); Edouard Godineau, Stein (CH); Wolfgang Stutz, Munchwilen (CH); Sujit Kumar Ghorai, Goa (IN); Anup Jawalekar, Goa (IN)

(73) Assignee: SYNGENTA CROP PROTECTION AG, Basel (CH)

( * ) Notice: Subject to any disclaimer, the term of this patent is extended or adjusted under 35 U.S.C. 154(b) by 758 days.

(21) Appl. No.: 17/594,469

(22) PCT Filed: Apr. 16, 2020

(86) PCT No.: PCT/EP2020/060746
§ 371 (c)(1),
(2) Date: Oct. 18, 2021

(87) PCT Pub. No.: WO2020/212513
PCT Pub. Date: Oct. 22, 2020

(65) Prior Publication Data
US 2022/0194907 A1 Jun. 23, 2022

(30) Foreign Application Priority Data

Apr. 18, 2019 (IN) .............................. 201911015611

(51) Int. Cl.
*C07D 271/06* (2006.01)
(52) U.S. Cl.
CPC .................................. *C07D 271/06* (2013.01)
(58) Field of Classification Search
CPC .................................................... C07D 271/06
USPC ....................................................... 548/131
See application file for complete search history.

(56) References Cited

FOREIGN PATENT DOCUMENTS

| JP | 2013-517278 A | 5/2013 |
|---|---|---|
| JP | 2014-520794 A | 8/2014 |
| WO | 2011/088181 A1 | 7/2011 |
| WO | 2013/008162 A1 | 1/2013 |
| WO | 2017055473 A1 | 4/2017 |
| WO | 2017222951 A1 | 12/2017 |
| WO | 2018177894 A1 | 10/2018 |
| WO | 2018184985 A1 | 10/2018 |

OTHER PUBLICATIONS

Baykov, et al., "The first one-pot ambient-temperature synthesis of 1,2,4-oxadiazoles from amidoximes and carboxylic acid esters", Tetrahedron, 73, pp. 945-951, 2017.
Written Opinion for International Patent Application and International Search Report for International Application No. PCT/EP2020/060746 mailed on Jun. 4, 2020.

*Primary Examiner* — Taofiq A Solola
(74) *Attorney, Agent, or Firm* — BakerHostetler; Toni-Junell Herbert

(57) ABSTRACT

The present invention relates to a process according to Scheme 1 for the preparation of microbiocidal 5-trifluoromethyl-1,2,4-oxadiazole derivatives of formula (I) suitable for use, e.g., as active ingredients, which have microbiocidal activity, in particular, fungicidal activity.

8 Claims, No Drawings

PROCESS FOR THE PREPARATION OF MICROBIOCIDAL OXADIAZOLE DERIVATIVES

CROSS-REFERENCE TO RELATED APPLICATIONS

This application is a 371 National Stage application of International Application No. PCT/EP2020/060746 filed Apr. 16, 2020, which claims priority to IN 201911015611 filed Apr. 18, 2019, the entire contents of these applications are hereby incorporated by reference.

The present invention relates to a process for the preparation of microbiocidal oxadiazole derivatives suitable for use, e.g., as active ingredients, which have microbiocidal activity, in particular, fungicidal activity.

The formation of substituted 3-aryl-5-trifluoromethyl-1,2,4-oxadiazoles is described in WO 2017/055473 by reaction of amidoximes with trifluoroacetic anhydride in the presence of a base in a suitable solvent.

Among drawbacks of this reaction, mention can be made of irreversible hydrolysis via degradation of the 5-trifluoromethyl-1,2,4-oxadiazole group that may result in the formation of by-products, thus lowering chemical yields of the oxadiazole derivatives thereby provided.

According to the present invention, there is provided a process for the preparation of a compound of Formula (I):

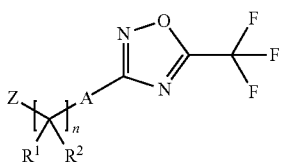

(I)

wherein

A is A-1 or A-2:

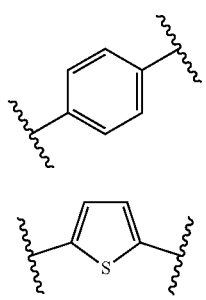

(A-1)

(A-2)

wherein each of A-1 and A-2 is optionally substituted by 1 or 2 substituents independently selected from halogen, $C_{1-4}$alkyl, $C_{1-4}$haloalkyl, $C_{1-4}$alkoxy, and $C_{1-4}$haloalkoxy;

n is 0, 1 or 2;

$R^1$ and $R^2$ are independently selected from hydrogen, halogen, cyano, hydroxy, $C_{1-4}$alkyl, $C_{1-4}$alkoxy, and $C_{1-4}$haloalkyl; or $R^1$ and $R^2$, together with the carbon atom to which they are bonded, form a cyclopropyl ring;

Z is $Z^1$ or $Z^2$:

$Z^1$ is hydrogen, halogen, cyano, —OH, or —SH;

$Z^2$ is $C_{1-4}$alkyl, $C_{1-4}$haloalkyl, $C_{1-4}$alkoxy, $C_{1-4}$haloalkoxy, —COOH, —C(=W)—X, —NR$^3$R$^4$, —NR$^3$—C(=W)—X, —S(=O)$_2$—R$^5$, or —NR$^3$—S(=O)$_2$—R$^5$; or $Z^2$ is $C_{3-8}$cycloalkyl, $C_{3-8}$cycloalkylC$_{1-2}$alkyl, heterocyclyl, heterocyclylC$_{1-2}$alkyl, phenyl, phenylC$_{1-2}$alkyl, heteroaryl, heteroarylC$_{1-2}$alkyl, or heterodiaryl, wherein the heterocyclyl moiety is a 4- to 7-membered non-aromatic ring which comprises 1, 2 or 3 heteroatoms or groups individually selected from O, S, N, NR$^6$, C(=O) and S(=O)$_2$, and the heteroaryl moiety is a 5- or 6-membered monocyclic aromatic ring which comprises 1, 2, 3, or 4 heteroatoms individually selected from N, O and S; wherein any of said cycloalkyl, heterocyclyl, phenyl, heteroaryl or heterodiaryl is optionally substituted by 1 or 2 substituents, which may be the same or different, selected from R$^7$;

W is O or S;

X is halogen, —NR$^3$R$^4$, R$^5$, —NR$^3$—[CR$^8$R$^9$]$_m$—CR$^{10}$(=NR$^5$), —C(=O)—NR$^3$R$^4$, —C(=O)—R$^5$, —C(=N—C$_{1-4}$alkoxy)-R$^5$, or —OR$^{11}$;

$R^3$ and $R^4$ are independently selected from hydrogen, $C_{1-4}$alkyl, $C_{1-4}$haloalkyl, $C_{1-4}$alkoxy, hydroxyC$_{1-4}$alkyl, $C_{1-4}$alkoxyC$_{1-4}$alkyl, $C_{1-4}$haloalkoxy, $C_{1-2}$haloalkoxyC$_{1-4}$alkyl, $C_{2-4}$alkenyl, $C_{2-6}$alkynyl, $C_{3-4}$alkenyloxy, $C_{3-4}$alkynyloxy, $C_{1-4}$alkylcarbonyloxy, N—C$_{1-4}$alkylamino, and N,N-diC$_{1-4}$alkylamino; or $R^3$ and $R^4$ are independently selected from $C_{3-8}$cycloalkyl, $C_{3-8}$cycloalkylC$_{1-2}$alkyl, heterocyclyl, heterocyclylC$_{1-2}$alkyl, phenyl, phenylC$_{1-2}$alkyl, heteroaryl, and heteroarylC$_{1-2}$alkyl, wherein the heterocyclyl moiety is a 4- to 6-membered non-aromatic ring which comprises 1, 2 or 3 heteroatoms or groups individually selected from O, S, N, NR$^6$, C(=O) and S(=O)$_2$, and the heteroaryl moiety is a 5- or 6-membered monocyclic aromatic ring which comprises 1, 2, 3, or 4 heteroatoms individually selected from N, O and S; wherein any of said cycloalkyl, heterocyclyl, phenyl or heteroaryl is optionally substituted by 1 or 2 substituents, which may be the same or different, selected from R$^7$; or $R^3$ and X, together with the nitrogen atom to which R$^3$ is attached, and together with the group —C(=W), form a heterocyclyl, heterocyclylC$_{1-6}$alkyl, heteroaryl, heteroarylC$_{1-2}$alkyl, or heterodiaryl, wherein the heterocyclyl moiety is a 4- to 7-membered non-aromatic ring which comprises 1, 2 or 3 heteroatoms or groups individually selected from O, S, N, NR$^6$, C(=O) and S(=O)$_2$, and the heteroaryl moiety is a 5- or 6-membered monocyclic aromatic ring which comprises 1, 2, 3, or 4 heteroatoms individually selected from N, O and S; wherein any of said heterocyclyl, heteroaryl or heterodiaryl is optionally substituted by 1 or 2 substituents, which may be the same or different, selected from R$^7$;

$R^5$ is $C_{1-4}$alkyl, $C_{1-4}$haloalkyl, hydroxyC$_{1-4}$alkyl, cyanoC$_{1-4}$alkyl, $C_{2-4}$alkenyl, $C_{2-6}$alkynyl, $C_{1-4}$alkoxy, $C_{1-4}$haloalkoxy, or $C_{1-4}$alkoxyC$_{1-4}$alkyl, or $C_{1-2}$haloalkoxyC$_{1-4}$alkyl; or $R^5$ is $C_{3-8}$cycloalkyl, $C_{3-8}$cycloalkylC$_{1-2}$alkyl, heterocyclyl, heterocyclylC$_{1-6}$alkyl, phenyl, phenylC$_{1-2}$alkyl, heteroaryl, heteroarylC$_{1-2}$alkyl, or heterodiaryl, wherein the heterocyclyl moiety is a 4- to 6-membered non-aromatic ring which comprises 1, 2 or 3 heteroatoms or groups individually selected from O, S, N, NR$^6$, C(=O) and S(=O)$_2$, and the heteroaryl moiety is a 5- or 6-membered monocyclic aromatic ring which comprises 1, 2, 3, or 4 heteroatoms individually selected from N, O and S; wherein any of said cycloalkyl, heterocyclyl, phenyl, heteroaryl or heterodiaryl is optionally substituted by 1 or 2 substituents, which may be the same or different, selected from $R^7$;

$R^6$ is hydrogen, $C_{1-4}$alkyl, $C_{1-4}$alkoxy, formyl, $C_{1-4}$alkylcarbonyl, $C_{1-4}$alkoxycarbonyl, N—$C_{1-4}$alkylaminocarbonyl, N,N-di$C_{1-4}$alkylaminocarbonyl, $C_{1-4}$alkylsulfonyl, N—$C_{1-4}$alkylaminosulfonyl, or N,N-di$C_{1-4}$alkylaminosulfonyl;

$R^7$ is halogen, cyano, hydroxy, $C_{1-4}$alkyl, $C_{2-4}$alkenyl, $C_{2-6}$alkynyl, $C_{1-4}$haloalkyl, $C_{2-4}$haloalkenyl, $C_{1-4}$alkoxy, $C_{1-4}$haloalkoxy, $C_{3-4}$alkenyloxy, $C_{3-4}$alkynyloxy, N—$C_{1-4}$alkylamino, N,N-di$C_{1-4}$alkylamino, $C_{1-4}$alkylcarbonyl, $C_{1-4}$alkoxycarbonyl, aminocarbonyl, $C_{1-4}$alkylcarbonylamino$C_{1-4}$alkyl, N—$C_{1-4}$alkylaminocarbonyl, N,N-di$C_{1-4}$alkylaminocarbonyl, $C_{1-4}$alkoxycarbonylamino, N—$C_{1-4}$alkoxyaminocarbonyl, N—$C_{1-4}$alkyl-N—$C_{1-4}$alkoxyaminocarbonyl, $C_{3-8}$cycloalkylaminocarbonyl, N—$C_{3-8}$cycloalkyl $C_{1-2}$alkylaminocarbonyl, N—$C_{1-4}$alkoxy$C_{1-4}$alkylaminocarbonyl, N—$C_{1-4}$alkoxy$C_{1-4}$alkylimino, $C_{1-4}$alkylsulfynyl, or $C_{1-4}$alkylsulfanyl;

m is 0, 1 or 2;

$R^8$ and $R^9$ are independently selected from hydrogen, halogen, cyano, $C_{1-4}$alkyl, and $C_{1-4}$haloalkyl; or $R^8$ and $R^9$, together with the carbon atom to which they are bonded, form a cyclopropyl ring;

$R^{10}$ is hydrogen, $C_{1-6}$alkyl, $C_{2-4}$alkenyl, $C_{2-6}$alkynyl, $C_{1-4}$haloalkyl, $C_{3-8}$cycloalkyl, or phenyl;

$R^{11}$ is $C_{1-8}$alkyl, $C_{1-4}$haloalkyl, hydroxy$C_{1-6}$alkyl, $C_{1-4}$alkoxy$C_{1-6}$alkyl, $C_{1-2}$haloalkoxy$C_{1-4}$alkyl, $C_{1-4}$alkenyl, $C_{2-6}$alkynyl, or $C_{1-4}$alkylcarbonyloxy$C_{1-4}$alkyl;

said process comprising the step of reacting a compound of Formula (II):

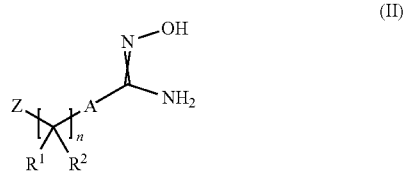

(II)

wherein A, n, $R^1$, $R^2$ and Z are as defined for the compound of Formula (I), with a compound of Formula (III):

(III)

wherein $R^{12}$ is $C_{1-4}$alkyl.

Surprisingly, it has been now found that the process of the invention advantageously provides a mean to produce compounds of Formula (I) at high isolated yields.

The compounds of Formula (I) can be used in the agricultural sector and related fields of use, e.g., as active ingredients for controlling plant pests or on non-living materials for the control of spoilage microorganisms or organisms potentially harmful to man. The novel compounds are distinguished by excellent activity at low rates of application, by being well tolerated by plants and by being environmentally safe. They have very useful curative, preventive and systemic properties and can be used for protecting numerous cultivated plants. The compounds of Formula (I) can be used to inhibit or destroy the pests that occur on plants or parts of plants (fruit, blossoms, leaves, stems, tubers, roots) of different crops of useful plants, while at the same time protecting also those parts of the plants that grow later, e.g., from phytopathogenic microorganisms.

The compounds of Formula (I) have, for practical purposes, a very advantageous level of biological activity for protecting plants against diseases that are caused by fungi. Thus, the compound of Formula (I) is particularly suitable for use as a fungicide. The term "fungicide" as used herein means a compound that controls, modifies, or prevents the growth of fungi. According to this particular aspect of the invention, the use may exclude methods for the treatment of the human or animal body by surgery or therapy.

The compounds of Formula (I) are for example, effective against fungi and fungal vectors of disease as well as phytopathogenic bacteria and viruses.

As used herein, the term "halogen" or "halo" refers to fluorine (fluoro), chlorine (chloro), bromine (bromo) or iodine (iodo), preferably fluorine, chlorine or bromine.

As used herein, cyano means a —CN group.

As used herein, amino means an —$NH_2$ group.

As used herein, hydroxy means an —OH group.

As used herein, the term "$C_{1-6}$alkyl" refers to a straight or branched hydrocarbon chain radical consisting solely of carbon and hydrogen atoms, containing no unsaturation, having from one to six carbon atoms, and which is attached to the rest of the molecule by a single bond. The terms "$C_{1-4}$alkyl" and "$C_{1-2}$alkyl" are to be construed accordingly. A "$C_{1-6}$alkylene", $C_{1-4}$alkylene" or "$C_{1-2}$alkylene" group refers to the corresponding definition of $C_{1-6}$alkyl, $C_{1-4}$alkyl or $C_{1-2}$alkyl, respectively, except that such radical is attached to the rest of the molecule by two single bonds. Examples of $C_{1-6}$alkyl include, but are not limited to, methyl, ethyl, iso-propyl, n-propyl and tert-butyl.

As used herein, the term "$C_{1-4}$alkoxy" refers to a radical of the formula —$OR_a$ where $R_a$ is a $C_{1-4}$alkyl radical as generally defined above. Examples of $C_{1-4}$alkoxy include, but are not limited to, methoxy, ethoxy and propoxy.

As used herein, the term "$C_{1-4}$alkoxy$C_{1-4}$alkyl" refers to radical of the formula $R_b$—O—$R_a$— where $R_b$ is a $C_{1-4}$alkyl radical as generally defined above, and $R_a$ is a $C_{1-4}$alkylene radical as generally defined above.

As used herein, the term "$C_{1-4}$alkylsulfanyl" refers to a radical of the formula —$SR_a$ where $R_a$ is a $C_{1-4}$alkyl radical as generally defined above.

As used herein, the term "$C_{1-4}$alkylsulfynyl" refers to a radical of the formula —S(—O)$R_a$ where $R_a$ is a $C_{1-4}$alkyl radical as generally defined above.

As used herein, the term "$C_{1-4}$alkylsulfonyl" refers to a radical of the formula —$S(O)_2R_a$ where $R_a$ is a $C_{1-4}$alkyl radical as generally defined above.

As used herein, the term "$C_{2-4}$alkenyl" refers to a straight or branched hydrocarbon chain radical group consisting solely of carbon and hydrogen atoms, containing at least one double bond that can be of either the (E)- or (Z)-configuration, having from two to four carbon atoms, which is attached to the rest of the molecule by a single bond. The term "$C_{3-4}$alkenyl" is to be construed accordingly. Examples of $C_{2-4}$alkenyl include, but are not limited to, ethenyl and prop-1-enyl.

As used herein, the term "$C_{2-6}$alkynyl" refers to a straight or branched hydrocarbon chain radical group consisting solely of carbon and hydrogen atoms, containing at least one triple bond, having from two to four carbon atoms, and which is attached to the rest of the molecule by a single bond. The term "$C_{3-6}$alkynyl" is to be construed accordingly. Examples of $C_{3-6}$alkynyl include, but are not limited to, ethynyl, prop-1-ynyl, propargyl (prop-2-ynyl), but-1-ynyl and 3-methyl-but-1-ynyl.

As used herein, the term "$C_{3-4}$alkenyloxy" refers to a radical of the formula —OR$_a$ where R$_a$ is a $C_{3-4}$alkenyl radical as generally defined above.

As used herein, the term "$C_{3-4}$alkynyloxy" refers to a radical of the formula —OR$_a$ where R$_a$ is a $C_{3-4}$alkynyl radical as generally defined above.

As used herein, the term "$C_{1-4}$alkoxycarbonyl" refers to a radical of the formula —C(O)OR$_a$ where R$_a$ is a $C_1$—$C_4$alkyl radical as generally defined above.

As used herein, the term "$C_{1-4}$alkylcarbonyl" refers to a radical of the formula —C(O)R$_a$ where R$_a$ is a $C_{1-4}$alkyl radical as generally defined above.

As used herein, the term "formyl" refers to a radical of the formula —C(O)H.

As used herein, the term "$C_{1-4}$alkylcarbonyloxy" refers to a radical of the formula —OC(O)R$_a$ where R$_a$ is a $C_{1-4}$alkyl radical as generally defined above.

As used herein, the term "$C_{1-4}$haloalkoxy" refers to a $C_{1-4}$alkoxy group as defined above substituted by one or more of the same or different halogen atoms. Examples of $C_{1-4}$haloalkoxy include, but are not limited to, fluoromethoxy, difluoromethoxy, trifluoromethoxy, fluoroethoxy and trifluoroethoxy.

As used herein, the term "$C_{1-2}$haloalkoxy$C_{1-4}$alkyl" refers to a $C_{1-4}$alkyl radical as defined above substituted by a $C_{1-2}$haloalkoxy group as defined above.

As used herein, the term "$C_{1-4}$haloalkyl" refers to a $C_{1-4}$alkyl radical as generally defined above substituted by one or more of the same or different halogen atoms. Examples of $C_{1-4}$haloalkyl include, but are not limited to fluoromethyl, difluoromethyl, trifluoromethyl, fluoroethyl and trifluoroethyl.

As used herein, the term "$C_{2-4}$haloalkenyl" refers to a $C_{2-4}$alkenyl radical as generally defined above substituted by one or more of the same or different halogen atoms.

As used herein, the term "$C_{3-8}$cycloalkyl" refers to a stable, monocyclic or bi-cyclic ring radical which is saturated or partially unsaturated and contains 3 to 8 carbon atoms. $C_{3-6}$cycloalkyl is to be construed accordingly. Examples of $C_{3-8}$cycloalkyl include, but are not limited to, cyclopropyl, cyclobutyl, cyclopentyl and cyclohexyl.

As used herein, the term "$C_{3-8}$cycloalkyl$C_{1-2}$alkyl" refers to a $C_{3-8}$cycloalkyl ring as defined above attached to the rest of the molecule by a $C_{1-2}$alkylene radical as defined above. The terms "$C_{3-6}$cycloalkyl$C_{1-2}$alkyl" and "$C_{3-4}$cycloalkyl$C_{1-2}$alkyl" are to be construed accordingly. Examples of $C_{3-8}$cycloalkyl$C_{1-2}$alkyl include, but are not limited to cyclopropyl-methyl, cyclobutyl-ethyl, and cyclopentyl-propyl.

As used herein, the term "$C_{3-8}$cycloalkylaminocarbonyl" refers to a radical of the formula —C(O)NR$_a$ where R$_a$ is a $C_{3-8}$cycloalkyl radical as generally defined above.

As used herein, the term "N—$C_{3-8}$cycloalkyl$C_{1-2}$alkylaminocarbonyl" refers to a radical of the formula —C(O)NR$_a$ where R$_a$ is a $C_{3-8}$cycloalkyl$C_{1-2}$alkylene radical as defined above.

As used herein, the term "$C_{1-4}$alkoxycarbonylamino" refers to a radical of the formula —NH—C(O)—O—R$_a$ where R$_a$ is a $C_{1-4}$alkyl radical as defined above.

As used herein, the term "$C_{1-4}$alkoxycarbonylamino $C_{1-4}$alkyl" refers to a radical of the formula —R$_a$C(O)NHR$_b$ where R$_a$ is a $C_{1-4}$alkoxy radical as defined above and R$_b$ is a $C_{1-4}$alkylene radical as defined above.

As used herein, the term "$C_{1-4}$alkylcarbonyloxy" refers to a radical of the formula —OC(O)R$_a$ where R$_a$ is a $C_{1-4}$alkyl as generally defined above.

As used herein, the term "$C_{1-4}$alkylcarbonyloxy$C_{1-4}$alkyl" refers to a radical of the formula —R$_a$OC(O)R$_b$ where R$_a$ is a $C_{1-4}$alkylene radical as generally defined above and R$_b$ is a $C_{1-4}$alkyl as generally defined above.

As used herein, oxo means an =O group, e.g., a ketonyl (—C(O)—), sulfinyl (—S(O)—) or sulfonyl (—S(O)$_2$—) oxygen.

As used herein, aminocarbonyl means an —C(O)NH$_2$ radical.

As used herein, the term "N—$C_{1-4}$alkylamino" refers to a radical of the formula —NH—R$_a$ where R$_a$ is a $C_{1-4}$alkyl radical as defined above.

As used herein, the term "N,N-di$C_{1-4}$alkylamino" refers to a radical of the formula —N(R$_a$)R$_a$ where each R$_a$ is a $C_{1-4}$alkyl radical, which may be the same or different, as defined above.

As used herein, the term "N,N-di$C_{1-4}$alkylaminocarbonyl" refers to a radical of the formula —C(O)NR$_a$)R$_a$) where each R$_a$ is a $C_{1-4}$alkyl radical, which may be the same or different, as generally defined above.

As used herein, the term "N—$C_{1-4}$alkylaminocarbonyl" refers to a radical of the formula —C(O)NHR$_a$ where R$_a$ is a $C_{1-4}$alkyl radical as generally defined above.

As used herein, the term "N—$C_{1-4}$alkoxy$C_{1-4}$alkylaminocarbonyl" refers to a radical of the formula —C(O) NHR$_a$OR$_b$ where R$_a$ is a $C_{1-4}$alkylene radical as generally defined above, and R$_b$ is a $C_{1-4}$alkyl radical as generally defined above.

As used herein, the term "N—$C_{1-4}$alkoxyaminocarbonyl, refers to a radical of the formula —C(O)NHOR$_a$ where R$_a$ is a a $C_{1-4}$alkyl radical as generally defined above.

As used herein, the term "N—$C_{1-4}$alkyl-N—$C_{1-4}$alkoxyaminocarbonyl, refers to a radical of the formula —C(O)N(R$_a$)OR$_b$ where R$_a$ is a $C_{1-4}$alkyl radical as generally defined above, and R$_b$ is a $C_{1-4}$alkyl radical (same or different to R$_a$) as generally defined above.

As used herein, the term "$C_{1-4}$alkylcarbonylamino $C_{1-4}$alkyl" refers to a radical of the formula R$_b$—C(O) NHR$_a$— where R$_b$ is a $C_{1-4}$alkyl radical, and R$_a$ is a $C_{1-4}$alkylene radical as generally defined above.

As used herein, the term "N—$C_{1-4}$alkoxy$C_{1-4}$alkylimino" refers to a radical of the formula —C(N)OR$_a$ where R$_a$ is a $C_{1-4}$alkyl radical as generally defined above.

As used herein, the term "phenyl$C_{1-2}$alkyl" refers to a phenyl ring attached to the rest of the molecule by a $C_{1-2}$alkylene radical as defined above.

As used herein, the term "aryl" refers to an aromatic ring system consisting solely of carbon and hydrogen atoms which may be mono-, bi- or tricyclic. Examples of such ring systems include phenyl, naphthalenyl, anthracenyl, indenyl or phenanthrenyl.

As used herein, the term "heteroaryl" (unless defined otherwise) refers to a 5- or 6-membered aromatic monocyclic ring radical which comprises 1, 2, 3 or 4 heteroatoms individually selected from nitrogen, oxygen and sulfur. The heteroaryl radical may be bonded via a carbon atom or a heteroatom. Examples of heteroaryl include, but are not limited to, furyl, pyrrolyl, thienyl, pyrazolyl, imidazolyl, thiazolyl, isothiazolyl, oxazolyl, isoxazolyl, triazolyl, tetrazolyl, pyrazinyl, pyridazinyl, pyrimidyl or pyridyl.

As used herein, the term "heteroaryl$C_{1-4}$alkyl" refers to a heteroaryl ring attached to the rest of the molecule by a $C_{1-2}$alkylene radical as defined above.

As used herein, the term "heterodiaryl" (unless defined otherwise) refers to a stable 9- or 10-membered bicyclic aromatic ring system which comprises 1, 2, 3 or 4 heteroatoms individually selected from nitrogen, oxygen and sulfur. The heterodiaryl radical may be bonded to the rest of the molecule via a carbon atom or heteroatom. Examples of heterodiaryl include, but are not limited to, indolyl, indazolyl, benzimidazolyl, pyrrolopyridinyl or triazolopyridinyl.

As used herein, the term "heterocyclyl" or "heterocyclic" (unless defined otherwise) refers to a stable 4-, 5-, 6- or 7-membered non-aromatic monocyclic ring radical which comprises 1, 2, or 3, heteroatoms individually selected from nitrogen, oxygen and sulfur or groups individually selected from $NR^6$, $C(=O)$ and $S(=O)_2$, wherein $R^6$ is as defined above. The heterocyclyl radical may be bonded to the rest of the molecule via a carbon atom or heteroatom. Examples of heterocyclyl include, but are not limited to, azetidinyl, oxetanyl, pyrrolinyl, pyrrolidyl, thietanyl, tetrahydrofuranyl, tetrahydrothienyl, tetrahydrothiopyranyl, piperidyl, piperazinyl, tetrahydropyranyl, morpholinyl or perhydroazepinyl.

As used herein, the term "heterocyclyl$C_{1-6}$alkyl" refers to a heterocyclyl ring attached to the rest of the molecule by a $C_{1-6}$alkylene radical as defined above. The terms "heterocyclyl$C_{1-4}$alkyl" and "heterocyclyl$C_{1-2}$alkyl" are to be construed accordingly.

The compounds of Formula (I) can be made by the process of the invention as shown in the following Schemes 1 to 13, in which, unless otherwise stated, the definition of each variable is as defined above for a compound of Formula (I).

The designations of n, m, A-1, A-2, $R^1$, $R^2$, $R^3$, $R^4$, $R^5$, $R^6$, $R^7$, $R^8$, $R^9$, $R^{19}$, $R^{11}$, $Z(Z^1, Z^2)$, W and X, with reference to the compounds of Formula (I) obtained by the process of the present invention, apply generally to the compounds of any of Formulae (I-A), (I-B), or (I-a), as well as to the compounds of Formula (II), including the compounds of any of Formulae (II-A), (II-1), (II-2), (II-3) or (II-4), or each of the compounds of Formulae (IV), (V), (VI), (VII), (VIII), (IX) or (X), including the compounds of any of Formulae (VII-A) or (VII-a).

The compound of Formula (I) is prepared according to the process of the invention, said process comprising the step of reacting a compound of Formula (II) with a compound of Formula (III). This reaction is shown in Scheme 1.

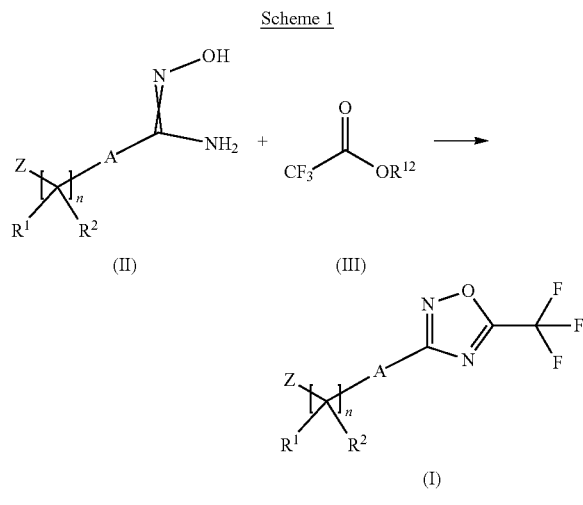

Scheme 1

For the purpose of the present invention, the compound of Formula (II) is used in the process of the invention in any of its tautomeric forms with different (E)/(Z)-configurations.

Examples of compounds of Formula (III) suitable for use in the process of the invention include those wherein $R^{12}$ is selected from methyl, ethyl, n-propyl, iso-propyl, n-butyl, sec-butyl, tert-butyl, and iso-butyl. Preferably, $R^{12}$ in the compound of Formula (III) is methyl or ethyl. The compound of Formula (III) is more preferably methyl 2,2,2-trifluoroacetate or ethyl 2,2,2-trifluoroacetate.

In an embodiment of the process of the invention, the compound of Formula (I) is advantageously prepared from a compound of Formula (II) via reaction with an amount of from 1.0 to 2.0 equivalents of a compound of Formula (III).

In a preferred embodiment of the invention, the process of the invention is carried out in the presence of at least one base.

According to one embodiment, the process of the invention is carried out in the presence of at least one base and, optionally, at least one solvent.

Examples of suitable bases include inorganic bases and organic bases. Preferred bases are selected from the group consisting of tertiary amines, substituted or non-substituted pyridine, bycyclic amines and mixtures thereof, NaH, alkali metal $C_{1-6}$alkoxylates and alkaline earth metal $C_{1-6}$alkoxylates such as, for instance, sodium methoxide, sodium ethoxide, sodium tert-butoxide, potassium tert-butoxide, potassium pentoxide, potassium carbonate ($K_2CO_3$) and sodium carbonate ($Na_2CO_3$).

More preferably, the process of the invention is carried out in the presence of at least one base selected from the group consisting of alkali metal $C_{1-6}$alkoxylates and alkaline earth metal $C_{1-6}$alkoxylates. Even more preferably, the process of the invention is carried out in the presence of sodium tert-butoxide or potassium tert-butoxide.

As used herein, the term "alkali metal" refers to the elements in group 1 of the Periodic Table, preferably to lithium (Li), sodium (Na), or potassium (K).

As used herein, the term "alkaline earth metal" refers to the elements in group 2 of the Periodic Table, preferably to magnesium (Mg), or calcium (Ca).

Examples of suitable solvents include, for instance, methanol, ethanol, tert-butanol, tetrahydrofuran, 2-methyltetrahydrofuran, N,N-dimethylformamide, dimethylsulfoxide, pyridine, pyrrolidine, N-methyl-2-pyrrolidone, toluene, and dioxane.

Typical reaction concentrations are usually in the range from 0.5 M to 2.0 M. Very good results have been obtained when the process of the invention is carried out at a concentration of 0.7 M.

The process of the invention is usually carried out at a temperature from 0° C. to 60° C., preferably from 0° C. to 40° C., more preferably from 0° C. to 25° C. Very good results have been obtained when the process of the invention is carried out at a temperature from 0° C. to 25° C.

The process of the invention is usually carried out at a pressure from 1 atm to 5 atm.

Typical reaction times are usually in the range from 1 to 16 hours. Very good results have been obtained when the process of the invention is carried out at reaction times of 1 to 2 hours.

A reaction mixture is generally obtained from the process of the invention, said process comprising the step of reacting a compound of Formula (II) with a compound of Formula (III), preferably in the presence of at least one base and, optionally, at least one solvent.

The process of the invention typically further comprises the step of isolating the compound of Formula (I) using an aqueous medium. The compound of Formula (I) is advantageously isolated from the reaction mixture using an aqueous medium, typically by an extractive work-up.

In a preferred embodiment of the process of the invention, the aqueous medium is an aqueous acidic medium. The aqueous acidic medium is generally prepared by addition of one or more acids to the aqueous medium. Preferably, the process of the invention further comprises the step of isolating the compound of Formula (I) using an aqueous acidic medium.

It has been found that an aqueous acidic medium during reaction work-up may provide the most suitable medium for purification of compounds of Formula (I). In particular, it has been surprisingly found that an improvement in the isolated yield can be obtained by adding an aqueous acidic medium to the reaction mixture.

The aqueous acidic medium typically comprises an acid selected from the group consisting of acetic acid, citric acid, sulfuric acid, chloridric acid (HCl), HCl/water, HCl/dioxane. Preferably, the aqueous acidic medium comprises citric acid.

The aqueous acidic medium preferably has a pH of from 2.0 to 6.0, more preferably of from 4.9 to 5.9.

The present invention also relates to intermediates of any of Formulae (II-1), (II-2), (II-3) and (II-4) which are typically formed in the process of the invention from the step of reacting a compound of Formula (II) with a compound of Formula (III). The intermediates so obtained may be characterized by any suitable analytical techniques such as NMR and IR spectroscopy.

It is understood that, when in an aqueous medium, the compound of Formula (I) according to the invention may be present in a reversible equilibrium with the corresponding hydrated intermediate of Formula (II-4). This dynamic equilibrium may be important for the biological activity of the compounds of Formula (I). This reaction is shown in Scheme 2.

It is also understood that using an aqueous acidic medium it is advantageously possible avoiding both the reverse hydration equilibrium affording an intermediate of Formula (II-4) and hydrosis via cleavage of the trifluoracetyl group that results in decomposition of a compound of Formula (I) to a compound of Formula (II).

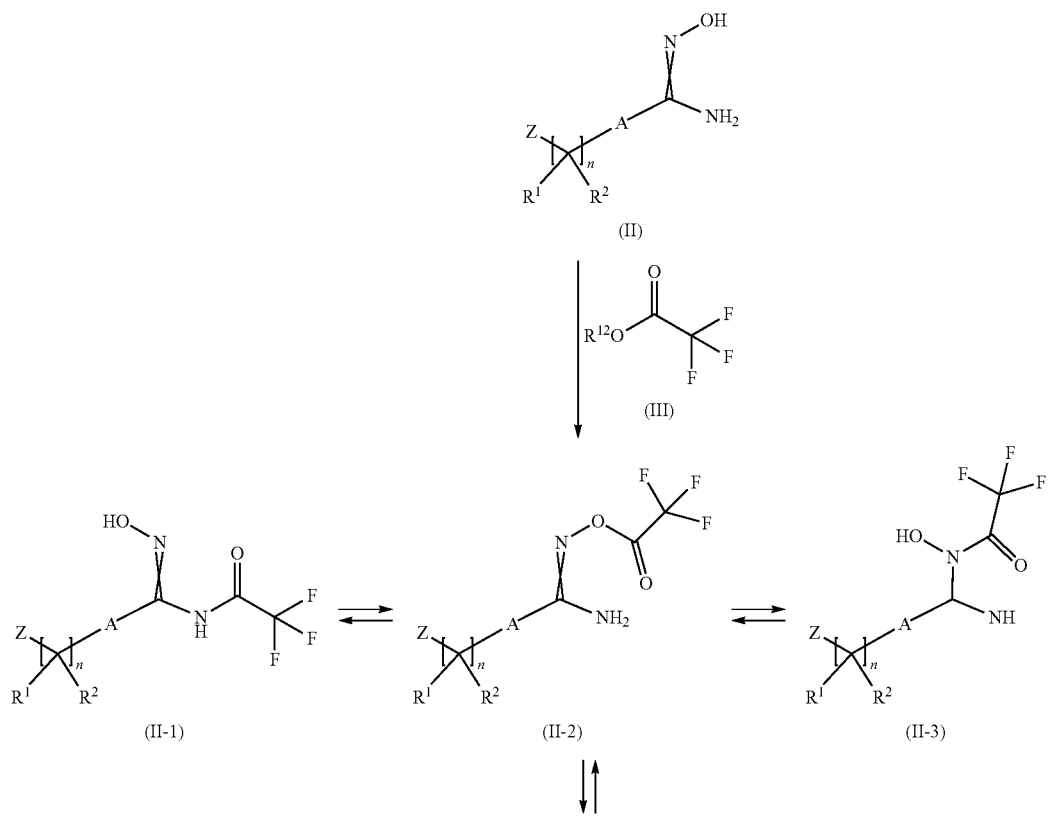

Scheme 2

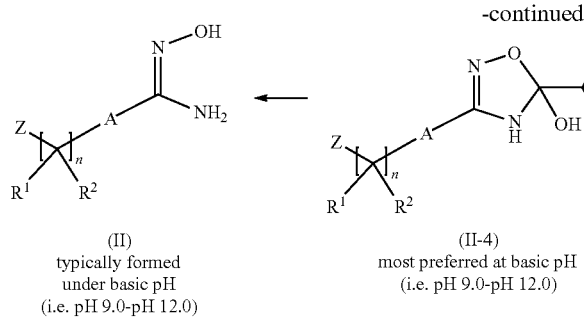
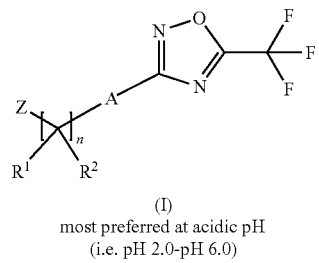

(II) typically formed under basic pH (i.e. pH 9.0-pH 12.0)

(II-4) most preferred at basic pH (i.e. pH 9.0-pH 12.0)

(I) most preferred at acidic pH (i.e. pH 2.0-pH 6.0)

The following list provides definitions, including preferred definitions, for substituents n, m, A-1, A-2, $R^1$, $R^2$, $R^3$, $R^4$, $R^5$, $R^6$, $R^7$, $R^8$, $R^9$, $R^{10}$, $R^{11}$, Z($Z^1$, $Z^2$), W and X with reference to the compounds of Formula (I). For any of these substituents, any of the definitions given below may be combined with any definitions of any other substituent given below or elsewhere in the present invention.

Preferably, n in the compound of Formula (I) is 0 or 1.

In a preferred embodiment, the present invention relates to a process for the preparation of a compound of Formula (I), wherein Z is $Z^2$, hereinafter referred to as compound of Formula (I-A).

Table 1.1: This table discloses 206 specific compounds of Formula (I-1)

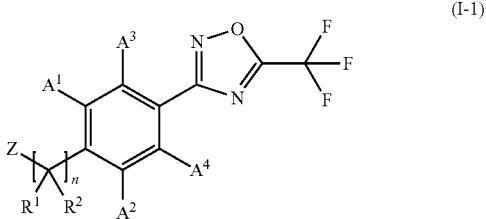

(I-1)

wherein n is 1, $A^1$, $A^2$, $A^3$, $A^4$, $R^1$ and $R^2$ are hydrogen, and Z is as defined below in Table 1.

TABLE 1

| Compound no. | Z |
|---|---|
| 1.001 | (3-pyridyl)triazol-1-yl |
| 1.002 | (4-chlorophenyl)tetrazol-2-yl |
| 1.003 | (4-methoxyphenyl)triazol-1-yl |
| 1.004 | [(5-chloro-3-methoxy-2-pyridyl)-oxymethyl]triazol-1-yl |
| 1.005 | [1-(2,6-diethylphenyl)-5-methyl-pyrazol-4-yl]triazol-1-yl |
| 1.006 | [1-triazol-4-yl]methyl acetate |
| 1.007 | 1,2,4-triazol-1-yl |
| 1.008 | 1,2,4-triazol-1-yl-3-carbonitrile |
| 1.009 | 1,2,4-triazol-2-yl-3-amine |
| 1.010 | 1,2,4-triazol-2-yl-3-carbonitrile |
| 1.011 | 1,2,4-triazol-4-yl |
| 1.012 | 1,2,4-triazol-4yl-3-amine |
| 1.013 | 1-[pyrrol-2-yl]ethanone |
| 1.014 | 1H-triazol-4-ylmethyl acetate |
| 1.015 | 2-(4-pyridyl)benzimidazol-1-yl |
| 1.016 | 2-(trifluoromethyl)benzimidazol-1-yl |
| 1.017 | 2,4-dimethylimidazol-1-yl |
| 1.018 | 2-bromoimidazol-1-yl |
| 1.019 | 2-ethylbenzimidazol-1-yl |
| 1.020 | 2-isopropylimidazol-1-yl |
| 1.021 | 2-methylimidazol-1-yl |
| 1.022 | 2-phenylimidazol-1-yl |

TABLE 1-continued

| Compound no. | Z |
|---|---|
| 1.023 | 3-(cyano)-1,2,4-triazol-1-yl |
| 1.024 | 3-(trifluoromethyl)-1,2,4-triazol-1-yi |
| 1.025 | 3-(trifluoromethyl)pyrazol-1-yl |
| 1.026 | 3,4,5-trimethylpyrazol-1-yl |
| 1.027 | 3,5-bis(difluoromethyl)pyrazol-1-yl |
| 1.028 | 3,5-bis(trifluoromethyl)pyrazol-1-yl |
| 1.029 | 3,5-dimethylpyrazol-1-yl |
| 1.030 | 3,5-ethylpyrazol-1-yl |
| 1.031 | 3-[4-[[4-(1-ethyl-3-methyl-pyrazol-4-yl)triazol-1-yl |
| 1.032 | 3-[4-[[4-(1-ethyl-5-methyl-pyrazol-4-yl)triazol-1-yl |
| 1.033 | 3-benzylsulfanyl-1,2,4-triazol-1-yl |
| 1.034 | 3-benzylsulfanyl-1,2,4-triazol-4-yl |
| 1.035 | 3-bromo-5-methoxy-1,2,4-triazol-1-yl |
| 1.036 | 3-chloropyrazol-1-yl |
| 1.037 | 3-ethylsulfanyl-1,2,4-triazol-1-yl |
| 1.038 | 3-propylsulfanyl-1,2,4-triazol-1-yl |
| 1.039 | 4-(1-ethyl-3-methylpyrazol-4-yl)triazol-1-yl |
| 1.040 | 4-(1-ethyl-5-methylpyrazol-4-yl)triazol-1-yl |
| 1.041 | 4-(2-pyridyl)triazol-1-yl |
| 1.042 | 4-(3-methylimidazol-4-yl)triazol-1-yl |
| 1.043 | 4-(3-methylimidazol-4-yl)triazol-1-yl |
| 1.044 | 4-(3-pyridyl)triazol-1-yl |
| 1.045 | 4-(3-thienyl)triazol-1-yl |
| 1.046 | 4-(4-fluorophenyl)triazol-1-yl |
| 1.047 | 4-(4-methoxyphenyl)triazol-1-yl |
| 1.048 | 4-(ethoxymethyl)triazol-1-yl |
| 1.049 | 4-(phenoxymethyl)triazol-1-yl |
| 1.050 | 4-(p-tolyl)triazol-1-yl |
| 1.051 | 4-(triazolo[4,5-b]pyridin-1-yl |
| 1.052 | 4-(triazolo[4,5-b]pyridin-3-yl |
| 1.053 | 4-(triazolo[4,5-b]pyridin-4-yl |
| 1.054 | 4-(trifluoromethyl)imidazol-1-yl |
| 1.055 | 4-(trifluoromethyl)pyrazol-1-yl |
| 1.056 | 4,5-dichloroimidazol-1-yl |
| 1.057 | 4-[(5-chloro-3-methoxy-2-pyridyl)oxymethyl]triazol-1-yl |
| 1.058 | 4-bromo-2-methyl-imidazol-1-yl |
| 1.059 | 4-bromoimidazol-1-yl |
| 1.060 | 4-bromopyrazol-1-yl |
| 1.061 | 4-chlorobenzimidazol-1-yl |
| 1.062 | 4-chlorophenyl)imidazol-1-yl |
| 1.063 | 4-chloropyrazol-1-yl |
| 1.064 | 4-cyclopentyltriazol-1-yl |
| 1.065 | 4-cyclopropyltriazol-1-yl |
| 1.066 | 4-fluorophenyl)imidazol-1-yl |
| 1.067 | 4-iodoimidazol-1-yl |
| 1.068 | 4-iodopyrazol-1-yl |
| 1.069 | 4-isobutyltriazol-1-yl |
| 1.070 | 4-methylimidazol-1-yl |
| 1.071 | 4-phenylimidazol-1-yl |
| 1.072 | 4-phenyltriazol-1-yl |
| 1.073 | 4-pyrazol-1-yl |
| 1.074 | 4-tert-butyltriazol-1-yl |
| 1.075 | 4-trimethylsilyltriazol-1-yl |
| 1.076 | 5-(cyano)-1,2,4-triazol-1-yl |
| 1.077 | 5-(trifluoromethyl)-1,2,4-triazol-1-yl |
| 1.078 | 5,5-dimethyl-4H-oxazol-2-yl |
| 1.079 | 5,6-dichlorobenzotriazol-1-yl |
| 1.080 | 5,6-dihydrocyclopenta[c]pyrrol-1-yl-4-one |

TABLE 1-continued

| Compound no. | Z |
|---|---|
| 1.081 | 5-bromo-3-methoxy-1,2,4-triazol-1-yl |
| 1.082 | 5-chloro-3-(trifluoromethyl)-1,2,4-triazol-1-yl |
| 1.083 | 5-chlorobenzotriazol-2-yl |
| 1.084 | 5-ethylsulfanyl-1,2,4-triazol-1-yl |
| 1.085 | 5-iodoimidazol-1-yl |
| 1.086 | 5-methoxy-1,2,4-triazol-1-yl-3-amine |
| 1.087 | 5-methoxy-1,2,4-triazol-2-yl-3-amine |
| 1.088 | 5-methoxylndol-1-yl |
| 1.089 | 5-methyl-3-(trifluoromethyl)pyrazol-1-yl |
| 1.090 | 5-methylindol-1-yl |
| 1.091 | 5-methyl-pyrazol-1-yl-3-carbonitrile |
| 1.092 | 5-methyl-pyrazol-1-yl-3-ol |
| 1.093 | 5-phenylimidazol-1-yl |
| 1.094 | 5-phenyltriazol-1-yl |
| 1.095 | 5-propylsulfanyl-1,2,4-triazol-1-yl |
| 1.096 | 6-chloro-5-fluoro-benzimidazol-1-yl |
| 1.097 | 6-chloroindol-1-yl |
| 1.098 | 6-fluoroindol-1-yl |
| 1.099 | 6-methoxypyrid-3-yl |
| 1.100 | 7-chlorobenzimidazol-1-yl |
| 1.101 | benzotriazol-1-yl |
| 1.102 | benzotriazol-2-yl |
| 1.103 | dimethyl imidazol-1-yl-4,5-dicarboxylate |
| 1.104 | ethyl 2-[1-pyrazol-3-yl]pyridine-3-carboxylate |
| 1.105 | ethyl 3-(difluoromethyl)-pyrazol-1-yl-4-carboxylate |
| 1.106 | ethyl 3-(trifluoromethyl)-pyrazol-1-yl-4-carboxylate |
| 1.107 | ethyl 4-phenyl-pyrazol-1-yl-3-carboxylate |
| 1.108 | ethyl 5-(difluoromethyl)-pyrazol-1-yl-4-carboxylate |
| 1.109 | ethyl 5-cyclopropyl-pyrazol-1-yl-3-carboxylate |
| 1.110 | ethyl 5-cyclopropyl-pyrazol-2-yl-3-carboxylate |
| 1.111 | ethyl 5-methyl-imidazol-3-yl-4-carboxylate |
| 1.112 | ethyl 5-propyl-imidazol-3-yl-4-carboxylate |
| 1.113 | ethyl 5-propyl-imidazol-4-yl-4-carboxylate |
| 1.114 | ethyl pyrazl-1-yl-4-carboxylate |
| 1.115 | imidazo-1-yl-carbonitrile |
| 1.116 | imidazol-1-yl |
| 1.117 | imidazol-1-yl-4,5-dicarbonitrile |
| 1.118 | imidazol-1-yl-4-carbaldehyde |
| 1.119 | imidazol-3-yl-4-carbaldehyde |
| 1.120 | indazol-1-yl |
| 1.121 | indazol-1-yl-3-carbonitrile |
| 1.122 | indazol-2-yl |
| 1.123 | methyl 1,2,4-triazol-1-yl-3-carboxylate |
| 1.124 | methyl 1,2,4-triazol-2-yl-3-carboxylate |
| 1.125 | methyl 1,2,4-triazol-4-yl-3-carboxylate |
| 1.126 | methyl 1H-1,2,4-triazole-3-carboxylate |
| 1.127 | methyl 1H-1,2,4-triazole-5-carboxylate |
| 1.128 | methyl 2-methyl-pyrrole-1-yl-3-carboxylate |
| 1.129 | methyl 3-(methoxymethyl)-pyrazol-1-yl-4-carboxylate |
| 1.130 | methyl 3-cyclopropyl-pyrazol-4-yl-4-carboxylate |
| 1.131 | methyl 3-imidazol-3-yl-4-carboxylate |
| 1.132 | methyl 5-(methoxymethyl)-pyrazol-1-yl-4-carboxylate |
| 1.133 | methyl 5-cyclopropyl-pyrazol-1-yl-4-carboxylate" |
| 1.134 | methyl imidazol-1-yl-4-carboxylate |
| 1.135 | methyl indazol-1-yl-4-carboxylate |
| 1.136 | methyl indazol-2-yl-4-carboxylate |
| 1.137 | methyl indol-1-yl-4-carboxylate |
| 1.138 | methyl pyrazol-yl-e-4-carboxylate |
| 1.139 | N-(2-methoxyethyl) pyrazol-1-yl-4-carboxamide |
| 1.140 | N-(cyclopropylmethyl) pyrazol-4-yl-4-carboxamide |
| 1.141 | N,N-dimethyl-1,2,4-triazol-1-yl-3-amine |
| 1.142 | N,N-dimethyl-pyrazol-1-yl-4-carboxamide |
| 1.143 | N-[1-methyl-1-(1H-triazol-4-yl)ethyl]benzamide |
| 1.144 | N-2-[1-[imidazol-4-yl]ethyl] acetamide |
| 1.145 | N-cyclopropyl-pyrazol-1-yl-4-carboxamide |
| 1.146 | N-methyl-pyrazol-1-yl-4-carboxamide |
| 1.147 | N-prop-2-ynyl pyrazol-1-yl-4-carboxamide |
| 1.148 | pyrazol-1-yl |
| 1.149 | pyrazol-1-yl-3-carbaldehyde |
| 1.150 | pyrazol-1-yl-4-carbonitrile |
| 1.151 | pyrazol-1-yl-4-carboxylic acid |
| 1.152 | pyrrol-1-yl-2-carbaldehyde |
| 1.153 | pyrrol-1-yl-3-carbonitrile |
| 1.154 | pyrrolo[2,3-b]pyridin-1-yl |
| 1.155 | pyrrolo[3,2-b]pyridin-1-yl-2-carbonitrile |
| 1.156 | pyrrolo[3,2-b]pyridin-4-yl-2-carbonitrile |
| 1.157 | tert-butyl N-(1H-triazol-4-ylmethyl)carbamate |
| 1.158 | triazol-1-yl |
| 1.159 | triazol-2-yl |
| 1.160 | triazolo[4,5-b]pyridin-2-yl |
| 1.161 | trimethyl-triazol-4-yl silane |
| 1.162 | 1,2,4-triazol-1-yl-3-carbonitrile |
| 1.163 | N,N-diethyl-pyrazol-1-yl-4-carboxamide |
| 1.164 | N-methoxy-N-methyl-pyrazol-1-yl-4-carboxamide |
| 1.165 | morpholino-[pyrazol-4-yl]methanone |
| 1.166 | tert-butyl pyrazol-1-yl-4-carboxylate |
| 1.167 | isopropyl pyrazol-1-yl-4-carboxylate |
| 1.168 | propyl pyrazol-1-yl-4-carboxylate |
| 1.169 | 2-(dimethylamino)ethyl pyrazol-1-yl-4-carboxylate |
| 1.170 | N-methoxy-pyrazol-1-yl-4-carboxamide |
| 1.171 | N-ethyl-pyrazol-1-yl-4-carboxamide |
| 1.172 | pyrazol-1-yl-4-carboxamide |
| 1.173 | methyl triazol-1-yl-4-carboxylate |
| 1.174 | triazol-1-yl-4-carboxylic acid |
| 1.175 | N-methyl-triazol-1-yl-4-carboxamide |
| 1.176 | pyrazol-1-yl-4-carbaldehyde |
| 1.177 | N-ethyl-1-triazol-1-yl-4-carboxamide |
| 1.178 | N-methoxy-N-methyl-triazol-1-yl-4-carboxamide |
| 1.179 | ethyl triazol-1-yl-4-carboxylate |
| 1.180 | N-methoxy-triazol-1-yl-4-carboxamide |
| 1.181 | isopropyl triazol-1-yl-4-carboxylate |
| 1.182 | methyl triazol-3-yl-4-carboxylate |
| 1.183 | N,N-dimethyl-triazol-1-yl-4-carboxamide |
| 1.184 | N-(4-methoxyphenyl)-triazol-1-yl-4-carboxamide |
| 1.185 | N-(4-chlorophenyl)-triazol-1-yl-4-carboxamide |
| 1.186 | N-(4-pyridyl)-triazol-1-yl-4-carboxamide |
| 1.187 | N-methoxy-pyrazol-1-yl-4-methanimine |
| 1.188 | N-ethoxy-pyrazol-1-yl-4-methanimine |
| 1.189 | N-propoxy-pyrazol-1-yl-4-methanimine |
| 1.190 | N-isopropoxy-pyrazol-1-yl-4-methanimine |
| 1.191 | N-benzyloxy-pyrazol-1-yl-4-methanimine |
| 1.192 | N-prop-2-ynoxy-pyrazol-1-yl-4-methanimine |
| 1.193 | N-methyl-triazol-3-yl-4-carboxamide |
| 1.194 | N-methoxy-pyrrolidin-1-yl-3-imine |
| 1.195 | N-methoxy-piperidin-1-yl-4-imine |
| 1.196 | 5-methylsulfonyl-1,2,4-triazol-1-yl |
| 1.197 | 5-methylsulfinyl-1,2,4-triazol-1-yl |
| 1.198 | 3-methylsulfonyl-1,2,4-triazol-1-yl |
| 1.199 | 3-methylsulfinyl-1,2,4-triazol-1-yl |
| 1.200 | 5-methylsulfanyl-1,2,4-triazol-1-yl |
| 1.201 | 3-methylsulfanyl-1,2,4-triazol-1-yl |
| 1.202 | 1-piperidin-1-yl |
| 1.203 | 4-morpholin-1-yl |
| 1.204 | 4-thiomorpholin-1-yl |
| 1.205 | 4-methylsulfonyl-piperazin-1-yl |
| 1.206 | 2,6-dimethyl-4-morpholin-1-yl |

Each of Tables 1.2 to 1.11 (which follow Table 1.1) make available 206 individual compounds of Formula (I-1) wherein n, $A^1$, $A^2$, $A^3$, $A^4$, $R^1$ and $R^2$ are as specifically defined in Tables 1.2 to 1.11, which refer to Table 1 wherein Z is specifically defined.

Table 1.2: This table discloses 206 specific compounds of Formula (I-1) wherein n is 1, $A^2$, $A^3$, $A^4$, $R^1$ and $R^2$ are hydrogen, $A^1$ is fluorine and Z is as defined above in Table 1.

Table 1.3: This table discloses 206 specific compounds of Formula (I-1) wherein n is 1, $A^2$, $A^3$, $A^4$, $R^1$ and $R^2$ are hydrogen, $A^1$ is chlorine and Z is as defined above in Table 1.

Table 1.4: This table discloses 206 specific compounds of Formula (I-1) wherein n is 1, $A^2$, $A^3$, $A^4$, $R^1$ and $R^2$ are hydrogen, $A^1$ is methyl and Z is as defined above in Table 1.

Table 1.5: This table discloses 206 specific compounds of Formula (I-1) wherein n is 1, $A^1$, $A^2$, $A^4$, $R^1$ and $R^2$ are hydrogen, $A^3$ is fluorine and Z is as defined above in Table 1.

Table 1.6: This table discloses 206 specific compounds of Formula (I-1) wherein n is 1, $A^2$, $A^4$, $R^1$ and $R^2$ are hydrogen, $A^1$ and $A^3$ are fluorine and Z is as defined above in Table 1.

Table 1.7: This table discloses 206 specific compounds of Formula (I-1) wherein n is 1, $A^3$, $A^4$, $R^1$ and $R^2$ are hydrogen, $A^1$ and $A^2$ are fluorine and Z is as defined above in Table 1.

Table 1.8: This table discloses 206 specific compounds of Formula (I-1) wherein n is 1, $A^2$, $A^3$, $R^1$ and $R^2$ are hydrogen, $A^1$ and $A^4$ are fluorine and Z is as defined above in Table 1.

Table 1.9: This table discloses 206 specific compounds of Formula (I-1) wherein n is 1, $A^1$, $A^2$, $R^1$ and $R^2$ are hydrogen, $A^3$ and $A^4$ are fluorine and Z is as defined above in Table 1.

Table 1.10: This table discloses 206 specific compounds of Formula (I-1) wherein n is 1, $A^1$, $A^2$, $A^3$, $A^4$ and $R^1$ are hydrogen, $R^2$ is methyl and Z is as defined above in Table 1.

Table 1.11: This table discloses 206 specific compounds of Formula (I-1) wherein n is 1, $A^1$, $A^2$, $A^4$ and $R^1$ are hydrogen, $A^3$ is fluorine, $R^2$ is methyl and Z is as defined above in Table 1.

Table 2.1: This table discloses 58 specific compounds of Formula (I-2):

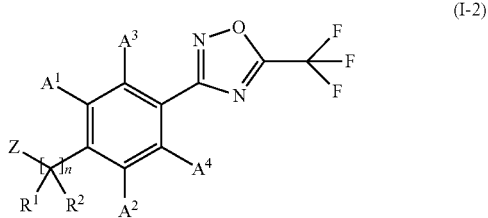

wherein n is 1, $A^1$, $A^2$, $A^3$, $A^4$, $R^1$ and $R^2$ are hydrogen, and Z is as defined below in Table 2.

TABLE 2

| Compound no. | Z |
| --- | --- |
| 2.001 | pyrrolidin-2-one |
| 2.002 | piperidin-2-one |
| 2.003 | morpholin-3-one |
| 2.004 | 4,4-dimethyl-isoxazolidin-3-one |
| 2.005 | 5,5-dimethyl-isoxazolidin-3-one |
| 2.006 | 3-methyl-pyrrolidin-2-one |
| 2.007 | 4-methyl-pyrrolidin-2-one |
| 2.008 | 3-azabicyclo[2.2.1]hept-5-en-2-one |
| 2.009 | 3-methyl-piperidin-2-one |
| 2.010 | 4,4-dimethyl-piperidine-2,6-dione |
| 2.011 | 5-methyl-pyrrolidin-2-one |
| 2.012 | 6-methyl-piperidin-2-one |
| 2.013 | 3-azabicyclo[2.2.2]octan-2-one |
| 2.014 | 3,3-dimethyl-piperidin-2-one |
| 2.015 | 4-methyl-piperidin-2-one |
| 2.016 | 5-methyl-piperidin-2-one |
| 2.017 | 3-methoxy-piperidin-2-one |
| 2.018 | 4-(trifluoromethyl)-azetidin-2-one |
| 2.019 | 5-(difluoromethyl)-pyrrolidin-2-one |
| 2.020 | azetidin-2-one |
| 2.021 | 3-azabicyclo[2.2.1]heptan-2-one |
| 2.022 | 4-azaspiro[2.5]octan-5-one |
| 2.023 | 1-methyl-piperazine-2,5-dione |
| 2.024 | 4-azaspiro[2.4]heptan-5-one |
| 2.025 | (tert-butyl 3-oxo-piperazine-1-carboxylate) |
| 2.026 | 4-(2-methoxyacetyl)-piperazin-2-one |
| 2.027 | ethyl 3-oxopiperazine-1-carboxylate |

TABLE 2-continued

| Compound no. | Z |
| --- | --- |
| 2.028 | N-methyl-3-oxopiperazine-1-carboxamide |
| 2.029 | N,N-dimethyl-3-oxopiperazine-1-carboxamide |
| 2.030 | 4-acetylpiperazin-2-one |
| 2.031 | oxazinan-3-one |
| 2.032 | N-methoxy-N-methyl-3-oxopiperazine-1-carboxamide |
| 2.033 | 4-(cyclopropanecarbonyl)-piperazin-2-one |
| 2.034 | 4-methylsulfonylpiperazin-2-one |
| 2.035 | N,N-dimethyl-3-oxopiperazine-1-sulfonamide |
| 2.036 | oxazolidin-2-one |
| 2.037 | 1-methyl-imidazolidin-2-one |
| 2.038 | 3-methyl-imidazolidine-2,4-dione |
| 2.039 | 1-methyl-hexahydropyrimidin-2-one |
| 2.040 | piperidine-2,6-dione |
| 2.041 | 1-methyl-imidazolidine-2,4-dione |
| 2.042 | pyrrolidine-2,5-dione |
| 2.043 | 4-acetyl-piperazine-2,6-dione |
| 2.044 | N,N-dimethyl-3,5-dioxopiperazine-1-carboxamide |
| 2.045 | ethyl 3,5-dioxo-piperazine-1-carboxylate |
| 2.046 | N-methyl-3,5-dioxopiperazine-1-carboxamide |
| 2.047 | 4-methylsulfonyl-piperazine-2,6-dione |
| 2.048 | N,N-dimethyl-3,5-dioxopiperazine-1-sulfonamide |
| 2.049 | piperazin-4-ium-2,6-dione |
| 2.050 | 4,4-dimethyl-isoxazolidin-3-one |
| 2.051 | imidazolidine-2,4-dione |
| 2.052 | azepan-2-one |
| 2.053 | piperazin-4-ium-2-one |
| 2.054 | tert-butyl 3,5-dioxopiperazine-1-carboxylate |
| 2.055 | 1-methyl-tetrazol-5-one |
| 2.056 | 1,2-thiazolidine 1,1-dioxide |
| 2.057 | 2-methyl-1,2,6-thiadiazinane 1,1-dioxide |
| 2.058 | 1-methoxy-imidazolidin-2-one |

Each of Tables 2.2 and 2.3 (which follow Table 2.1) make available 58 individual compounds of Formula (I-2) wherein n, $A^1$, $A^2$, $A^3$, $A^4$, $R^1$ and $R^2$ are as specifically defined in Tables 2.2 and 2.3, which refer to Table 2 wherein Z is specifically defined.

Table 2.2: This table discloses 58 specific compounds of Formula (I-2) wherein n is 1, $A^2$, $A^3$, $A^4$, $R^1$ and $R^2$ are hydrogen, $A^1$ is fluorine and Z is as defined above in Table 2.

Table 2.3: This table discloses 58 specific compounds of Formula (I-2) wherein n is 1, $A^1$, $A^2$, $A^4$, $R^1$ and $R^2$ are hydrogen, $A^3$ is fluorine and Z is as defined above in Table 2.

Table 3.1: This table discloses 373 specific compounds of Formula (I-3):

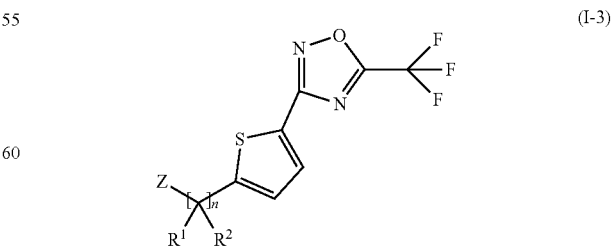

wherein n is 1, $R^1$ and $R^2$ are hydrogen, and Z is as defined below in Table 3.

TABLE 3

| Compound no. | Z |
|---|---|
| 3.001 | 2H-pyrazole-3-carboxylic acid |
| 3.002 | methyl 2H-pyrazole-3-carboxylate |
| 3.003 | ethyl 2H-pyrazole-3-carboxylate |
| 3.004 | propyl 2H-pyrazole-3-carboxylate |
| 3.005 | prop-2-enyl 2H-pyrazole-3-carboxylate |
| 3.006 | prop-2-ynyl 2H-pyrazole-3-carboxylate |
| 3.007 | tert-butyl 2H-pyrazole-3-carboxylate |
| 3.008 | isopropyl 2H-pyrazole-3-carboxylate |
| 3.009 | 2-(dimethylamino)ethyl 2H-pyrazole-3-carboxylate |
| 3.010 | 2-methoxyethyl 2H-pyrazole-3-carboxylate |
| 3.011 | cyclopropyl 2H-pyrazole-3-carboxylate |
| 3.012 | cyclopropylmethyl 2H-pyrazole-3-carboxylate |
| 3.013 | 2H-pyrazole-3-carboxamide |
| 3.014 | N-methyl-2H-pyrazole-3-carboxamide |
| 3.015 | N-ethyl-2H-pyrazole-3-carboxamide |
| 3.016 | N-propyl-2H-pyrazole-3-carboxamide |
| 3.017 | N-isopropyl-2H-pyrazole-3-carboxamide |
| 3.018 | N-prop-2-enyl-2H-pyrazole-3-carboxamide |
| 3.019 | N-prop-2-ynyl-2H-pyrazole-3-carboxamide |
| 3.020 | N-cyclopropyl-2H-pyrazole-3-carboxamide |
| 3.021 | N-(cyclopropylmethyl)-2H-pyrazole-3-carboxamide |
| 3.022 | N-(2-methoxyethyl)-2H-pyrazole-3-carboxamide |
| 3.023 | N-methoxy-2H-pyrazole-3-carboxamide |
| 3.024 | N-ethoxy-2H-pyrazole-3-carboxamide |
| 3.025 | N-prop-2-enyloxy-2H-pyrazole-3-carboxamide |
| 3.026 | N-methoxy-N-methyl-2H-pyrazole-3-carboxamide |
| 3.027 | N-ethoxy-N-methyl-2H-pyrazole-3-carboxamide |
| 3.028 | N,N-dimethyl-2H-pyrazole-3-carboxamide |
| 3.029 | N,N-diethyl-2H-pyrazole-3-carboxamide |
| 3.030 | N-ethyl-N-methyl-2H-pyrazole-3-carboxamide |
| 3.031 | N-prop-2-enyl-N-methyl-2H-pyrazole-3-carboxamide |
| 3.032 | 1H-pyrazole-3-carboxylic acid |
| 3.033 | methyl 1H-pyrazole-3-carboxylate |
| 3.034 | ethyl 1H-pyrazole-3-carboxylate |
| 3.035 | propyl 1H-pyrazole-3-carboxylate |
| 3.036 | prop-2-enyl 1H-pyrazole-3-carboxylate |
| 3.037 | prop-2-ynyl 1H-pyrazole-3-carboxylate |
| 3.038 | tert-butyl 1H-pyrazole-3-carboxylate |
| 3.039 | isopropyl 1H-pyrazole-3-carboxylate |
| 3.040 | 2-(dimethylamino)ethyl 1H-pyrazole-3-carboxylate |
| 3.041 | 2-methoxyethyl 1H-pyrazole-3-carboxylate |
| 3.042 | cyclopropyl 1H-pyrazole-3-carboxylate |
| 3.043 | cyclopropylmethyl 1H-pyrazole-3-carboxylate |
| 3.044 | 1H-pyrazole-3-carboxamide |
| 3.045 | N-methyl-1H-pyrazole-3-carboxamide |
| 3.046 | N-ethyl-1H-pyrazole-3-carboxamide |
| 3.047 | N-propyl-1H-pyrazole-3-carboxamide |
| 3.048 | N-isopropyl-1H-pyrazole-3-carboxamide |
| 3.049 | N-prop-2-enyl-1H-pyrazole-3-carboxamide |
| 3.050 | N-prop-2-ynyl-1H-pyrazole-3-carboxamide |
| 3.051 | N-cyclopropyl-1H-pyrazole-3-carboxamide |
| 3.052 | N-(cyclopropylmethyl)-1H-pyrazole-3-carboxamide |
| 3.053 | N-(2-methoxyethyl)-1H-pyrazole-3-carboxamide |
| 3.054 | N-methoxy-1H-pyrazole-3-carboxamide |
| 3.055 | N-ethoxy-1H-pyrazole-3-carboxamide |
| 3.056 | N-prop-2-enyloxy-1H-pyrazole-3-carboxamide |
| 3.057 | N-methoxy-N-methyl-1H-pyrazole-3-carboxamide |
| 3.058 | N-ethoxy-N-methyl-1H-pyrazole-3-carboxamide |
| 3.059 | N,N-dimethyl-1H-pyrazole-3-carboxamide |
| 3.060 | N,N-diethyl-1H-pyrazole-3-carboxamide |
| 3.061 | N-ethyl-N-methyl-1H-pyrazole-3-carboxamide |
| 3.062 | N-prop-2-enyl-N-methyl-1H-pyrazole-3-carboxamide |
| 3.063 | 1H-imidazole-2-carboxylic acid |
| 3.064 | methyl 1H-imidazole-2-carboxylate |
| 3.065 | ethyl 1H-imidazole-2-carboxylate |
| 3.066 | propyl 1H-imidazole-2-carboxylate |
| 3.067 | prop-2-enyl 1H-imidazole-2-carboxylate |
| 3.068 | prop-2-ynyl 1H-imidazole-2-carboxylate |
| 3.069 | tert-butyl 1H-imidazole-2-carboxylate |
| 3.070 | isopropyl 1H-imidazole-2-carboxylate |
| 3.071 | 2-(dimethylamino)ethyl 1H-imidazole-2-carboxylate |
| 3.072 | 2-methoxyethyl 1H-imidazole-2-carboxylate |
| 3.073 | cyclopropyl 1H-imidazole-2-carboxylate |
| 3.074 | cyclopropylmethyl 1H-imidazole-2-carboxylate |
| 3.075 | 1H-imidazole-2-carboxamide |
| 3.076 | N-methyl-1H-imidazole-2-carboxamide |
| 3.077 | N-ethyl-1H-imidazole-2-carboxamide |
| 3.078 | N-propyl-1H-imidazole-2-carboxamide |
| 3.079 | N-isopropyl-1H-imidazole-2-carboxamide |
| 3.080 | N-prop-2-enyl-1H-imidazole-2-carboxamide |
| 3.081 | N-prop-2-ynyl-1H-imidazole-2-carboxamide |
| 3.082 | N-cyclopropyl-1H-imidazole-2-carboxamide |
| 3.083 | N-(cyclopropylmethyl)-1H-imidazole-2-carboxamide |
| 3.084 | N-(2-methoxyethyl)-1H-imidazole-2-carboxamide |
| 3.085 | N-methoxy-1H-imidazole-2-carboxamide |
| 3.086 | N-ethoxy-1H-imidazole-2-carboxamide |
| 3.087 | N-prop-2-enyloxy-1H-imidazole-2-carboxamide |
| 3.088 | N-methoxy-N-methyl-1H-imidazole-2-carboxamide |
| 3.089 | N-ethoxy-N-methyl-1H-imidazole-2-carboxamide |
| 3.090 | N,N-dimethyl-1H-imidazole-2-carboxamide |
| 3.091 | N,N-diethyl-1H-imidazole-2-carboxamide |
| 3.092 | N-ethyl-N-methyl-1H-imidazole-2-carboxamide |
| 3.093 | N-prop-2-enyl-N-methyl-1H-imidazole-2-carboxamide |
| 3.094 | 1H-imidazole-4-carboxylic acid |
| 3.095 | methyl 1H-imidazole-4-carboxylate |
| 3.096 | ethyl 1H-imidazole-4-carboxylate |
| 3.097 | propyl 1H-imidazole-4-carboxylate |
| 3.098 | prop-2-enyl 1H-imidazole-4-carboxylate |
| 3.099 | prop-2-ynyl 1H-imidazole-4-carboxylate |
| 3.100 | tert-butyl 1H-imidazole-4-carboxylate |
| 3.101 | isopropyl 1H-imidazole-4-carboxylate |
| 3.102 | 2-(dimethylamino)ethyl 1H-imidazole-4-carboxylate |
| 3.103 | 2-methoxyethyl 1H-imidazole-4-carboxylate |
| 3.104 | cyclopropyl 1H-imidazole-4-carboxylate |
| 3.105 | cyclopropylmethyl 1H-imidazole-4-carboxylate |
| 3.106 | 1H-imidazole-4-carboxamide |
| 3.107 | N-methyl-1H-imidazole-4-carboxamide |
| 3.108 | N-ethyl-1H-imidazole-4-carboxamide |
| 3.109 | N-propyl-1H-imidazole-4-carboxamide |
| 3.110 | N-isopropyl-1H-imidazole-4-carboxamide |
| 3.111 | N-prop-2-enyl-1H-imidazole-4-carboxamide |
| 3.112 | N-prop-2-ynyl-1H-imidazole-4-carboxamide |
| 3.113 | N-cyclopropyl-1H-imidazole-4-carboxamide |
| 3.114 | N-(cyclopropylmethyl)-1H-imidazole-4-carboxamide |
| 3.115 | N-(2-methoxyethyl)-1H-imidazole-4-carboxamide |
| 3.116 | N-methoxy-1H-imidazole-4-carboxamide |
| 3.117 | N-ethoxy-1H-imidazole-4-carboxamide |
| 3.118 | N-prop-2-enyloxy-1H-imidazole-4-carboxamide |
| 3.119 | N-methoxy-N-methyl-1H-imidazole-4-carboxamide |
| 3.120 | N-ethoxy-N-methyl-1H-imidazole-4-carboxamide |
| 3.121 | N,N-dimethyl-1H-imidazole-4-carboxamide |
| 3.122 | N,N-diethyl-1H-imidazole-4-carboxamide |
| 3.123 | N-ethyl-N-methyl-1H-imidazole-4-carboxamide |
| 3.124 | N-prop-2-enyl-N-methyl-1H-imidazole-4-carboxamide |
| 3.125 | 3H-imidazole-4-carboxylic acid |
| 3.126 | methyl 3H-imidazole-4-carboxylate |
| 3.127 | ethyl 3H-imidazole-4-carboxylate |
| 3.128 | propyl 3H-imidazole-4-carboxylate |
| 3.129 | prop-2-enyl 3H-imidazole-4-carboxylate |
| 3.130 | prop-2-ynyl 3H-imidazole-4-carboxylate |
| 3.131 | tert-butyl 3H-imidazole-4-carboxylate |
| 3.132 | isopropyl 3H-imidazole-4-carboxylate |
| 3.133 | 2-(dimethylamino)ethyl 3H-imidazole-4-carboxylate |
| 3.134 | 2-methoxyethyl 3H-imidazole-4-carboxylate |
| 3.135 | cyclopropyl 3H-imidazole-4-carboxylate |
| 3.136 | cyclopropylmethyl 3H-imidazole-4-carboxylate |
| 3.137 | 3H-imidazole-4-carboxamide |
| 3.138 | N-methyl-3H-imidazole-4-carboxamide |
| 3.139 | N-ethyl-3H-imidazole-4-carboxamide |
| 3.140 | N-propyl-3H-imidazole-4-carboxamide |
| 3.141 | N-isopropyl-3H-imidazole-4-carboxamide |
| 3.142 | N-prop-2-enyl-3H-imidazole-4-carboxamide |
| 3.143 | N-prop-2-ynyl-3H-imidazole-4-carboxamide |
| 3.144 | N-cyclopropyl-3H-imidazole-4-carboxamide |
| 3.145 | N-(cyclopropylmethyl)-3H-imidazole-4-carboxamide |
| 3.146 | N-(2-methoxyethyl)-3H-imidazole-4-carboxamide |
| 3.147 | N-methoxy-3H-imidazole-4-carboxamide |
| 3.148 | N-ethoxy-3H-imidazole-4-carboxamide |
| 3.149 | N-prop-2-enyloxy-3H-imidazole-4-carboxamide |
| 3.150 | N-methoxy-N-methyl-3H-imidazole-4-carboxamide |
| 3.151 | N-ethoxy-N-methyl-3H-imidazole-4-carboxamide |
| 3.152 | N,N-dimethyl-3H-imidazole-4-carboxamide |
| 3.153 | N,N-diethyl-3H-imidazole-4-carboxamide |
| 3.154 | N-ethyl-N-methyl-3H-imidazole-4-carboxamide |

TABLE 3-continued

| Compound no. | Z |
|---|---|
| 3.155 | N-prop-2-enyl-N-methyl-3H-imidazole-4-carboxamide |
| 3.156 | 2H-1,2,4-triazole-3-carboxylic acid |
| 3.157 | methyl 2H-1,2,4-triazole-3-carboxylate |
| 3.158 | ethyl 2H-1,2,4-triazole-3-carboxylate |
| 3.159 | propyl 2H-1,2,4-triazole-3-carboxylate |
| 3.160 | prop-2-enyl 2H-1,2,4-triazole-3-carboxylate |
| 3.161 | prop-2-ynyl 2H-1,2,4-triazole-3-carboxylate |
| 3.162 | tert-butyl 2H-1,2,4-triazole-3-carboxylate |
| 3.163 | isopropyl 2H-1,2,4-triazole-3-carboxylate |
| 3.164 | 2-(dimethylamino)ethyl 2H-1,2,4-triazole-3-carboxylate |
| 3.165 | 2-methoxyethyl 2H-1,2,4-triazole-3-carboxylate |
| 3.166 | cyclopropyl 2H-1,2,4-triazole-3-carboxylate |
| 3.167 | cyclopropylmethyl 2H-1,2,4-triazole-3-carboxylate |
| 3.168 | 2H-1,2,4-triazole-3-carboxamide |
| 3.169 | N-methyl-2H-1,2,4-triazole-3-carboxamide |
| 3.170 | N-ethyl-2H-1,2,4-triazole-3-carboxamide |
| 3.171 | N-propyl-2H-1,2,4-triazole-3-carboxamide |
| 3.172 | N-isopropyl-2H-1,2,4-triazole-3-carboxamide |
| 3.173 | N-prop-2-enyl-2H-1,2,4-triazole-3-carboxamide |
| 3.174 | N-prop-2-ynyl-2H-1,2,4-triazole-3-carboxamide |
| 3.175 | N-cyclopropyl-2H-1,2,4-triazole-3-carboxamide |
| 3.176 | N-(cyclopropylmethyl)-2H-1,2,4-triazole-3-carboxamide |
| 3.177 | N-(2-methoxyethyl)-2H-1,2,4-triazole-3-carboxamide |
| 3.178 | N-methoxy-2H-1,2,4-triazole-3-carboxamide |
| 3.179 | N-ethoxy-2H-1,2,4-triazole-3-carboxamide |
| 3.180 | N-prop-2-enyloxy-2H-1,2,4-triazole-3-carboxamide |
| 3.181 | N-methoxy-N-methyl-2H-1,2,4-triazole-3-carboxamide |
| 3.182 | N-ethoxy-N-methyl-2H-1,2,4-triazole-3-carboxamide |
| 3.183 | N,N-dimethyl-2H-1,2,4-triazole-3-carboxamide |
| 3.184 | N,N-diethyl-2H-1,2,4-triazole-3-carboxamide |
| 3.185 | N-ethyl-N-methyl-2H-1,2,4-triazole-3-carboxamide |
| 3.186 | N-prop-2-enyl-N-methyl-2H-1,2,4-triazole-3-carboxamide |
| 3.187 | 1H-1,2,4-triazole-3-carboxylic acid |
| 3.188 | methyl 1H-1,2,4-triazole-3-carboxylate |
| 3.189 | ethyl 1H-1,2,4-triazole-3-carboxylate |
| 3.190 | propyl 1H-1,2,4-triazole-3-carboxylate |
| 3.191 | prop-2-enyl 1H-1,2,4-triazole-3-carboxylate |
| 3.192 | prop-2-ynyl 1H-1,2,4-triazole-3-carboxylate |
| 3.193 | tert-butyl 1H-1,2,4-triazole-3-carboxylate |
| 3.194 | isopropyl 1H-1,2,4-triazole-3-carboxylate |
| 3.195 | 2-(dimethylamino)ethyl 1H-1,2,4-triazole-3-carboxylate |
| 3.196 | 2-methoxyethyl 1H-1,2,4-triazole-3-carboxylate |
| 3.197 | cyclopropyl 1H-1,2,4-triazole-3-carboxylate |
| 3.198 | cyclopropylmethyl 1H-1,2,4-triazole-3-carboxylate |
| 3.199 | 1H-1,2,4-triazole-3-carboxamide |
| 3.200 | N-methyl-1H-1,2,4-triazole-3-carboxamide |
| 3.201 | N-ethyl-1H-1,2,4-triazole-3-carboxamide |
| 3.202 | N-propyl-1H-1,2,4-triazole-3-carboxamide |
| 3.203 | N-isopropyl-1H-1,2,4-triazole-3-carboxamide |
| 3.204 | N-prop-2-enyl-1H-1,2,4-triazole-3-carboxamide |
| 3.205 | N-prop-2-ynyl-1H-1,2,4-triazole-3-carboxamide |
| 3.206 | N-cyclopropyl-1H-1,2,4-triazole-3-carboxamide |
| 3.207 | N-(cyclopropylmethyl)-1H-1,2,4-triazole-3-carboxamide |
| 3.208 | N-(2-methoxyethyl)-1H-1,2,4-triazole-3-carboxamide |
| 3.209 | N-methoxy-1H-1,2,4-triazole-3-carboxamide |
| 3.210 | N-ethoxy-1H-1,2,4-triazole-3-carboxamide |
| 3.211 | N-prop-2-enyloxy-1H-1,2,4-triazole-3-carboxamide |
| 3.212 | N-methoxy-N-methyl-1H-1,2,4-triazole-3-carboxamide |
| 3.213 | N-ethoxy-N-methyl-1H-1,2,4-triazole-3-carboxamide |
| 3.214 | N,N-dimethyl-1H-1,2,4-triazole-3-carboxamide |
| 3.215 | N,N-diethyl-1H-1,2,4-triazole-3-carboxamide |
| 3.216 | N-ethyl-N-methyl-1H-1,2,4-triazole-3-carboxamide |
| 3.217 | N-prop-2-enyl-N-methyl-1H-1,2,4-triazole-3-carboxamide |
| 3.218 | 3H-triazole-4-carboxylic acid |
| 3.219 | methyl 3H-triazole-4-carboxylate |
| 3.220 | ethyl 3H-triazole-4-carboxylate |
| 3.221 | propyl 3H-triazole-4-carboxylate |
| 3.222 | prop-2-enyl 3H-triazole-4-carboxylate |
| 3.223 | prop-2-ynyl 3H-triazole-4-carboxylate |
| 3.224 | tert-butyl 3H-triazole-4-carboxylate |
| 3.225 | isopropyl 3H-triazole-4-carboxylate |
| 3.226 | 2-(dimethylamino)ethyl 3H-triazole-4-carboxylate |
| 3.227 | 2-methoxyethyl 3H-triazole-4-carboxylate |
| 3.228 | cyclopropyl 3H-triazole-4-carboxylate |
| 3.229 | cyclopropylmethyl 3H-triazole-4-carboxylate |
| 3.230 | 3H-triazole-4-carboxamide |
| 3.231 | N-methyl-3H-triazole-4-carboxamide |
| 3.232 | N-ethyl-3H-triazole-4-carboxamide |
| 3.233 | N-propyl-3H-triazole-4-carboxamide |
| 3.234 | N-isopropyl-3H-triazole-4-carboxamide |
| 3.235 | N-prop-2-enyl-3H-triazole-4-carboxamide |
| 3.236 | N-prop-2-ynyl-3H-triazole-4-carboxamide |
| 3.237 | N-cyclopropyl-3H-triazole-4-carboxamide |
| 3.238 | N-(cyclopropylmethyl)-3H-triazole-4-carboxamide |
| 3.239 | N-(2-methoxyethyl)-3H-triazole-4-carboxamide |
| 3.240 | N-methoxy-3H-triazole-4-carboxamide |
| 3.241 | N-ethoxy-3H-triazole-4-carboxamide |
| 3.242 | N-prop-2-enyloxy-3H-triazole-4-carboxamide |
| 3.243 | N-methoxy-N-methyl-3H-triazole-4-carboxamide |
| 3.244 | N-ethoxy-N-methyl-3H-triazole-4-carboxamide |
| 3.245 | N,N-dimethyl-3H-triazole-4-carboxamide |
| 3.246 | N,N-diethyl-3H-triazole-4-carboxamide |
| 3.247 | N-ethyl-N-methyl-3H-triazole-4-carboxamide |
| 3.248 | N-prop-2-enyl-N-methyl-3H-triazole-4-carboxamide |
| 3.249 | 2H-triazole-4-carboxylic acid |
| 3.250 | methyl 2H-triazole-4-carboxylate |
| 3.251 | ethyl 2H-triazole-4-carboxylate |
| 3.252 | propyl 2H-triazole-4-carboxylate |
| 3.253 | prop-2-enyl 2H-triazole-4-carboxylate |
| 3.254 | prop-2-ynyl 2H-triazole-4-carboxylate |
| 3.255 | tert-butyl 2H-triazole-4-carboxylate |
| 3.256 | isopropyl 2H-triazole-4-carboxylate |
| 3.257 | 2-(dimethylamino)ethyl 2H-triazole-4-carboxylate |
| 3.258 | 2-methoxyethyl 2H-triazole-4-carboxylate |
| 3.259 | cyclopropyl 2H-triazole-4-carboxylate |
| 3.260 | cyclopropylmethyl 2H-triazole-4-carboxylate |
| 3.261 | 2H-triazole-4-carboxamide |
| 3.262 | N-methyl-2H-triazole-4-carboxamide |
| 3.263 | N-ethyl-2H-triazole-4-carboxamide |
| 3.264 | N-propyl-2H-triazole-4-carboxamide |
| 3.265 | N-isopropyl-2H-triazole-4-carboxamide |
| 3.266 | N-prop-2-enyl-2H-triazole-4-carboxamide |
| 3.267 | N-prop-2-ynyl-2H-triazole-4-carboxamide |
| 3.268 | N-cyclopropyl-2H-triazole-4-carboxamide |
| 3.269 | N-(cyclopropylmethyl)-2H-triazole-4-carboxamide |
| 3.270 | N-(2-methoxyethyl)-2H-triazole-4-carboxamide |
| 3.271 | N-methoxy-2H-triazole-4-carboxamide |
| 3.272 | N-ethoxy-2H-triazole-4-carboxamide |
| 3.273 | N-prop-2-enyloxy-2H-triazole-4-carboxamide |
| 3.274 | N-methoxy-N-methyl-2H-triazole-4-carboxamide |
| 3.275 | N-ethoxy-N-methyl-2H-triazole-4-carboxamide |
| 3.276 | N,N-dimethyl-2H-triazole-4-carboxamide |
| 3.277 | N,N-diethyl-2H-triazole-4-carboxamide |
| 3.278 | N-ethyl-N-methyl-2H-triazole-4-carboxamide |
| 3.279 | N-prop-2-enyl-N-methyl-2H-triazole-4-carboxamide |
| 3.280 | 1H-triazole-4-carboxylic acid |
| 3.281 | methyl 1H-triazole-4-carboxylate |
| 3.282 | ethyl 1H-triazole-4-carboxylate |
| 3.283 | propyl 1H-triazole-4-carboxylate |
| 3.284 | prop-2-enyl 1H-triazole-4-carboxylate |
| 3.285 | prop-2-ynyl 1H-triazole-4-carboxylate |
| 3.286 | tert-butyl 1H-triazole-4-carboxylate |
| 3.287 | isopropyl 1H-triazole-4-carboxylate |
| 3.288 | 2-(dimethylamino)ethyl 1H-triazole-4-carboxylate |
| 3.289 | 2-methoxyethyl 1H-triazole-4-carboxylate |
| 3.290 | cyclopropyl 1H-triazole-4-carboxylate |
| 3.291 | cyclopropylmethyl 1H-triazole-4-carboxylate |
| 3.292 | 1H-triazole-4-carboxamide |
| 3.293 | N-methyl-1H-triazole-4-carboxamide |
| 3.294 | N-ethyl-1H-triazole-4-carboxamide |
| 3.295 | N-propyl-1H-triazole-4-carboxamide |
| 3.296 | N-isopropyl-1H-triazole-4-carboxamide |
| 3.297 | N-prop-2-enyl-1H-triazole-4-carboxamide |
| 3.298 | N-prop-2-ynyl-1H-triazole-4-carboxamide |
| 3.299 | N-cyclopropyl-1H-triazole-4-carboxamide |
| 3.300 | N-(cyclopropylmethyl)-1H-triazole-4-carboxamide |
| 3.301 | N-(2-methoxyethyl)-1H-triazole-4-carboxamide |
| 3.302 | N-methoxy-1H-triazole-4-carboxamide |
| 3.303 | N-ethoxy-1H-triazole-4-carboxamide |
| 3.304 | N-prop-2-enyloxy-1H-triazole-4-carboxamide |
| 3.305 | N-methoxy-N-methyl-1H-triazole-4-carboxamide |
| 3.306 | N-ethoxy-N-methyl-1H-triazole-4-carboxamide |
| 3.307 | N,N-dimethyl-1H-triazole-4-carboxamide |
| 3.308 | N,N-diethyl-1H-triazole-4-carboxamide |

TABLE 3-continued

| Compound no. | Z |
|---|---|
| 3.309 | N-ethyl-N-methyl-1H-triazole-4-carboxamide |
| 3.310 | N-prop-2-enyl-N-methyl-1H-triazole-4-carboxamide |
| 3.311 | 1H-tetrazole-5-carboxylic acid |
| 2.312 | methyl 1H-tetrazole-5-carboxylate |
| 3.313 | ethyl 1H-tetrazole-5-carboxylate |
| 3.314 | propyl 1H-tetrazole-5-carboxylate |
| 3.315 | prop-2-enyl 1H-tetrazole-5-carboxylate |
| 3.316 | prop-2-ynyl 1H-tetrazole-5-carboxylate |
| 3.317 | tert-butyl 1H-tetrazole-5-carboxylate |
| 3.318 | isopropyl 1H-tetrazole-5-carboxylate |
| 3.319 | 2-(dimethylamino)ethyl 1H-tetrazole-5-carboxylate |
| 3.320 | 2-methoxyethyl 1H-tetrazole-5-carboxylate |
| 3.321 | cyclopropyl 1H-tetrazole-5-carboxylate |
| 3.322 | cyclopropylmethyl 1H-tetrazole-5-carboxylate |
| 3.323 | 1H-tetrazole-5-carboxamide |
| 3.324 | N-methyl-1H-tetrazole-5-carboxamide |
| 3.325 | N-ethyl-1H-tetrazole-5-carboxamide |
| 3.326 | N-propyl-1H-tetrazole-5-carboxamide |
| 3.327 | N-isopropyl-1H-tetrazole-5-carboxamide |
| 3.328 | N-prop-2-enyl-1H-tetrazole-5-carboxamide |
| 3.329 | N-prop-2-ynyl-1H-tetrazole-5-carboxamide |
| 3.330 | N-cyclopropyl-1H-tetrazole-5-carboxamide |
| 3.331 | N-(cyclopropylmethyl)-1H-tetrazole-5-carboxamide |
| 3.332 | N-(2-methoxyethyl)-1H-tetrazole-5-carboxamide |
| 3.333 | N-methoxy-1H-tetrazole-5-carboxamide |
| 3.334 | N-ethoxy-1H-tetrazole-5-carboxamide |
| 3.335 | N-prop-2-enyloxy-1H-tetrazole-5-carboxamide |
| 3.336 | N-methoxy-N-methyl-1H-tetrazole-5-carboxamide |
| 3.337 | N-ethoxy-N-methyl-1H-tetrazole-5-carboxamide |
| 3.338 | N,N-dimethyl-1H-tetrazole-5-carboxamide |
| 3.339 | N,N-diethyl-1H-tetrazole-5-carboxamide |
| 3.340 | N-ethyl-N-methyl-1H-tetrazole-5-carboxamide |
| 3.341 | N-prop-2-enyl-N-methyl-1H-tetrazole-5-carboxamide |
| 3.342 | 2H-tetrazole-5-carboxylic acid |
| 3.343 | methyl 2H-tetrazole-5-carboxylate |
| 3.344 | ethyl 2H-tetrazole-5-carboxylate |
| 3.345 | propyl 2H-tetrazole-5-carboxylate |
| 3.346 | prop-2-enyl 2H-tetrazole-5-carboxylate |
| 3.347 | prop-2-ynyl 2H-tetrazole-5-carboxylate |
| 3.348 | tert-butyl 2H-tetrazole-5-carboxylate |
| 3.349 | isopropyl 2H-tetrazole-5-carboxylate |
| 3.350 | 2-(dimethylamino)ethyl 2H-tetrazole-5-carboxylate |
| 3.351 | 2-methoxyethyl 2H-tetrazole-5-carboxylate |
| 3.352 | cyclopropyl 2H-tetrazole-5-carboxylate |
| 3.353 | cyclopropylmethyl 2H-tetrazole-5-carboxylate |
| 3.354 | 2H-tetrazole-5-carboxamide |
| 3.355 | N-methyl-2H-tetrazole-5-carboxamide |
| 3.356 | N-ethyl-2H-tetrazole-5-carboxamide |
| 3.357 | N-propyl-2H-tetrazole-5-carboxamide |
| 3.358 | N-isopropyl-2H-tetrazole-5-carboxamide |
| 3.359 | N-prop-2-enyl-2H-tetrazole-5-carboxamide |
| 3.360 | N-prop-2-ynyl-2H-tetrazole-5-carboxamide |
| 3.361 | N-cyclopropyl-2H-tetrazole-5-carboxamide |
| 3.362 | N-(cyclopropylmethyl)-2H-tetrazole-5-carboxamide |
| 3.363 | N-(2-methoxyethyl)-2H-tetrazole-5-carboxamide |
| 3.364 | N-methoxy-2H-tetrazole-5-carboxamide |
| 3.365 | N-ethoxy-2H-tetrazole-5-carboxamide |
| 3.366 | N-prop-2-enyloxy-2H-tetrazole-5-carboxamide |
| 3.367 | N-methoxy-N-methyl-2H-tetrazole-5-carboxamide |
| 3.368 | N-ethoxy-N-methyl-2H-tetrazole-5-carboxamide |
| 3.369 | N,N-dimethyl-2H-tetrazole-5-carboxamide |
| 3.370 | N,N-diethyl-2H-tetrazole-5-carboxamide |
| 3.371 | N-ethyl-N-methyl-2H-tetrazole-5-carboxamide |
| 3.372 | N-prop-2-enyl-N-methyl-2H-tetrazole-5-carboxamide |
| 3.373 | ethyl 1H-pyrazole-4-carboxylate |

Table 3.2: This table discloses a specific compound of Formula (I-3) wherein n is 1, $R^1$ and $R^2$ are hydrogen, and Z is N-(2-methoxyethyl)-1H-pyrazole-4-carboxamide.

Table 3.3: This table discloses 373 specific compounds of Formula (I-3) wherein n is 1, $R^1$ is hydrogen, $R^2$ is methyl and Z is as defined above in Table 3.

Table 4.1a: This table discloses 139 specific compounds of Formula (I-4a):

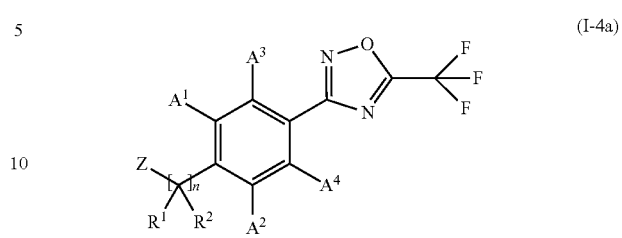

(I-4a)

wherein n is 0, $A^1$, $A^2$, $A^3$, $A^4$, $R^1$ and $R^2$ are hydrogen, and Z is —C(=W)—$R^5$, wherein W is O and $R^5$ is as defined below in Table 4.

TABLE 4

| Compound no. | $R^5$ |
|---|---|
| 4.001 | 2-fluorophenyl |
| 4.002 | 3-fluorophenyl |
| 4.003 | 4-fluorophenyl |
| 4.004 | 2-chlorophenyl |
| 4.005 | 3-chlorophenyl |
| 4.006 | 4-chlorophenyl |
| 4.007 | 2-cyanophenyl |
| 4.008 | 3-cyanophenyl |
| 4.009 | 4-cyanophenyl |
| 4.010 | 2-methylphenyl |
| 4.011 | 3-methylphenyl |
| 4.012 | 4-methylphenyl |
| 4.013 | 2-trifluorophenyl |
| 4.014 | 3-trifluorophenyl |
| 4.015 | 4-trifluorophenyl |
| 4.016 | 2-difluorophenyl |
| 4.017 | 3-difluorophenyl |
| 4.018 | 4-difluorophenyl |
| 4.019 | 2-methoxyphenyl |
| 4.020 | 3-methoxyphenyl |
| 4.021 | 4-methoxyphenyl |
| 4.022 | 2-difluoromethoxyphenyl |
| 4.023 | 3-difluoromethoxyphenyl |
| 4.024 | 4-difluoromethoxyphenyl |
| 4.025 | 2-trifluoromethoxyphenyl |
| 4.026 | 3-trifluoromethoxyphenyl |
| 4.027 | 4-trifluoromethoxyphenyl |
| 4.028 | 2-pyridyl |
| 4.029 | 3-pyridyl |
| 4.030 | 4-pyridyl |
| 4.031 | 2-thiazolyl |
| 4.032 | 4-thiazolyl |
| 4.033 | 5-thiazolyl |
| 4.034 | 4-methylthiazol-2-yl |
| 4.035 | 5-methylthiazol-2-yl |
| 4.036 | 4-ethylthiazol-2-yl |
| 4.037 | 5-ethylthiazol-2-yl |
| 4.038 | 2-methylthiazol-4-yl |
| 4.039 | 2-ethylthiazol-4-yl |
| 4.040 | 1-methylpyrazol-3-yl |
| 4.041 | 1-ethylpyrazol-3-yl |
| 4.042 | 1-methylpyrazol-4-yl |
| 4.043 | 1-ethylpyrazol-4-yl |
| 4.044 | 1H-pyrazol-3-yl |
| 4.045 | 1-methylpyrazol-3-yl |
| 4.046 | 1,5-dimethylpyrazol-3-yl |
| 4.047 | 1-acylpyrazol-3-yl |
| 4.048 | 5-methylisoxazol-3-yl |
| 4.049 | 5-ethylisoxazol-3-yl |
| 4.050 | 5-isopropylisoxazol-3-yl |
| 4.051 | 3-methylisoxazol-5-yl |
| 4.052 | 3-ethylisoxazol-5-yl |
| 4.053 | 3-isopropylisoxazol-5-yl |
| 4.054 | 5-methylisoxazol-3-yl |
| 4.055 | 5-ethylisoxazol-3-yl |

TABLE 4-continued

| Compound no. | R⁵ |
|---|---|
| 4.056 | 5-isopropylisoxazol-3-yl |
| 4.057 | 5-methyl-1H-pyrazol-3-yl |
| 4.058 | 5-ethyl-1H-pyrazol-3-yl |
| 4.059 | 4,5-dihydroisoxazol-3-yl |
| 4.060 | 5,5-dimethyl-4H-isoxazol-3-yl |
| 4.061 | 4,4-dimethyl-4H-isoxazol-3-yl |
| 4.062 | 3,3-dimethyl-2H-isoxazol-5-yl |
| 4.063 | 2-pyrimidinyl |
| 4.064 | 4-pyrimidinyl |
| 4.065 | 3-methylisothiazol-5-yl |
| 4.066 | 3-ethylisothiazol-5-yl |
| 4.067 | 4-methyl-2-pyridyl |
| 4.068 | 5-methyl-3-pyridyl |
| 4.069 | 5-methyl-2-pyridyl |
| 4.070 | 3-methyl-4-pyridyl |
| 4.071 | 5-pyrimidinyl |
| 4.072 | 1H-imidazol-2-yl |
| 4.073 | 1H-imidazol-5-yl |
| 4.074 | 2-methyl-1H-imidazol-5-yl |
| 4.075 | 2-ethyl-1H-imidazol-5-yl |
| 4.076 | 5-methyl-1H-imidazol-2-yl |
| 4.077 | 5-ethyl-1H-imidazol-2-yl |
| 4.078 | 1,2-dimethylimidazol-5-yl |
| 4.079 | 2-cyano-1-methyl-imidazol-5-yl |
| 4.080 | 1,5-dimethylimidazol-2-yl |
| 4.081 | 4-methylimidazol-2-yl |
| 4.082 | 5-methylimidazol-2-yl |
| 4.083 | 4-ethylimidazol-2-yl |
| 4.084 | 5-ethylimidazol-2-yl |
| 4.085 | 2-furyl |
| 4.086 | 3-furyl |
| 4.087 | 5-methyl-2-furyl |
| 4.088 | 5-ethyl-2-furyl |
| 4.089 | 5-chloro-2-furyl |
| 4.090 | 5-cyano-2-furyl |
| 4.091 | 1-methyltetrazol-5-yl |
| 4.092 | 3,4-dihydro-2H-pyrrol-5-yl |
| 4.093 | 2-oxo-3,4-dihydropyrrol-5-yl |
| 4.094 | 1H-pyrolidin-3-yl |
| 4.095 | 1-acyl-pyrolidin-4-yl |
| 4.096 | tetrahydrofuran-3-yl |
| 4.097 | tetrahydrofuran-2-yl |
| 4.098 | 2-methyl-1,2,4-triazol-3-yl |
| 4.099 | 2-ethyl-1,2,4-triazol-3-yl |
| 4.100 | 3-methyl-1,2,4-oxadiazol-5-yl |
| 4.101 | 3-ethyl-1,2,4-oxadiazol-5-yl |
| 4.102 | 2-thienyl |
| 4.103 | 3-thienyl |
| 4.104 | 5-methyl-2-thienyl |
| 4.105 | 5-ethyl-2-thienyl |
| 4.106 | 5-chloro-2-thienyl |
| 4.107 | 5-cyano-2-thienyl |
| 4.108 | oxazol-2-yl |
| 4.109 | oxazol-4-yl |
| 4.110 | oxazol-5-yl |
| 4.111 | 4-methyloxazol-2-yl |
| 4.112 | 5-methyloxazol-2-yl |
| 4.113 | 4-ethyloxazol-2-yl |
| 4.114 | 5-ethyloxazol-2-yl |
| 4.115 | 2-methyloxazol-4-yl |
| 4.116 | 2-ethyloxazol-4-yl |
| 4.117 | cyclopropyl |
| 4.118 | cyclobutyl |
| 4.119 | cyclopentyl |
| 4.120 | cyclohexyl |
| 4.121 | methyl |
| 4.122 | ethyl |
| 4.123 | propyl |
| 4.124 | isopropyl |
| 4.125 | butyl |
| 4.126 | isobutyl |
| 4.127 | sec-butyl |
| 4.128 | pentyl |
| 4.129 | prop-2-en-1-yl |
| 4.130 | prop-2-yn-1-yl |
| 4.131 | 2-methoxyethyl |
| 4.132 | 2-ethoxyethyl |
| 4.133 | 2-isopropyloxyethyl |
| 4.134 | but-2-ynl |
| 4.135 | propyn-2-ynl |
| 4.136 | pentyn-2-ynl |
| 4.137 | isoxazol-5-yl |
| 4.138 | isoxazol-4-yl |
| 4.139 | isoxazol-3-yl |

Each of Tables 4.2a to 4.5a (which follow Table 4.1a) make available 139 individual compounds of Formula (I-4a) wherein n, A¹, A², A³, A⁴, R¹ and R² are as specifically defined in Tables 4.2a to 4.5a, which refer to Table 4 wherein R⁵ is specifically defined.

Table 4.2a: This table discloses 139 specific compounds of Formula (I-4a) wherein n is 0, A², A³, A⁴, R¹ and R² are hydrogen, A¹ is fluorine, and Z is —C(=W)—R⁵, wherein W is O and R⁵ is as defined above in Table 4.

Table 4.3a: This table discloses 139 specific compounds of Formula (I-4a) wherein n is 0, A¹, A², A⁴, and R² are hydrogen, A³ is fluorine, and Z is —C(=W)—R⁵, wherein W is O and R⁵ is as defined above in Table 4.

Table 4.4a: This table discloses 139 specific compounds of Formula (I-4a) wherein n is 0, A², A⁴, R¹ and R² are hydrogen, A¹ and A³ are fluorine, and Z is —C(=W)—R⁵, wherein W is O and R⁵ is as defined above in Table 4.

Table 4.5a: This table discloses 139 specific compounds of Formula (I-4a) wherein n is 0, A³, A⁴, R¹ and R² are hydrogen, A¹ and A² are fluorine, and Z is —C(=W)—R⁵, wherein W is O and R⁵ is as defined above in Table 4.

Table 4.1b: This table discloses 139 specific compounds of Formula (I-4b):

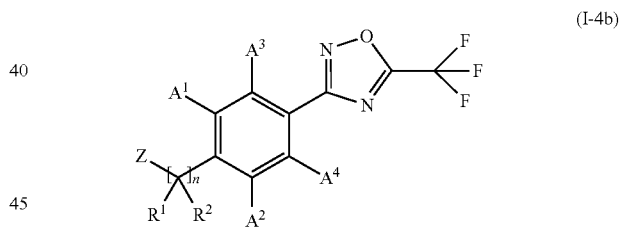

(I-4b)

wherein n is 1, A¹, A², A³, A⁴ and R¹ are hydrogen, R² is hydroxy and Z is R⁵, wherein R⁵ is as defined above in Table 4.

Each of Tables 4.2b to 4.5b (which follow Table 4.1b) make available 139 individual compounds of Formula (I-4b) wherein n, A¹, A², A³, A⁴, R¹ and R² are as specifically defined in Tables 4.2b to 4.5b, which refer to Table 4 wherein R⁵ is specifically defined.

Table 4.2b: This table discloses 139 specific compounds of Formula (I-4b) wherein n is 1, A², A³, A⁴ and R¹ are hydrogen, R² is hydroxy, A¹ is fluorine, and Z is R⁵ as defined above in Table 4.

Table 4.3b: This table discloses 139 specific compounds of Formula (I-4b) wherein n is 1, A¹, A², A⁴ and R¹ are hydrogen, R² is hydroxy, A³ is fluorine, and Z is R⁵ as defined above in Table 4.

Table 4.4b: This table discloses 139 specific compounds of Formula (I-4b) wherein n is 1, A², A⁴ and R¹ are hydrogen, R² is hydroxy, A¹ and A³ are fluorine, and Z is R⁵ as defined above in Table 4.

Table 4.5b: This table discloses 139 specific compounds of Formula (I-4b) wherein n is 1, $A^3$, $A^4$ and $R^1$ are hydrogen, $R^2$ is hydroxy, $A^1$ and $A^2$ are fluorine, and Z is $R^5$ as defined above in Table 4.

Table 4.6b: This table discloses a specific compound of Formula (I-4b) wherein n is 1, $A^1$, $A^2$, $A^3$, $A^4$ and $R^1$ are hydrogen, $R^2$ is hydroxy and Z is 5-methylpyrazin-2-yl.

Table 5.1: This table discloses 40 specific compounds of Formula (I-5):

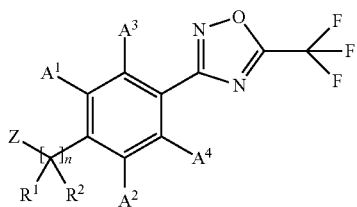

(I-5)

wherein n is 0, $A^1$, $A^2$, $A^3$, $A^4$, $R^1$ and $R^2$ are hydrogen, and Z is —C(=O)—C(=O)—$NR^3R^4$, wherein $R^3$ is hydrogen and $R^4$ is as defined below in Table 5.

TABLE 5

| Compound No. | $R^4$ |
|---|---|
| 5.001 | methyl |
| 5.002 | ethyl |
| 5.003 | propyl |
| 5.004 | isopropyl |
| 5.005 | butyl |
| 5.006 | 2-methoxyethyl |
| 5.007 | allyl |
| 5.008 | prop-2-ynyl |
| 5.009 | cyclopropyl |
| 5.010 | cyclopropylmethyl |
| 5.011 | 2-acetamidoethyl |
| 5.012 | 2-dimethylaminoethyl |
| 5.013 | 2-ethyl-3-oxo-isoxazolidin-4-yl |
| 5.014 | 2-fluoroethyl |
| 5.015 | 2-methylsulfanylethyl |
| 5.016 | hydrogen |
| 5.017 | 2,2-difluorocyclopentyl |
| 5.018 | 2-methoxy-2-oxo-ethyl |
| 5.019 | prop-2-ynoxy |
| 5.020 | prop-2-ynyl |
| 5.021 | 6-methoxy-2-pyridyl |
| 5.022 | cyanomethyl |
| 5.023 | oxetan-3-yl |
| 5.024 | 2,2-dimethylhydrazino |
| 5.025 | (2-fluorophenyl)methyl |
| 5.026 | (acetamido)methyl |
| 5.027 | acetonyl |
| 5.028 | allyloxy |
| 5.029 | benzyloxy |
| 5.030 | methoxy |
| 5.031 | ethoxy |
| 5.032 | phenyl |
| 5.033 | (3-methyl-2-thienyl)methyl |
| 5.034 | 2-(tert-butoxycarbonylamino)ethyl |
| 5.035 | 1,4-dioxan-2-ylmethyl |
| 5.036 | 2,2-difluoroethoxy |
| 5.037 | 2,2-difluoroethyl |
| 5.038 | 2,2-dimethoxyethyl |
| 5.039 | 2-(methylamino)-2-oxo-ethyl |
| 5.040 | isobutyl |

Each of Tables 5.2 to 5.5 (which follow Table 5.1) make available 40 individual compounds of Formula (I-5) wherein n, $A^1$, $A^2$, $A^3$, $A^4$, $R^1$ and $R^2$ are as specifically defined in Tables 5.2 to 5.5, which refer to Table 5 wherein $R^4$ is specifically defined.

Table 5.2: This table discloses 40 specific compounds of Formula (I-5) wherein $A^2$, $A^3$, $A^4$, $R^1$ and $R^2$ are hydrogen, $A^1$ is fluorine, and Z is —C(=O)—C(=O)—$NR^3R^4$, wherein $R^3$ is hydrogen and $R^4$ is as defined above in Table 5.

Table 5.3: This table discloses 40 specific compounds of Formula (I-5) wherein $A^1$, $A^2$, $A^4$, $R^1$ and $R^2$ are hydrogen, $A^3$ is fluorine, and Z is —C(=O)—C(=O)—$NR^3R^4$, wherein $R^3$ is hydrogen and $R^4$ is as defined above in Table 5.

Table 5.4: This table discloses 40 specific compounds of Formula (I-5) wherein $A^1$, $A^2$, $A^3$, $A^4$, $R^1$ and $R^2$ are hydrogen, and Z is —C(=O)—C(=O)—$NR^3R^4$, wherein $R^3$ is methyl and $R^4$ is as defined above in Table 5.

Table 5.5: This table discloses 40 specific compounds of Formula (I-5) wherein $A^1$, $A^2$, $A^3$, $A^4$, $R^1$ and $R^2$ are hydrogen, and Z is —C(=O)—C(=O)—$NR^3R^4$, wherein $R^3$ is methoxy and $R^4$ is as defined above in Table 5.

Table 6.1: This table discloses 149 specific compounds of Formula (I-6):

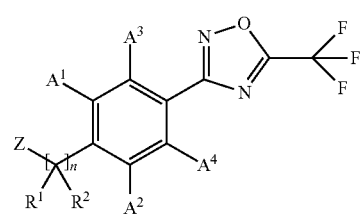

(I-6)

wherein n is 1, $A^1$, $A^2$, $A^3$, $A^4$, $R^1$ and $R^2$ are hydrogen, and Z is —$NR^3$—C(=W)—X, wherein $R^3$ is methyl, W is O and X is as defined below in Table 6.

TABLE 6

| Compound no. | X |
|---|---|
| 6.001 | methyl |
| 6.002 | ethyl |
| 6.003 | propyl |
| 6.004 | isopropyl |
| 6.005 | butyl |
| 6.006 | sec-butyl |
| 6.007 | 2-methylbutyl |
| 6.008 | tert-butyl |
| 6.009 | isobutyl |
| 6.010 | pentyl |
| 6.011 | 1-ethylpropyl |
| 6.012 | 2-ethylbutyl |
| 6.013 | 2,2-dimethylpropyl |
| 6.014 | 1,1-dimethylbutyl |
| 6.015 | 2,2-dimethylbutyl |
| 6.016 | 1-ethyl-1-methylpropyl |
| 6.017 | but-2-enyl |
| 6.018 | 2-methylpropenyl |
| 6.019 | ethenyl |
| 6.020 | propen-2-yl |
| 6.021 | allyl |
| 6.022 | 1-methylallyl |
| 6.023 | 2-methylallyl |
| 6.024 | 1,1-dimethylallyl |
| 6.025 | 1-methylprop-1-enyl |
| 6.026 | but-1-enyl |
| 6.027 | 3-methylbut-2-enyl |
| 6.028 | (E)-1,1-dimethylbut-2-enyl |
| 6.029 | but-3-enyl |
| 6.030 | prop-2-ynyl |
| 6.031 | but-3-ynyl |
| 6.032 | but-2-ynyl |

TABLE 6-continued

| Compound no. | X |
|---|---|
| 6.033 | 1-methylprop-2-ynyl |
| 6.034 | 1-methylbut-2-ynyl |
| 6.035 | 1,1-dimethylprop-2-ynyl |
| 6.036 | cyanomethyl |
| 6.037 | 2-cyanoethyl |
| 6.038 | 3-cyanopropyl |
| 6.039 | 1-ethoxymethyl |
| 6.040 | 1-methoxymethyl |
| 6.041 | difluoromethoxymethyl |
| 6.042 | 1-difluoromethoxyethyl |
| 6.043 | 1-methoxyethyl |
| 6.044 | 1-methoxyisopropyl |
| 6.045 | 1-ethyloxyisopropyl |
| 6.046 | 1-difluoromethoxyisopropyl |
| 6.047 | 2-methoxyethyl |
| 6.048 | 2-(difluoromethoxy)ethyl |
| 6.049 | 3-methoxypropyl |
| 6.050 | 4-methoxybutyl |
| 6.051 | 2-ethoxyethyl |
| 6.052 | 1-ethoxyethyl |
| 6.053 | 2-methoxypropyl |
| 6.054 | 1-(methoxymethyl)propyl |
| 6.055 | 2-methoxy-1,1-dimethyl-ethyl |
| 6.056 | 2-methoxyethoxymethyl |
| 6.057 | 1-acetoxymethyl |
| 6.058 | 2-acetoxyethyl |
| 6.059 | 2-acetoxy-1,1-dimethyl-ethyl |
| 6.060 | 2,2-diethoxyethyl |
| 6.061 | 2,2-dimethoxyethyl |
| 6.062 | hydroxymethyl |
| 6.063 | 1-hydroxyethyl |
| 6.064 | 1-hydroxyisopropyl |
| 6.065 | 2-hydroxyethyl |
| 6.066 | 2-hydroxypropyl |
| 6.067 | 3-hydroxypropyl |
| 6.068 | 2-hydroxy-1,1-dimethyl-ethyl |
| 6.069 | 2-hydroxy-2-methyl-propyl |
| 6.070 | trifluoromethyl |
| 6.071 | 2,2,2-trifluoroethyl |
| 6.072 | 3,3,3-trifluoropropyl |
| 6.073 | 4,4,4-trifluorobutyl |
| 6.074 | fluoromethyl |
| 6.075 | difluoromethyl |
| 6.076 | 2-fluoroethyl |
| 6.077 | 1-fluoroethyl |
| 6.078 | chloromethyl |
| 6.079 | 2-chloroethyl |
| 6.080 | 2-chloro-1,1-dimethylethyl |
| 6.081 | 2-(methylamino)-2-oxo-ethyl |
| 6.082 | 2-(ethylamino)-2-oxo-ethyl |
| 6.083 | 2-(tert-butylamino)-2-oxo-ethyl |
| 6.084 | 2-(isopropylamino)-2-oxo-ethyl |
| 6.085 | acetamidomethyl |
| 6.086 | acetamidoethyl |
| 6.087 | 1-methyl-3-oxo-butyl |
| 6.088 | 3-methoxy-1-methyl-3-oxo-propyl |
| 6.089 | 3-methoxy-3-oxo-propyl |
| 6.090 | phenyl |
| 6.091 | 2-chlorophenyl |
| 6.092 | 2-fluorophenyl |
| 6.093 | 3-fluorophenyl |
| 6.094 | 4-fluorophenyl |
| 6.095 | 3,5-difluorophenyl |
| 6.096 | 4-pyrimidinyl |
| 6.097 | thiazol-5-yl |
| 6.098 | oxazol-5-yl |
| 6.099 | isoxazol-3-yl |
| 6.100 | 2-pyridyl |
| 6.101 | benzyl |
| 6.102 | 3-chlorophenylmethyl |
| 6.103 | 3-fluorophenylmethyl |
| 6.104 | 2-pyridylmethyl |
| 6.105 | cyclopentyl |
| 6.106 | cyclohexyl |
| 6.107 | cyclopentylmethyl |
| 6.108 | cyclohexylmethyl |
| 6.109 | cyclopropylmethyl |
| 6.110 | cyclopropyl |
| 6.111 | 1-chlorocycloprop-1-yl |
| 6.112 | 1-cyanocycloprop-1-yl |
| 6.113 | 1-fluorocycloprop-1-yl |
| 6.114 | 1-methylcyclopropyl |
| 6.115 | 1-trifluoromethylcycloprop-1-yl |
| 6.116 | 2-cyanocyclopropyl |
| 6.117 | 2-fluorocyclopropyl |
| 6.118 | 2-methylcyclopropyl |
| 6.119 | 2,2-dichlorocyclopropyl |
| 6.120 | 2,2-difluorocyclopropyl |
| 6.121 | 2,2-dimethylcyclopropyl |
| 6.122 | 2,2,3,3-tetramethylcyclopropyl |
| 6.123 | 2,2-dichloro-1-methyl-cyclopropyl |
| 6.124 | cyclobutyl |
| 6.125 | 1-methylcyclobutyl |
| 6.126 | 1-(trifluoromethyl)cyclobutyl |
| 6.127 | 1-cyanocyclobut-1-yl |
| 6.128 | cyclobutylmethyl |
| 6.129 | 2,2-difluorocyclopropylmethyl |
| 6.130 | tetrahydrothiopyran-2-yl |
| 6.131 | tetrahydrothiopyran-3-yl |
| 6.132 | tetrahydrothiopyran-4-yl |
| 6.133 | oxetan-3-yl |
| 6.134 | 3-cyanooxetan-3-yl |
| 6.135 | 3-methyloxetan-3-yl |
| 6.136 | 3-trifluoromethyloxetan-3-yl |
| 6.137 | oxetan-2-yl |
| 6.138 | oxetan-3-ylmethyl |
| 6.139 | oxetan-2-ylmethyl |
| 6.140 | tetrahydrofuran-2-yl |
| 6.141 | tetrahydrofuran-3-yl |
| 6.142 | tetrahydrofuran-2-ylmethyl |
| 6.143 | tetrahydropyran-2-yl |
| 6.144 | tetrahydropyran-3-yl |
| 6.145 | tetrahydropyran-4-yl |
| 6.146 | 2-methyl-1,3-dioxolan-2-yl |
| 6.147 | 1,3-dioxolan-2-yl |
| 6.148 | 1-acetylpyrrolidin-2-yl |
| 6.149 | 1-imidazoyl |

Each of Tables 6.2 to 6.11 (which follow Table 6.1) make available 149 individual compounds of Formula (I-6) wherein n, $A^1$, $A^2$, $A^3$, $A^4$, $R^1$ and $R^2$ are as specifically defined in Tables 6.2 to 6.11, which refer to Table 6 wherein X is specifically defined.

Table 6.2: This table discloses 149 specific compounds of Formula (I-6) wherein n is 1, $A^1$, $A^2$, $A^3$, $A^4$, $R^1$ and $R^2$ are hydrogen, and Z is —NR$^3$—C(=W)—X, wherein $R^3$ is ethyl, W is O and X is as defined above in Table 6.

Table 6.3: This table discloses 149 specific compounds of Formula (I-6) wherein n is 1, $A^1$, $A^2$, $A^3$, $A^4$, $R^1$ and $R^2$ are hydrogen, and Z is —NR$^3$—C(=W)—X, wherein $R^3$ is i-propyl, W is O and X is as defined above in Table 6.

Table 6.4: This table discloses 149 specific compounds of Formula (I-6) wherein n is 1, $A^1$, $A^2$, $A^3$, $A^4$, $R^1$ and $R^2$ are hydrogen, and Z is —NR$^3$—C(=W)—X, wherein $R^3$ is cyclopropyl, W is O and X is as defined above in Table 6.

Table 6.5: This table discloses 149 specific compounds of Formula (I-6) wherein n is 1, $A^1$, $A^2$, $A^3$, $A^4$, $R^1$ and $R^2$ are hydrogen, and Z is —NR$^3$—C(=W)—X, wherein $R^3$ is 2-methoxyethyl, W is O and X is as defined above in Table 6.

Table 6.6: This table discloses 149 specific compounds of Formula (I-6) wherein n is 1, $A^1$, $A^2$, $A^3$, $A^4$, $R^1$ and $R^2$ are hydrogen, and Z is —NR$^3$—C(=W)—X, wherein $R^3$ is 2,2,2-trifluoroethyl, W is O and X is as defined above in Table 6.

Table 6.7: This table discloses 149 specific compounds of Formula (I-6) wherein n is 1, $A^1$, $A^2$, $A^3$, $A^4$, $R^1$ and $R^2$ are hydrogen, and Z is —NR³—C(=W)—X, wherein R³ is methoxy, W is O and X is as defined above in Table 6.

Table 6.8: This table discloses 149 specific compounds of Formula (I-6) wherein n is 1, A², A³, A⁴, R¹ and R² are hydrogen, A¹ is fluorine, and Z is —NR³—C(=W)—X, wherein R³ is methoxy, W is O and X is as defined above in Table 6.

Table 6.9: This table discloses 149 specific compounds of Formula (I-6) wherein n is 1, A¹, A², A⁴, R¹ and R² are hydrogen, A³ is fluorine, and Z is —NR³—C(=W)—X, wherein R³ is methoxy, W is O and X is as defined above in Table 6.

Table 6.10: This table discloses 149 specific compounds of Formula (I-6) wherein n is 1, A², A⁴, R¹ and R² are hydrogen, A¹ and A³ are fluorine, and Z is —NR³—C(=W)—X, wherein R³ is methoxy, W is O and X is as defined above in Table 6.

Table 6.11: This table discloses 149 specific compounds of Formula (I-6) wherein n is 1, A¹, A², A³, A⁴, R¹ and R² are hydrogen, and Z is —NR³—C(=W)—X, wherein R³ is ethoxy, W is O and X is as defined above in Table 6.

Table 7.1: This table discloses 100 specific compounds of Formula (I-7):

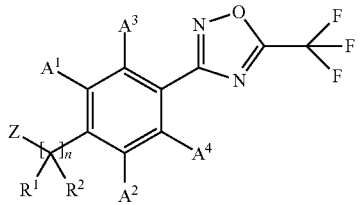

(I-7)

wherein n is 1, A¹, A², A³, A⁴, R¹ and R² are hydrogen, and Z is —NR³—C(=W)—NR³R⁴, wherein R³ is methyl, W is O and R⁴ is as defined below in Table 7.

TABLE 7

| Compound no. | R⁴ |
|---|---|
| 7.001 | methyl |
| 7.002 | ethyl |
| 7.003 | propyl |
| 7.004 | isopropyl |
| 7.005 | butyl |
| 7.006 | sec-butyl |
| 7.007 | tert-butyl |
| 7.008 | isobutyl |
| 7.009 | pentyl |
| 7.010 | allyl |
| 7.011 | 2-methylallyl |
| 7.012 | 1,1-dimethylallyl |
| 7.013 | prop-2-ynyl |
| 7.014 | 2-acetoxyethyl |
| 7.015 | 2-hydroxyethyl |
| 7.016 | 2-hydroxypropyl |
| 7.017 | 3-hydroxypropyl |
| 7.018 | 2,2-difluoroethyl |
| 7.019 | 2,2,2-trifluoroethyl |
| 7.020 | 3,3,3-trifluoropropyl |
| 7.021 | 4,4,4-trifluorobutyl |
| 7.022 | but-3-ynyl |
| 7.023 | but-2-ynyl |
| 7.024 | 2-cyanoethyl |
| 7.025 | 2-methoxyethyl |
| 7.026 | 2-ethoxyethyl |
| 7.027 | 2-methoxypropyl |
| 7.028 | 1-methoxy-4-piperidyl |

TABLE 7-continued

| Compound no. | R⁴ |
|---|---|
| 7.029 | oxetan-3-yl |
| 7.030 | phenyl |
| 7.031 | pyrid-2-yl |
| 7.032 | pyrid-3-yl |
| 7.033 | pyrid-4-yl |
| 7.034 | phenylmethyl |
| 7.035 | pyrid-2-ylmethyl |
| 7.036 | cyclopropyl |
| 7.037 | 1-cyanocyclopropyl |
| 7.038 | 1-fluorocyclopropyl |
| 7.039 | 1-methylcyclopropyl |
| 7.040 | cyclobutyl |
| 7.041 | cyclopentyl |
| 7.042 | cyclohexyl |
| 7.043 | cyclopropylmethyl |
| 7.044 | cyclobutylmethyl |
| 7.045 | cyclopentylmethyl |
| 7.046 | cyclohexylmethyl |
| 7.047 | tetrahydrofuran-3-yl |
| 7.048 | tetrahydropyran-3-yl |
| 7.049 | tetrahydropyran-4-yl |
| 7.050 | tetrahydrofuran-2-ylmethyl |
| 7.051 | tetrahydrofuran-3-ylmethyl |
| 7.052 | tetrahydropyran-2-ylmethyl |
| 7.053 | tetrahydropyran-3-ylmethyl |
| 7.054 | benzyl |
| 7.055 | furylmethyl |
| 7.056 | 1-methoxymethylcyclopropyl |
| 7.057 | 1-ethoxycarbonylcyclopropyl |
| 7.058 | 1-hydroxycyclopropylmethyl |
| 7.059 | cyclopropyl-1-ethyl |
| 7.060 | 2,2-dimethylpropyl |
| 7.061 | cyano |
| 7.062 | 1-methylprop-2-ynyl |
| 7.063 | 1-methylbut-2-ynyl |
| 7.064 | 1,1-dimethylprop-2-ynyl |
| 7.065 | cyanomethyl |
| 7.066 | 2-cyanoethyl |
| 7.067 | 3-cyanopropyl |
| 7.068 | 1-methoxymethyl |
| 7.069 | 2-methoxyethyl |
| 7.070 | 3-methoxypropyl |
| 7.071 | 4-methoxybutyl |
| 7.072 | 1-methoxyethyl |
| 7.073 | 1-(methoxymethyl)propyl |
| 7.074 | 2-methoxy-1,1-dimethylethyl |
| 7.075 | 2-methoxyethoxymethyl |
| 7.076 | 1-acetoxymethyl |
| 7.077 | 2-acetoxy-1,1-dimethylethyl |
| 7.078 | 2,2-diethoxyethyl |
| 7.079 | 2,2-dimethoxyethyl |
| 7.080 | hydroxymethyl |
| 7.081 | 2-hydroxypropyl |
| 7.082 | 2-hydroxy-1,1-dimethylethyl |
| 7.083 | 2-hydroxy-2-methylpropyl |
| 7.084 | trifluoromethyl |
| 7.085 | fluoromethyl |
| 7.086 | difluoromethyl |
| 7.087 | 2-fluoroethyl |
| 7.088 | 2-chloroethyl |
| 7.089 | 3-chloropropyl |
| 7.090 | methoxy |
| 7.091 | ethoxy |
| 7.092 | propoxy |
| 7.093 | isopropoxy |
| 7.094 | butoxy |
| 7.095 | sec-butoxy |
| 7.096 | isobutoxy |
| 7.097 | allyloxy |
| 7.098 | prop-2-ynyloxy |
| 7.099 | ethoxycarbonylmethyl |
| 7.100 | methylaminocarbonylmethyl |

Each of Tables 7.2 to 7.7 (which follow Table 7.1) make available 100 individual compounds of Formula (I-7)

wherein n, $A^1$, $A^2$, $A^3$, $A^4$, $R^1$, $R^2$ and $R^3$ are as specifically defined in Tables 7.2 to 7.7, which refer to Table 7 wherein $R^4$ is specifically defined.

Table 7.2: This table discloses 100 specific compounds of Formula (I-7) wherein n is 1, $A^1$, $A^2$, $A^3$, $A^4$, $R^1$ and $R^2$ are hydrogen, and Z is —$NR^3$—C(=W)—$NR^3R^4$, wherein $R^3$ is ethyl, W is O and $R^4$ is as defined above in Table 7.

Table 7.3: This table discloses 100 specific compounds of Formula (I-7) wherein n is 1, $A^1$, $A^2$, $A^3$, $A^4$, $R^1$ and $R^2$ are hydrogen, and Z is —$NR^3$—C(=W)—$NR^3R^4$, wherein $R^3$ is i-propyl, W is O and $R^4$ is as defined above in Table 7.

Table 7.4: This table discloses 100 specific compounds of Formula (I-7) wherein n is 1, $A^1$, $A^2$, $A^3$, $A^4$, $R^1$ and $R^2$ are hydrogen, and Z is —$NR^3$—C(=W)—$NR^3R^4$, wherein $R^3$ is cyclopropyl, W is O and $R^4$ is as defined above in Table 7.

Table 7.5: This table discloses 100 specific compounds of Formula (I-7) wherein n is 1, $A^1$, $A^2$, $A^3$, $A^4$, $R^1$ and $R^2$ are hydrogen, and Z is —$NR^3$—C(=W)—$NR^3R^4$, wherein $R^3$ is methoxy, W is O and $R^4$ is as defined above in Table 7.

Table 7.6: This table discloses 100 specific compounds of Formula (I-7) wherein n is 1, $A^2$, $A^3$, $A^4$, $R^1$ and $R^2$ are hydrogen, $A^1$ is fluorine, and Z is —$NR^3$—C(=W)—$NR^3R^4$, wherein $R^3$ is methoxy, W is O and $R^4$ is as defined above in Table 7.

Table 7.7: This table discloses 100 specific compounds of Formula (I-7) wherein n is 1, $A^1$, $A^2$, $A^4$, $R^1$ and $R^2$ are hydrogen, $A^3$ is fluorine, and Z is —$NR^3$—C(=W)—$NR^3R^4$, wherein $R^3$ is methoxy, W is O and $R^4$ is as defined above in Table 7.

Table 8.1: This table discloses 107 specific compounds of Formula (I-8):

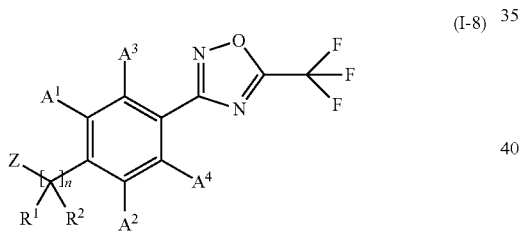

(I-8)

wherein n is 1, $A^1$, $A^2$, $A^3$, $A^4$, $R^1$ and $R^2$ are hydrogen, and Z is —$NR^3$—C(=W)—X, wherein $R^3$ is hydrogen, W is O and X is as defined below in Table 8.

TABLE 8

| Compound no. | $R^4$ |
|---|---|
| 8.001 | methyl |
| 8.002 | ethyl |
| 8.003 | propyl |
| 8.004 | isopropyl |
| 8.005 | butyl |
| 8.006 | sec-butyl |
| 8.007 | tert-butyl |
| 8.008 | isobutyl |
| 8.009 | pentyl |
| 8.010 | 1-ethylpropyl |
| 8.011 | 2-ethylbutyl |
| 8.012 | 2,2-dimethylpropyl |
| 8.013 | 1,1-dimethylbutyl |
| 8.014 | 2,2-dimethylbutyl |
| 8.015 | ethenyl |
| 8.016 | propen-2-yl |
| 8.017 | allyl |

TABLE 8-continued

| Compound no. | $R^4$ |
|---|---|
| 8.018 | (E)-but-2-enyl |
| 8.019 | 2-methylallyl |
| 8.020 | 1,1-dimethylallyl |
| 8.021 | 3-methylbut-2-enyl |
| 8.022 | (E)-1,1-dimethylbut-2-enyl |
| 8.023 | but-3-enyl |
| 8.024 | prop-2-ynyl |
| 8.025 | but-3-ynyl |
| 8.026 | but-2-ynyl |
| 8.027 | 1-methylprop-2-ynyl |
| 8.028 | 1-methylbut-2-ynyl |
| 8.029 | 1,1-dimethylprop-2-ynyl |
| 8.030 | cyanomethyl |
| 8.031 | 2-cyanoethyl |
| 8.032 | 3-cyanopropyl |
| 8.033 | 1-methoxymethyl |
| 8.034 | 2-methoxyethyl |
| 8.035 | 3-methoxypropyl |
| 8.036 | 4-methoxybutyl |
| 8.037 | 2-ethoxyethyl |
| 8.038 | 1-methoxyethyl |
| 8.039 | 2-methoxypropyl |
| 8.040 | 1-(methoxymethyl)propyl |
| 8.041 | 2-methoxy-1,1-dimethyl-ethyl |
| 8.042 | 2-methoxyethoxymethyl |
| 8.043 | 1-acetoxymethyl |
| 8.044 | 2-acetoxyethyl |
| 8.045 | 2-acetoxy-1,1-dimethyl-ethyl |
| 8.046 | 2,2-diethoxyethyl |
| 8.047 | 2,2-dimethoxyethyl |
| 8.048 | hydroxymethyl |
| 8.049 | 2-hydroxyethyl |
| 8.050 | 2-hydroxypropyl |
| 8.051 | 3-hydroxypropyl |
| 8.052 | 2-hydroxy-1,1-dimethyl-ethyl |
| 8.053 | 2-hydroxy-2-methyl-propyl |
| 8.054 | trifluoromethyl |
| 8.055 | 2,2,2-trifluoroethyl |
| 8.056 | 3,3,3-trifluoropropyl |
| 8.057 | 4,4,4-trifluorobutyl |
| 8.058 | fluoromethyl |
| 8.059 | difluoromethyl |
| 8.060 | 2-fluoroethyl |
| 8.061 | 3-fluoropropyl |
| 8.062 | 4-fluorobutyl |
| 8.063 | 1-fluoroethyl |
| 8.064 | 2-fluoropropyl |
| 8.065 | chloromethyl |
| 8.066 | 2-chloroethyl |
| 8.067 | methylsulfanylmethyl |
| 8.068 | methylsulfonylmethyl |
| 8.069 | 2-methylsulfanylethyl |
| 8.070 | 2-methylsulfonylethyl |
| 8.071 | methanesulfonamidomethyl |
| 8.072 | methanesulfonamidoethyl |
| 8.073 | 2-(methylamino)-2-oxo-ethyl |
| 8.074 | 2-(ethylamino)-2-oxo-ethyl |
| 8.075 | acetamidomethyl |
| 8.076 | acetamidoethyl |
| 8.077 | 1-methyl-3-oxo-butyl |
| 8.078 | 3-methoxy-1-methyl-3-oxo-propyl |
| 8.079 | 3-methoxy-3-oxo-propyl |
| 8.080 | 1-hydroxyethyl |
| 8.081 | difluoromethoxymethyl |
| 8.082 | 1-difluoromethoxyethyl |
| 8.083 | 2-difluoromethoxyethyl |
| 8.084 | prop-2-enyl |
| 8.085 | but-2-enyl |
| 8.086 | 5,5,5-trifluoropentyl |
| 8.087 | 2-methylpropenyl |
| 8.088 | 2-methylbutyl |
| 8.089 | 2-methoxy-1,1-dimethylethyl |
| 8.090 | 2-hydroxy-2-methylpropyl |
| 8.091 | 2-hydroxy-1,1-dimethylethyl |
| 8.092 | 2-chloro-1,1-dimethylethyl |
| 8.093 | 2-acetoxy-1,1-dimethylethyl |
| 8.094 | 2-(trifluoromethyl)butyl |

TABLE 8-continued

| Compound no. | R⁴ |
|---|---|
| 8.095 | 2-(difluoromethoxy)methyl |
| 8.096 | 2-(difluoromethoxy)ethyl |
| 8.097 | 1-methyoxymethyl |
| 8.098 | 1-methylpropyl |
| 8.099 | 1-methylallyl |
| 8.100 | 1-hydroxymethyl |
| 8.101 | 1-hydroxy-1-methylethyl |
| 8.102 | 1-ethyl-1-methylpropyl |
| 8.103 | 1-cyanomethyl |
| 8.104 | 1-acetamidomethyl |
| 8.105 | 1-(chloromethyl)-2-hydroxy-1-methylethyl |
| 8.106 | (E)-but-1-enyl |
| 8.107 | (E)-1-methylprop-1-enyl |

Each of Tables 8.2 to 8.4 (which follow Table 8.1) make available 107 individual compounds of Formula (I-8) wherein n, $A^1$, $A^2$, $A^3$, $A^4$, $R^1$, $R^2$ and $R^3$ are as specifically defined in Tables 8.2 to 8.4, which refer to Table 8 wherein $R^4$ is specifically defined.

Table 8.2: This table discloses 107 specific compounds of Formula (I-8) wherein n is 1, $A^2$, $A^3$, $A^4$, $R^1$ and $R^2$ are hydrogen, $A^1$ is fluorine, and Z is —$NR^3$—C(=W)—X, wherein $R^3$ is hydrogen, W is O and X is as defined above in Table 8.

Table 8.3: This table discloses 107 specific compounds of Formula (I-8) wherein n is 1, $A^1$, $A^2$, $A^4$, $R^1$ and $R^2$ are hydrogen, $A^3$ is fluorine, and Z is —$NR^3$—C(=W)—X, wherein $R^3$ is hydrogen, W is O and X is as defined above in Table 8.

Table 8.4: This table discloses 107 specific compounds of Formula (I-8) wherein n is 1, $A^2$, $A^4$, $R^1$ and $R^2$ are hydrogen, $A^1$ and $A^3$ are fluorine, and Z is —$NR^3$—C(=W)—X, wherein $R^3$ is hydrogen, W is O and X is as defined above in Table 8.

Table 9.1: This table discloses 36 specific compounds of Formula (I-9):

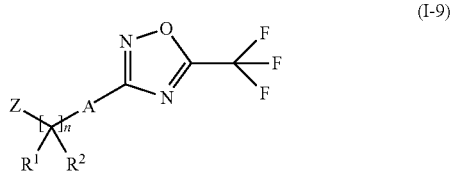

(I-9)

wherein n is 1, A is A-1, $R^1$ is hydrogen, $R^2$ is methoxy and Z is —C(=O)—$NR^3R^4$, wherein —$NR^3R^4$ is as defined below in Table 9.

TABLE 9

| Compound no. | —NR³R⁴ |
|---|---|
| 9.001 | N-methylamino |
| 9.002 | N-ethylamino |
| 9.003 | N-propylamino |
| 9.004 | N-isopropylamino |
| 9.005 | N-methoxyamino |
| 9.006 | N-ethoxyamino |
| 9.007 | N-methyl-N-methoxyamino |
| 9.008 | N-methyl-N-propyn-2-ylamino |
| 9.009 | N-methyl-N-3,3,3-trifluoromethylamino |
| 9.010 | N,N-dimethylamino |
| 9.011 | N-ethyl-N-methylamino |
| 9.012 | cyclopropylamino |

TABLE 9-continued

| Compound no. | —NR³R⁴ |
|---|---|
| 9.013 | cyclopropylmethylamino |
| 9.014 | N-2-methoxyethyl-N-methylamino |
| 9.015 | N-propen-2-ylamino |
| 9.016 | N-propyn-2-ylamino |
| 9.017 | pyrolidinyl |
| 9.018 | piperidinyl |
| 9.019 | N-oxetan-3-yl-N-methoxyamino |
| 9.020 | N-cyclopropylmethyl-N-methylamino |
| 9.021 | N-1-cyclopropylethyl-N-methylamino |
| 9.022 | azetidinyl |
| 9.023 | N-[2-(dimethylamino)ethyl]-N-methylamino |
| 9.024 | N-(2-cyanoethyl)-N-ethylamino |
| 9.025 | N-(cyclopropylmethyl)-N-propylamino |
| 9.026 | N,N-(di-2-methoxyethyl)amino |
| 9.027 | N-methyl-N-cyanomethylamino |
| 9.028 | N-methyl-N-prop-2-enylamino |
| 9.029 | N,N-diethylamino |
| 9.030 | isoxazolidinyl |
| 9.031 | N,N-(di-prop-2-enyl)amino |
| 9.032 | N-cyclopropyl-N-(2,2-difluoroethyl)amino |
| 9.033 | N-ethoxy-N-isopropylamino |
| 9.034 | morpholinyl |
| 9.035 | amino |
| 9.036 | (N,N-di-methylamine)amino |

Each of Tables 9.2 to 9.4 (which follow Table 9.1) make available 36 individual compounds of the Formula (I-9) wherein n, A, $R^1$, $R^2$, $R^3$ and $R^4$ are as specifically defined in Tables 9.2 to 9.4, which refer to Table 9 wherein —$NR^3R^4$ is specifically defined.

Table 9.2: This table discloses 36 specific compounds of Formula (I-9) wherein n is 1, A is A-1, $R^1$ is hydrogen, $R^2$ is ethoxy, and Z is —C(=O)—$NR^3R^4$, wherein —$NR^3R^4$ is as defined above in Table 9.

Table 9.3: This table discloses 36 specific compounds of Formula (I-9) wherein n is 1, A is A-2, $R^1$ is hydrogen, $R^2$ is methoxy, and Z is —C(=O)—$NR^3R^4$, wherein —$NR^3R^4$ is as defined above in Table 9.

Table 9.4: This table discloses 36 specific compounds of Formula (I-9) wherein n is 1, A is A-2, $R^1$ is hydrogen, $R^2$ is ethoxy, and Z is —C(=O)—$NR^3R^4$, wherein —$NR^3R^4$ is as defined above in Table 9.

Table 10.1: This table discloses 37 specific compounds of Formula (I-10):

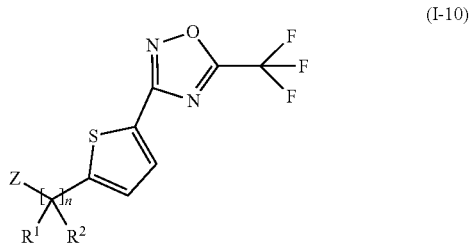

(I-10)

wherein n is 0, and Z is —C(=O)—$R^5$, wherein $R^5$ is as defined below in Table 10.

TABLE 10

| Compound No. | R⁵ |
|---|---|
| 10.001 | 2-thiazolyl |
| 10.002 | 4-thiazolyl |

TABLE 10-continued

| Compound No. | R⁵ |
| --- | --- |
| 10.003 | 5-thiazolyl |
| 10.004 | 4-methylthiazol-2-yl |
| 10.005 | 5-methylthiazol-2-yl |
| 10.006 | 4-ethylthiazol-2-yl |
| 10.007 | 5-ethylthiazol-2-yl |
| 10.008 | 2-methylthiazol-4-yl |
| 10.009 | 2-ethylthiazol-4-yl |
| 10.010 | 5-methylisoxazol-3-yl |
| 10.011 | 5-ethylisoxazol-3-yl |
| 10.012 | 5-isopropylisoxazol-3-yl |
| 10.013 | 3-methylisoxazol-5-yl |
| 10.014 | 3-ethylisoxazol-5-yl |
| 10.015 | 3-isopropylisoxazol-5-yl |
| 10.016 | 3-methylisothiazol-5-yl |
| 10.017 | 3-ethylisothiazol-5-yl |
| 10.018 | 2-methyl-1,2,4-triazol-3-yl |
| 10.019 | 2-ethyl-1,2,4-triazol-3-yl |
| 10.020 | 3-methyl-1,2,4-oxadiazol-5-yl |
| 10.021 | 3-ethyl-1,2,4-oxadiazol-5-yl |
| 10.022 | 3-cyano-1,2,4-oxadiazol-5-yl |
| 10.023 | 2-thienyl |
| 10.024 | 3-thienyl |
| 10.025 | 5-methyl-2-thienyl |
| 10.026 | 5-ethyl-2-thienyl |
| 10.027 | 5-chloro-2-thienyl |
| 10.028 | 5-cyano-2-thienyl |
| 10.029 | oxazol-2-yl |
| 10.030 | oxazol-4-yl |
| 10.031 | oxazol-5-yl |
| 10.032 | 4-methyloxazol-2-yl |
| 10.033 | 5-methyloxazol-2-yl |
| 10.034 | 4-ethyloxazol-2-yl |
| 10.035 | 5-ethyloxazol-2-yl |
| 10.036 | 2-methyloxazol-4-yl |
| 10.037 | 5-methylpyrazin-2-yl |

Table 10.2: This table discloses 37 specific compounds of Formula (I-10) wherein n is 1, $R^1$ is hydrogen, $R^2$ is hydroxy, and Z is $R^5$, wherein $R^5$ is as defined above in Table 10.

Table 10.3: This table discloses a specific compound of Formula (I-10) wherein n is 1, $R^1$ is hydrogen, $R^2$ is hydroxy, and Z is 5-methylpyrid-2-yl.

According to an embodiment of the process of the invention, a compound of Formula (I), wherein Z is $Z^1$, hereinafter referred to as compound of Formula (I-B), is advantageously used in the process for the preparation of a compound of Formula (I-A) to obtain valuable intermediates. Thus, the process of the invention may further comprise the step of reacting an intermediate compound of Formula (I-B), wherein Z is $Z^1$, to obtain a compound of Formula (I-A), wherein Z is $Z^2$.

Also, the present invention further relates to intermediate compounds of Formula (I-B), wherein Z is $Z^1$.

In particular, a compound of Formula (I-B), wherein $Z^1$ is hydrogen, can be reacted with a halogenating agent, optionally in the presence of a radical initiator such as dibenzoyl peroxide or azobisisobutyronitrile (AIBN), to obtain an intermediate compound of Formula (I-B), wherein $Z^1$ is a halogen, preferably Cl, Br or I.

Examples of suitable halogenating agents include, for instance, brominating agents such as bromine or N-bromosuccinimide. The reaction is typically carried out at a temperature from 55° C. to 100° C. For related examples, see WO 2017/055473; WO 2018/177894; Liu, S. et al Synthesis (2001), 14, 2078; and Kompella, A. et al Org. Proc. Res. Dev. (2012), 16, 1794.

Preferably, n in the compound of Formula (I-A) is 0 or 1.
Preferably, n in the compound of Formula (I-B) is 0 or 1.

The compound of Formula (I-A), wherein Z is $Z^2$, can be prepared from a compound of Formula (I-B) via reaction with a compound of Formula (IV), typically in the presence of a base. In some cases, a better reaction performance may be gained from the use of a catalyst (e.g., NaI or 4-dimethylaminopyridine) and with microwave irradiation. For related examples, see WO 2013/132253; and Garcia, M. et al Org. Biomol. Chem. (2004), 11, 1633. This reaction is shown in Scheme 3.

Scheme 3

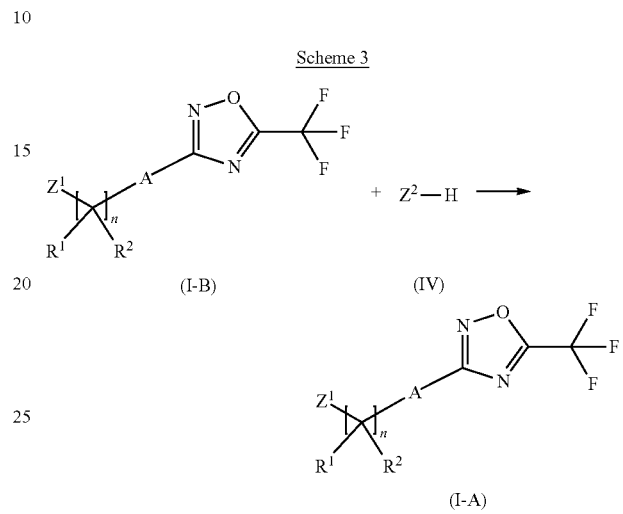

It has been found that the compound of Formula (I-B), wherein n is 1 and $Z^1$ is Br, is particularly reactive towards compounds of Formula (IV).

In one embodiment, the present invention relates to a process for the preparation of a compound of Formula (I-A), wherein $Z^2$ is —NR³—C(=W)—X:

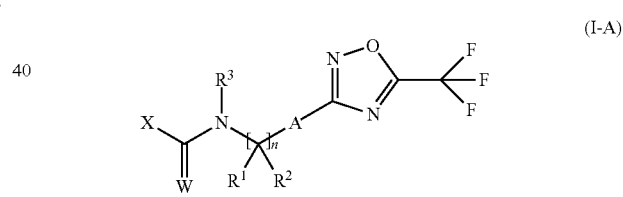

The compound of Formula (I-A), wherein $Z^2$ is preferably —NR³—C(=W)—X, can be prepared from a compound of Formula (I-B), wherein $Z^1$ is a halogen, via reaction with a compound of Formula (V) or a salt thereof, wherein $R^3$ is as defined above for a compound of Formula (I), to obtain a compound of Formula (I-a) or a salt thereof. For related examples, see Miyawaki, K. et al Heterocycles (2001), 54, 887; WO 2003/028729; WO 2017/055473; WO 2018/177894; and WO 2013/066839. This reaction is shown in Scheme 4.

Scheme 4

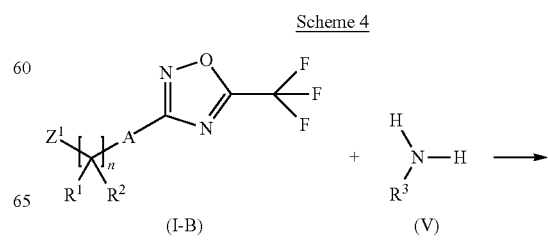

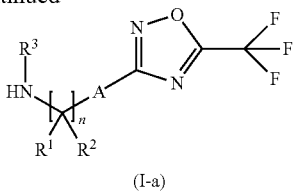

(I-a)

When $Z^1$ in the compound of Formula (I-B) is a halogen, it is preferably chlorine or bromine.

The compound of Formula (I-a) or a salt thereof can be further reacted with a compound of Formula (VI), wherein X and W are as defined above for a compound of Formula (I) and T is halogen, hydroxy or $C_{1-4}$alkoxy, to obtain a compound of Formula (I-A), wherein $Z^2$ is —$NR^3$—C(=W)—X. For related examples, see Nelson, T. D et al *Tetrahedron Lett*. (2004), 45, 8917; Senthil, K. et al *Pest. Res. Journal* (2009), 21, 133; Crich, D., Zou, Y. J. *Org. Chem*. (2005), 70, 3309; WO 2018/177894; and WO 2017/055473. This reaction is shown in Scheme 5.

Scheme 5

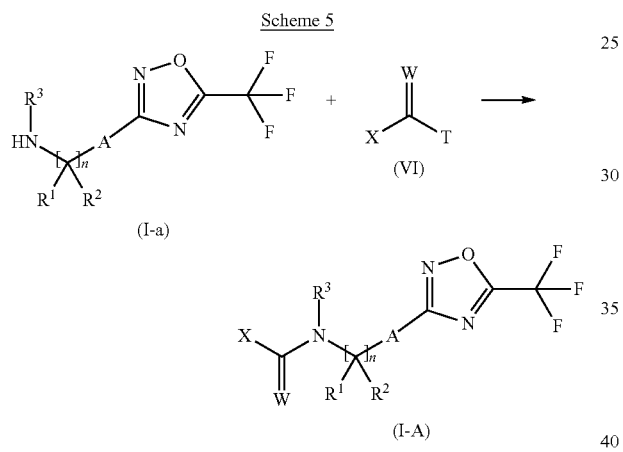

Additionally, the compound of Formula (I-A), wherein $Z^2$ is —$NR^3$—C(=W)—X, can be prepared according to the process of the invention from a compound of Formula (II), wherein Z is —$NR^3$—C(=W)—X, hereinafter referred to as compound of Formula (II-A), via reaction with a compound of Formula (III). This reaction is shown in Scheme 6.

Scheme 6

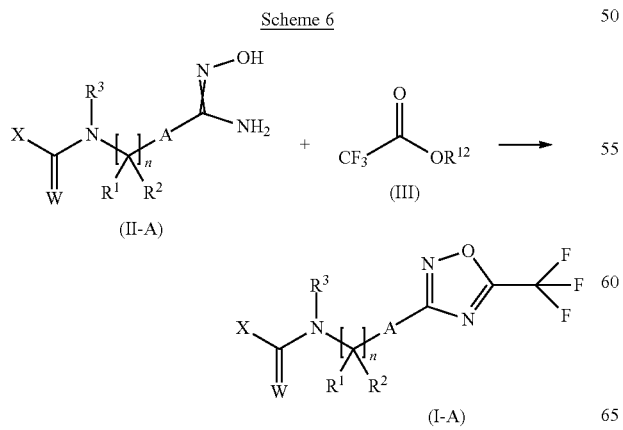

The compound of Formula (II) can be prepared from a compound of Formula (VII) via reaction with hydroxylamine or a salt thereof, such as hydroxylamine hydrochloride salt, optionally in the presence of one or more bases. This reaction is shown in Scheme 7.

Scheme 7

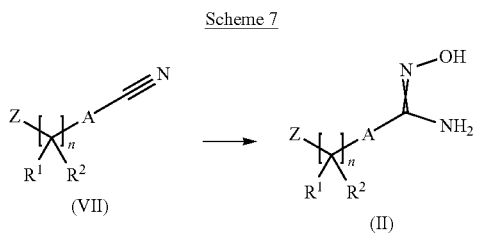

Similarly, a compound of Formula (II), wherein Z is hydrogen, can be prepared from a compound of Formula (VII), wherein Z is hydrogen, via reaction with hydroxylamine or a salt thereof, such as hydroxylamine hydrochloride salt, optionally in the presence of one or more bases. This reaction is shown in Scheme 7.

In particular, a compound of Formula (II-A), wherein Z is —$NR^3$—C(=W)—X, can be prepared from a compound of Formula (VII), wherein Z is is —$NR^3$—C(=W)—X, hereinafter referred to as compound of Formula (VII-A), via reaction with hydroxylamine or a salt thereof, such as hydroxylamine hydrochloride salt, optionally in the presence of one or more bases. This reaction is shown in Scheme 8.

Scheme 8

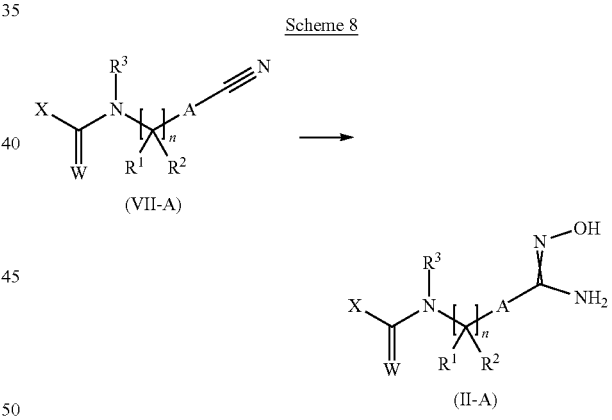

Examples of suitable bases include, for instance, trimethylamine. The reaction can be carried out in a solvent, such as methanol. The reaction is typically carried out at a temperature from 0° C. to 100° C. For related examples, see Kitamura, S. et al *Chem. Pharm. Bull*. (2001), 49, 268; and WO 2013/066838.

The compound of Formula (VII-A), wherein Z is —$NR^3$—C(=W)—X, can be prepared from a compound of Formula (VII), wherein Z is a halogen, via reaction with a compound of Formula (V) or a salt thereof, wherein $R^3$ is as defined above for a compound of Formula (I), to obtain an intermediate compound of Formula (VII-a) or a salt thereof. For related examples, see Miyawaki, K. et al *Heterocycles* (2001), 54, 887; and WO 2018/177894. This reaction is shown in Scheme 9.

Scheme 9

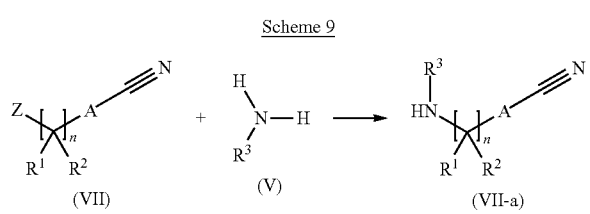

The compound of Formula (VII-a) or a salt thereof can be further reacted with a compound of Formula (VI), wherein X and W are as defined above for a compound of Formula (I) and T is halogen, hydroxy or $C_{1-4}$alkoxy, to obtain a compound of Formula (VII-A), wherein Z is —$NR^3$—C(=W)—X. For related examples, see WO 2018/177894. This reaction is shown in Scheme 10.

Scheme 10

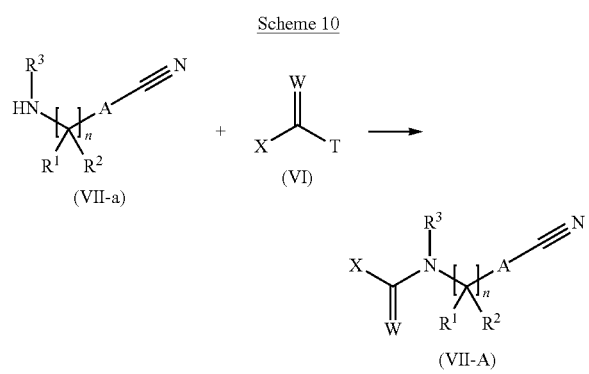

The compound of Formula (II), wherein Z is a halogen, can be prepared from a compound of Formula (II), wherein Z is hydrogen, via reaction with a halogenating agent, optionally in the presence of a radical initiator such as dibenzoyl peroxide or azobisisobutyronitrile (AIBN). Examples of suitable halogenating agents include, for instance, brominating agents such as bromine or N-bromosuccinimide. The reaction is typically carried out at a temperature from 55° C. to 100° C. For related examples, see J. *Am. Chem. Soc.* 1951, 73, 455.

Additionally, the compound of Formula (VII) can be prepared from a compound of Formula (VIII), wherein Y is a halogen, preferably Cl, Br or I, via metal-promoted reaction with a suitable cyanide reagent, such as Pd(0)/Zn(CN)$_2$ or CuCN, in a suitable solvent (e.g., dimethylformamide or N-methylpyrrolidone). The reaction is typically carried out at a temperature from 100° C. to 120° C. For related examples, see US 2007/0155739; and WO 2009/022746. This reaction is shown in Scheme 11.

Scheme 11

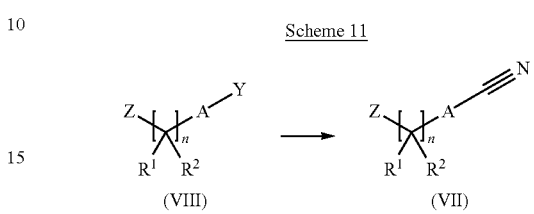

Compounds of Formula (VIII), wherein n is preferably 1, can be prepared from compounds of Formula (IX), wherein Y is a halogen, preferably Cl, Br or I, via reaction with a compound of Formula (X), in the presence of a base (e.g. $K_2CO_3$, $Cs_2CO_3$, or NaH) in a suitable solvent (e.g. dimethylformamide or tetrahydrofuran). The reaction is typically carried out at a temperature from 25° C. to 110° C. In some cases, a better reaction performance may be gained from the use of a catalyst (e.g., NaI or 4-dimethylaminopyridine) and with microwave irradiation. For related examples, see WO 2013/132253; WO 2018/177894; and Garcia, M. et al *Org. Biomol. Chem.* (2004), 11, 1633. This reaction is shown in Scheme 12.

Scheme 12

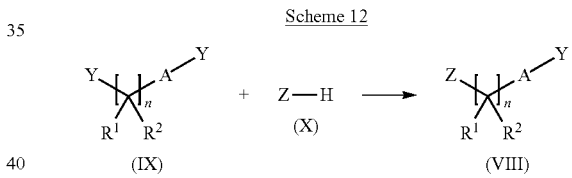

The process for the preparation of the compound of Formula (I-A), wherein $Z^2$ is —$NR^3$—C(=W)—X, is preferably carried out according to any the following pathways. These reactions are shown in Scheme 13.

Scheme 13

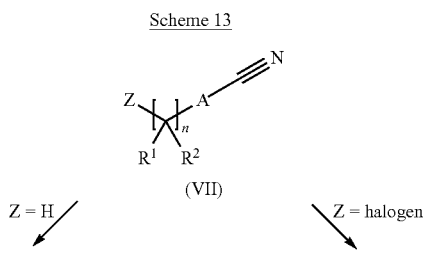

-continued

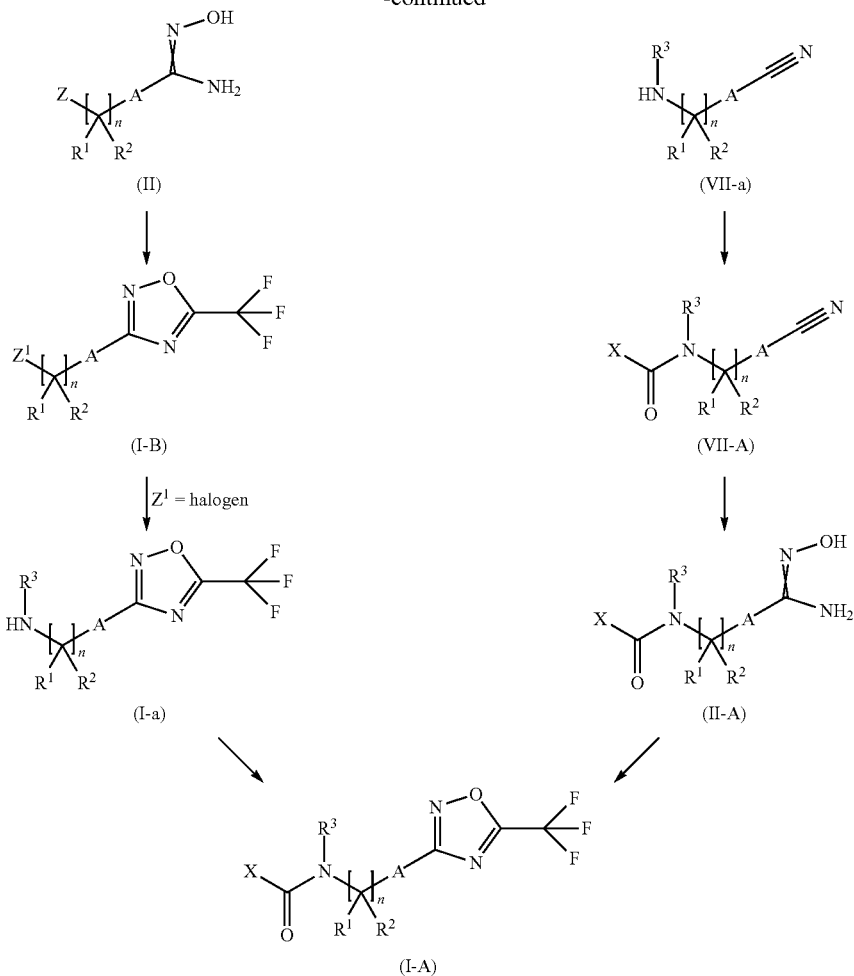

According to one embodiment of the invention, the process for the preparation of the compound of Formula (I-A), wherein $Z^2$ is —$NR^3$—C(=W)—X, typically comprises:

(A-1) a step of reacting a compound of Formula (II), wherein A, n, $R^1$, $R^2$ and $Z^1$ are as defined for the compound of Formula (I), with a compound of Formula (III), wherein $R^{12}$ is $C_{1-4}$alkyl, to obtain a compound of Formula (I-B):

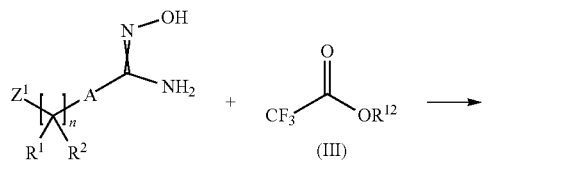

(A-2) a step of reacting a compound of Formula (I-B), wherein $Z^1$ is a halogen, with a compound of Formula (V)

or a salt thereof, wherein $R^3$ is as defined above for a compound of Formula (I), to obtain an intermediate compound of Formula (I-a) or a salt thereof:

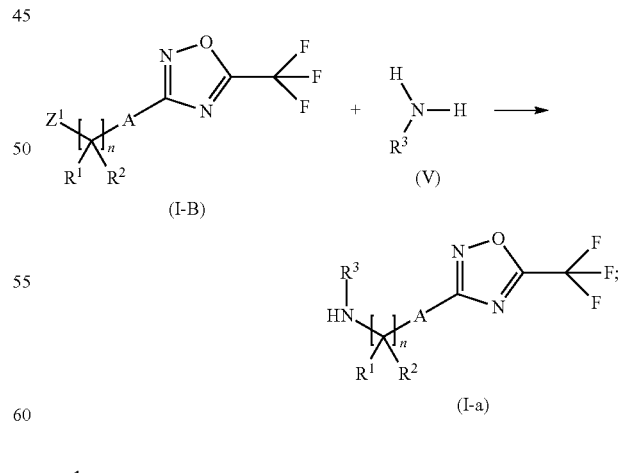

and (A-3) a step of reacting a compound of Formula (I-a) or a salt thereof with a compound of Formula (VI), wherein X and W are as defined above for a compound of Formula (I) and T is halogen, hydroxy or $C_{1-4}$alkoxy:

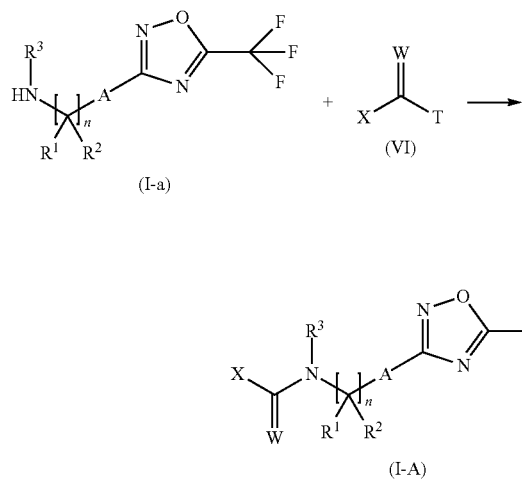

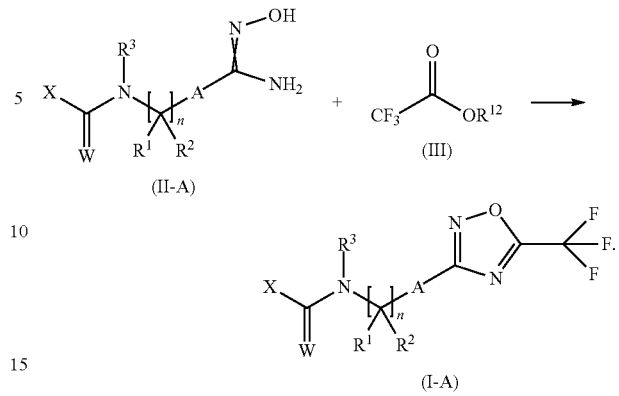

The compound of Formula (II) of this embodiment of the invention can be prepared as described above.

According to a further embodiment of the invention, the process for the preparation of the compound of Formula (I-A), wherein $Z^2$ is —$NR^3$—$C(=W)$—$X$, typically comprises a step of reacting a compound of Formula (II-A), wherein A, n, $R^1$, $R^2$, $R^3$, X and W are as defined above for the compound of Formula (I), with a compound of Formula (III), wherein $R^{12}$ is $C_{1-4}$alkyl:

The compound of Formula (II-A) of this embodiment of the invention can be prepared as described above.

Preferred groups and values for the substituents n, m, A-1, A-2, $R^1$, $R^2$, $R^3$, $R^4$, $R^5$, $R^6$, $R^7$, $R^8$, $R^9$, $R^{10}$, $R^{11}$, $Z(Z^1, Z^2)$, W, and X in the compounds of Formula (I) are, in any combination thereof, as set out below in Tables A-E.

According to an embodiment of the process of the invention, a compound of Formula (I) is selected from compounds no. A.01, A.02, A.03, A.04, A.05, A.06, A.07, A.08, A.09, A.10, A.11, A.12, A.13, A.14, A.15, A.16, A.17, or A.18 as defined in the Table A below. More preferably, a compound of Formula (I) is selected from compounds no. A.01, A.08, A.09, A.10, A.11, A.17, or A.18 as defined in the Table A below.

TABLE A

| Compound number | Compound Structure | IUPAC name |
|---|---|---|
| A.01 | ![structure] | N-[[4-[5-(trifluoromethyl)-1,2,4-oxadiazol-3-yl]phenyl]methyl]propanamide |
| A.02 | ![structure] | 2,2-dimethyl-N-[[4-[5-(trifluoromethyl)-1,2,4-oxadiazol-3-yl]phenyl]methyl]but-3-ynamide |
| A.03 | ![structure] | N-[[4-[5-(trifluoromethyl)-1,2,4-oxadiazol-3-yl]phenyl]methyl]butanamide |

TABLE A-continued

| Compound number | Compound Structure | IUPAC name |
|---|---|---|
| A.04 | 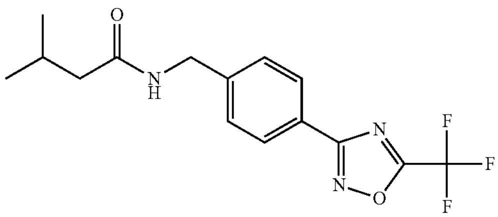 [SMILES: CC(C)CC(=O)NCc1ccc(-c2noc(C(F)(F)F)n2)cc1] | 3-methyl-N-[[4-[5-(trifluoromethyl)-1,2,4-oxadiazol-3-yl]phenyl]methyl]butanamide |
| A.05 | 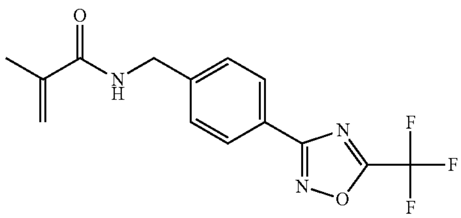 [SMILES: C=C(C)C(=O)NCc1ccc(-c2noc(C(F)(F)F)n2)cc1] | 2-methyl-N-[[4-[5-(trifluoromethyl)-1,2,4-oxadiazol-3-yl]phenyl]methyl]prop-2-enamide |
| A.06 | 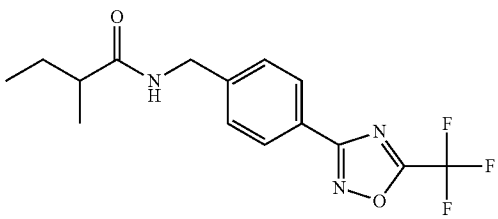 [SMILES: CCC(C)C(=O)NCc1ccc(-c2noc(C(F)(F)F)n2)cc1] | 2-methyl-N-[[4-[5-(trifluoromethyl)-1,2,4-oxadiazol-3-yl]phenyl]methyl]butanamide |
| A.07 | 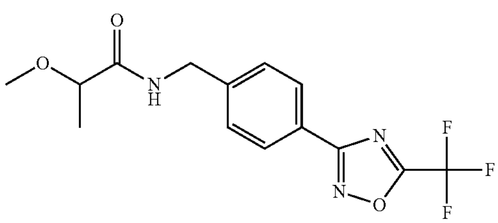 [SMILES: COC(C)C(=O)NCc1ccc(-c2noc(C(F)(F)F)n2)cc1] | 2-methoxy-N-[[4-[5-(trifluoromethyl)-1,2,4-oxadiazol-3-yl]phenyl]methyl]propanamide |
| A.08 | 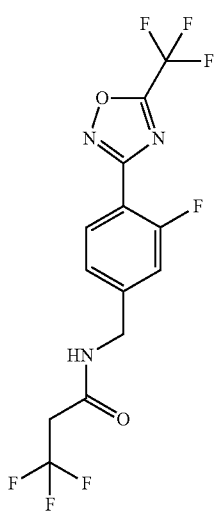 [SMILES: O=C(CC(F)(F)F)NCc1ccc(-c2noc(C(F)(F)F)n2)c(F)c1] | 3,3,3-trifluoro-N-[[3-fluoro-4-[5-(trifluoromethyl)-1,2,4-oxadiazol-3-yl]phenyl]methyl]propanamide |

TABLE A-continued

| Compound number | Compound Structure | IUPAC name |
| --- | --- | --- |
| A.09 | 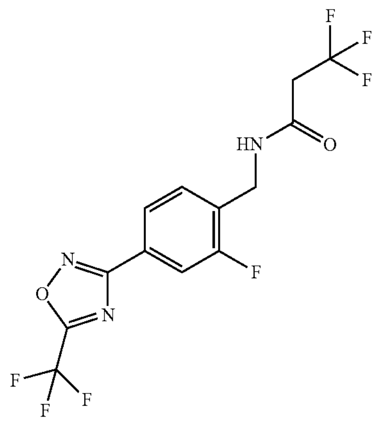 [SMILES: O=C(CC(F)(F)F)NCc1ccc(-c2noc(C(F)(F)F)n2)cc1F] | 3,3,3-trifluoro-N-[[2-fluoro-4-[5-(trifluoromethyl)-1,2,4-oxadiazol-3-yl]phenyl]methyl]propanamide |
| A.10 | 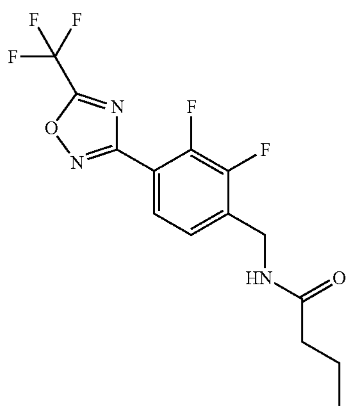 [SMILES: CCCC(=O)NCc1ccc(-c2noc(C(F)(F)F)n2)c(F)c1F] | N-[[2,3-difluoro-4-[5-(trifluoromethyl)-1,2,4-oxadiazol-3-yl]phenyl]pmethyl]butanamide |
| A.11 | 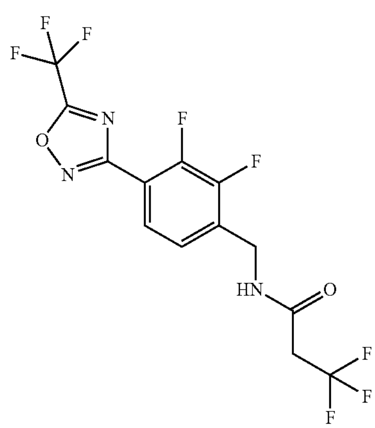 [SMILES: O=C(CC(F)(F)F)NCc1ccc(-c2noc(C(F)(F)F)n2)c(F)c1F] | N-[[2,3-difluoro-4-[5-(trifluoromethyl)-1,2,4-oxadiazol-3-yl]phenyl]methyl]-3,3,3-trifluoro-propanamide |
| A.12 | 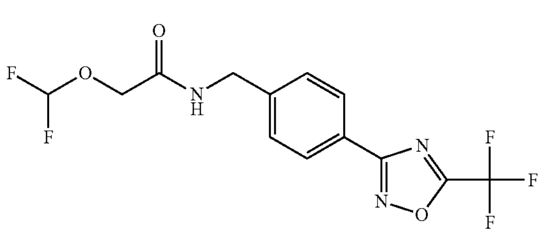 [SMILES: O=C(COC(F)F)NCc1ccc(-c2noc(C(F)(F)F)n2)cc1] | 2-(difluoromethoxy)-N-[[4-[5-(trifluoromethyl)-1,2,4-oxadiazol-3-yl]phenyl]methyl]acetamide |

TABLE A-continued

| Compound number | Compound Structure | IUPAC name |
| --- | --- | --- |
| A.13 | 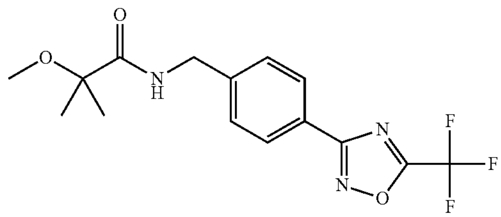 [SMILES: COC(C)(C)C(=O)NCc1ccc(-c2noc(C(F)(F)F)n2)cc1] | 2-methoxy-2-methyl-N-[[4-[5-(trifluoromethyl)-1,2,4-oxadiazol-3-yl]phenyl]methyl]propanamide |
| A.14 | 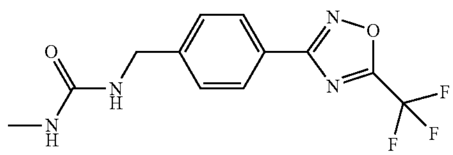 [SMILES: CNC(=O)NCc1ccc(-c2noc(C(F)(F)F)n2)cc1] | 1-methyl-3-[[4-[5-(trifluoromethyl)-1,2,4-oxadiazol-3-yl]phenyl]methyl]urea |
| A.15 | 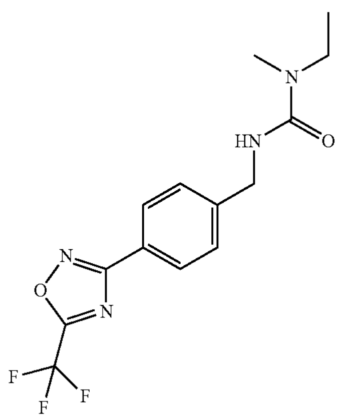 [SMILES: CCN(C)C(=O)NCc1ccc(-c2noc(C(F)(F)F)n2)cc1] | 1-ethyl-1-methyl-3-[[4-[5-(trifluoromethyl)-1,2,4-oxadiazol-3-yl]phenyl]methyl]urea |
| A.16 | 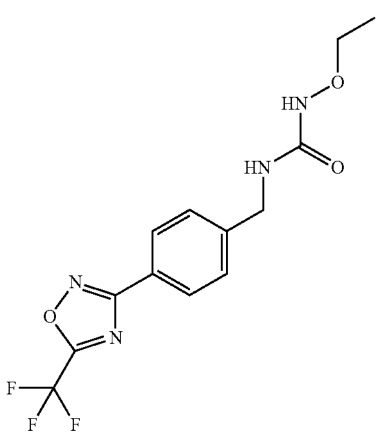 [SMILES: CCONC(=O)NCc1ccc(-c2noc(C(F)(F)F)n2)cc1] | 1-ethoxy-3-[[4-[5-(trifluoromethyl)-1,2,4-oxadiazol-3-yl]phenyl]methyl]urea |
| A.17 | 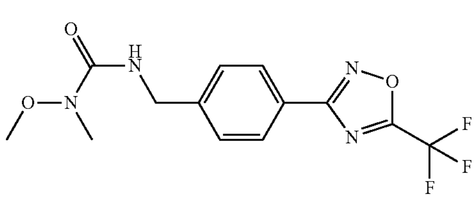 [SMILES: CON(C)C(=O)NCc1ccc(-c2noc(C(F)(F)F)n2)cc1] | 1-methoxy-1-methyl-3-[[4-[5-(trifluoromethyl)-1,2,4-oxadiazol-3-yl]phenyl]methyl]urea |

TABLE A-continued

| Compound number | Compound Structure | IUPAC name |
|---|---|---|
| A.18 | 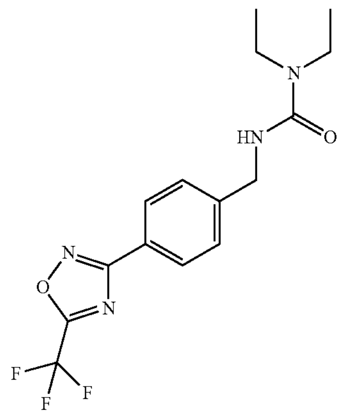 [SMILES: CCN(CC)C(=O)NCc1ccc(-c2noc(C(F)(F)F)n2)cc1] | 1,1-diethyl-3-[[4-[5-(trifluoromethyl)-1,2,4-oxadiazol-3-yl]phenyl]methyl]urea |

The presence of an asymmetric carbon atom in compounds A.04 and A.07 means that these compounds may occur in chiral enantiomeric forms, i.e., (R)- and (S)-enantiomers as depicted below.

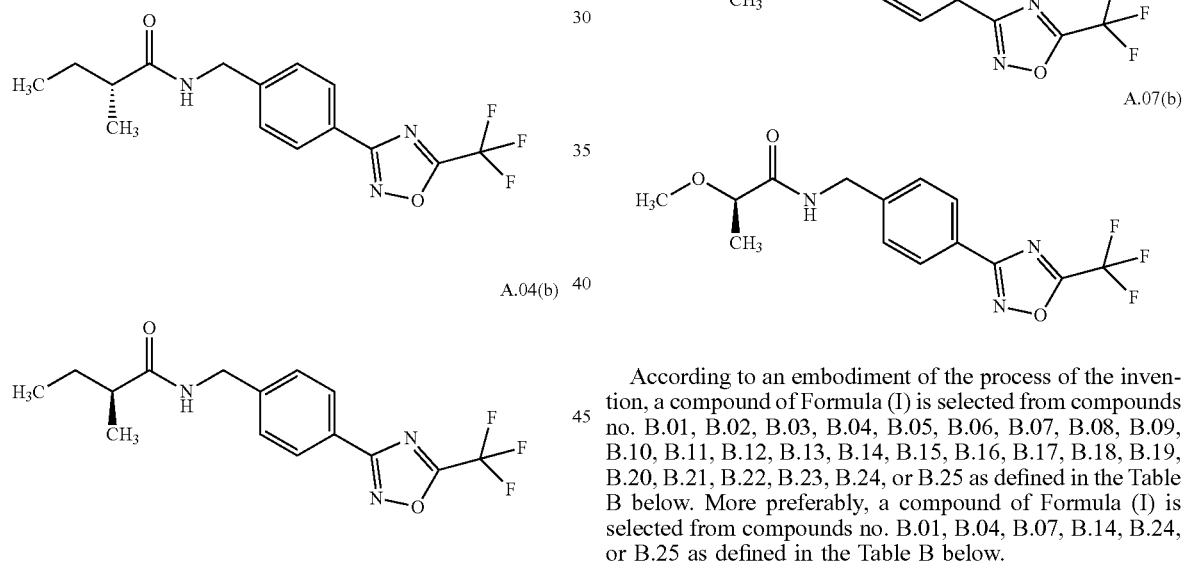

According to an embodiment of the process of the invention, a compound of Formula (I) is selected from compounds no. B.01, B.02, B.03, B.04, B.05, B.06, B.07, B.08, B.09, B.10, B.11, B.12, B.13, B.14, B.15, B.16, B.17, B.18, B.19, B.20, B.21, B.22, B.23, B.24, or B.25 as defined in the Table B below. More preferably, a compound of Formula (I) is selected from compounds no. B.01, B.04, B.07, B.14, B.24, or B.25 as defined in the Table B below.

TABLE B

| Compound number | Compound structure | IUPAC name |
|---|---|---|
| B.01 | 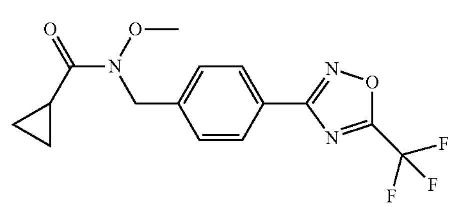 [SMILES: CON(Cc1ccc(-c2noc(C(F)(F)F)n2)cc1)C(=O)C1CC1] | N-methoxy-N-[[4-[5-(trifluoromethyl)-1,2,4-oxadiazol-3-yl]phenyl]methyl]cyclopropanecarboxamide |

TABLE B-continued

| Compound number | Compound structure | IUPAC name |
| --- | --- | --- |
| B.02 | 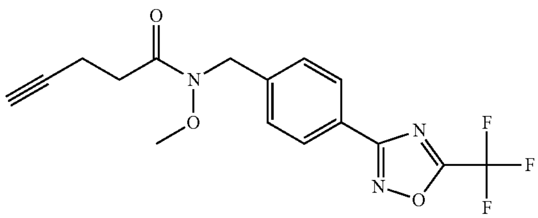 [SMILES: C#CCCC(=O)N(Cc1ccc(-c2noc(C(F)(F)F)n2)cc1)OC] | N-methoxy-N-[[4-[5-(trifluoromethyl)-1,2,4-oxadiazol-3-yl]phenyl]methyl]pent-4-ynamide |
| B.03 | 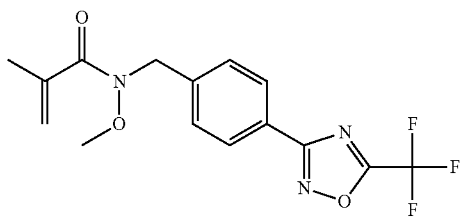 [SMILES: C=C(C)C(=O)N(Cc1ccc(-c2noc(C(F)(F)F)n2)cc1)OC] | N-methoxy-2-methyl-N-[[4-[5-(trifluoromethyl)-1,2,4-oxadiazol-3-yl]phenyl]methyl]prop-2-enamide |
| B.04 | 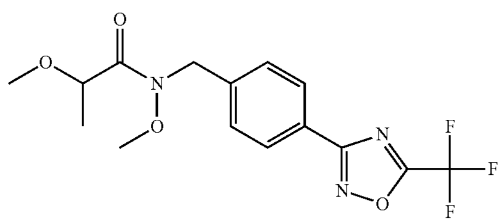 [SMILES: COC(C)C(=O)N(Cc1ccc(-c2noc(C(F)(F)F)n2)cc1)OC] | N,2-dimethoxy-N-[[4-[5-(trifluoromethyl)-1,2,4-oxadiazol-3-yl]phenyl]methyl]propanamide |
| B.05 | 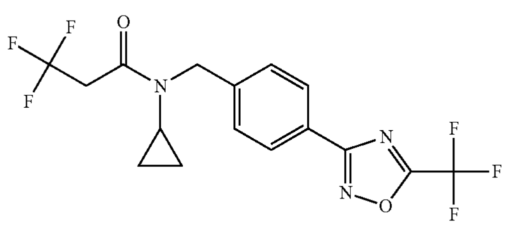 [SMILES: O=C(CC(F)(F)F)N(Cc1ccc(-c2noc(C(F)(F)F)n2)cc1)C1CC1] | N-cyclopropyl-3,3,3-trifluoro-N-[[4-[5-(trifluoromethyl)-1,2,4-oxadiazol-3-yl]phenyl]methyl]propanamide |
| B.06 | 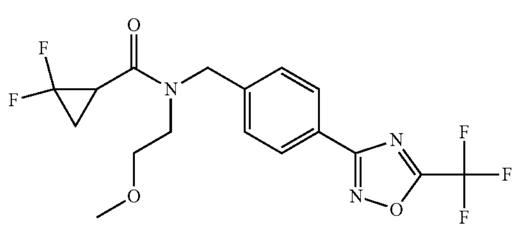 [SMILES: COCCN(Cc1ccc(-c2noc(C(F)(F)F)n2)cc1)C(=O)C1CC1(F)F] | 2,2-difluoro-N-(2-methoxyethyl)-N-[[4-[5-(trifluoromethyl)-1,2,4-oxadiazol-3-yl]phenyl]methyl]cyclopropanecarboxamide |
| B.07 | 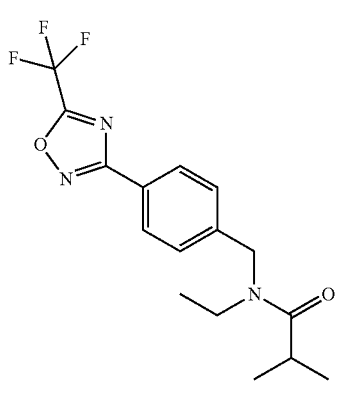 [SMILES: CCN(Cc1ccc(-c2noc(C(F)(F)F)n2)cc1)C(=O)C(C)C] | N-ethyl-2-methyl-N-[[4-[5-(trifluoromethyl)-1,2,4-oxadiazol-3-yl]phenyl]methyl]propanamide |

TABLE B-continued

| Compound number | Compound structure | IUPAC name |
|---|---|---|
| B.08 | 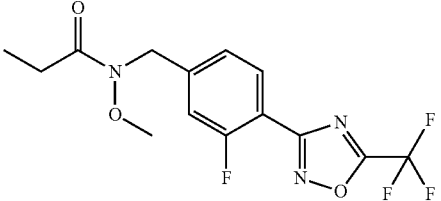 [SMILES: CCC(=O)N(Cc1ccc(-c2noc(C(F)(F)F)n2)c(F)c1)OC] | N-[[3-fluoro-4-[5-(trifluoromethyl)-1,2,4-oxadiazol-3-yl]phenyl]methyl]-N-methoxy-propanamide |
| B.09 | 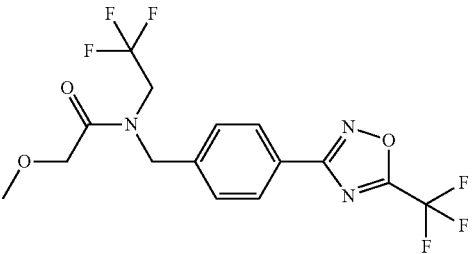 [SMILES: COCC(=O)N(Cc1ccc(-c2noc(C(F)(F)F)n2)cc1)CC(F)(F)F] | 2-methoxy-N-(2,2,2-trifluoroethyl)-N-[[4-[5-(trifluoromethyl)-1,2,4-oxadiazol-3-yl]phenyl]methyl]acetamide |
| B.10 | 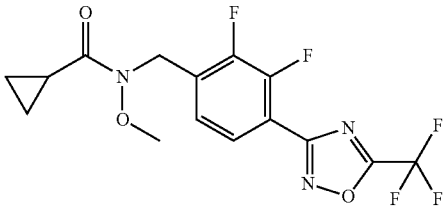 [SMILES: CON(Cc1ccc(-c2noc(C(F)(F)F)n2)c(F)c1F)C(=O)C1CC1] | N-[[2,3-difluoro-4-[5-(trifluoromethyl)-1,2,4-oxadiazol-3-yl]phenyl]methyl]-N-methoxy-cyclopropanecarboxamide |
| B.11 | 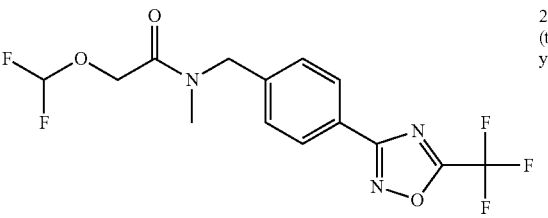 | 2-(difluoromethoxy)-N-methyl-N-[[4-[5-(trifluoromethyl)-1,2,4-oxadiazol-3-yl]phenyl]methyl]acetamide |
| B.12 | 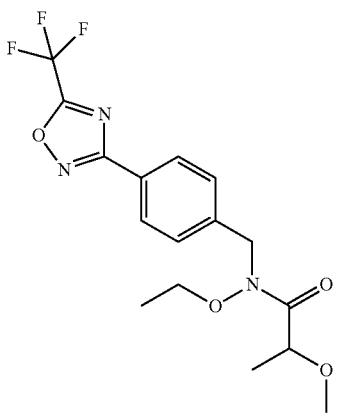 [SMILES: CCON(Cc1ccc(-c2noc(C(F)(F)F)n2)cc1)C(=O)C(C)OC] | N-ethoxy-2-methoxy-N-[[4-[5-(trifluoromethyl)-1,2,4-oxadiazol-3-yl]phenyl]methyl]propanamide |

TABLE B-continued

| Compound number | Compound structure | IUPAC name |
| --- | --- | --- |
| B.13 | 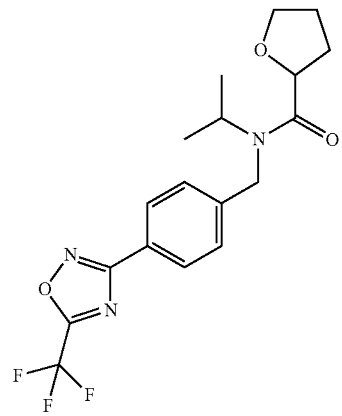 [SMILES: CC(C)N(Cc1ccc(-c2noc(C(F)(F)F)n2)cc1)C(=O)C1CCCO1] | N-isopropyl-N-[[4-[5-(trifluoromethyl)-1,2,4-oxadiazol-3-yl]phenyl]methyl]tetrahydrofuran-2-carboxamide |
| B.14 | 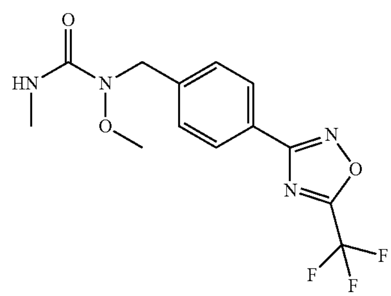 [SMILES: CNC(=O)N(Cc1ccc(-c2noc(C(F)(F)F)n2)cc1)OC] | 1-methoxy-3-methyl-1-[[4-[5-(trifluoromethyl)-1,2,4-oxadiazol-3-yl]phenyl]methyl]urea |
| B.15 | 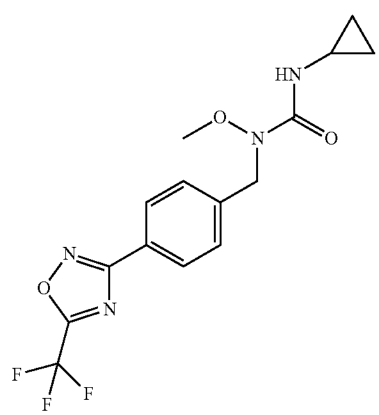 [SMILES: CON(Cc1ccc(-c2noc(C(F)(F)F)n2)cc1)C(=O)NC1CC1] | 3-cyclopropyl-1-methoxy-1-[[4-[5-(trifluoromethyl)-1,2,4-oxadiazol-3-yl]phenyl]methyl]urea |
| B.16 | 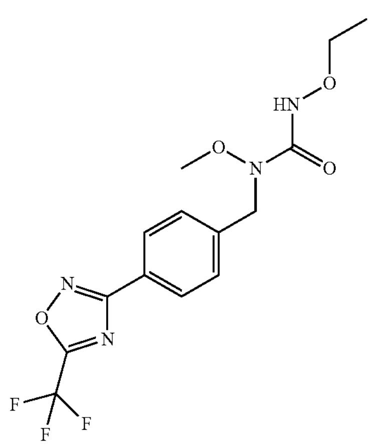 [SMILES: CCONC(=O)N(Cc1ccc(-c2noc(C(F)(F)F)n2)cc1)OC] | 3-ethoxy-1-methoxy-1-[[4-[5-(trifluoromethyl)-1,2,4-oxadiazol-3-yl]phenyl]methyl]urea |

TABLE B-continued

| Compound number | Compound structure | IUPAC name |
|---|---|---|
| B.17 | 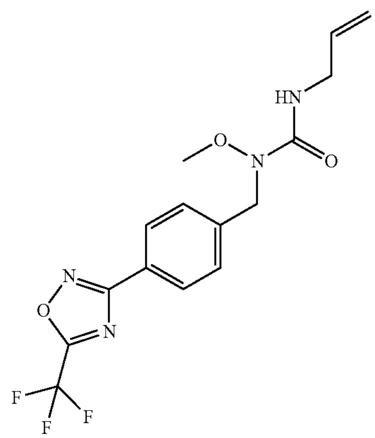 [SMILES: C=CCNC(=O)N(Cc1ccc(-c2noc(C(F)(F)F)n2)cc1)OC] | 3-allyl-1-methoxy-1-[[4-[5-(trifluoromethyl)-1,2,4-oxadiazol-3-yl]phenyl]methyl]urea |
| B.18 | 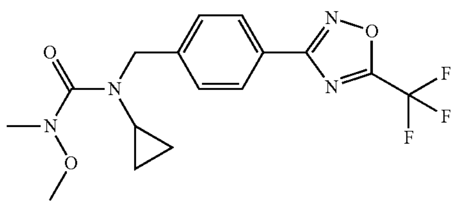 [SMILES: CON(C)C(=O)N(Cc1ccc(-c2noc(C(F)(F)F)n2)cc1)C1CC1] | 1-cyclopropyl-3-methoxy-3-methyl-1-[[4-[5-(trifluoromethyl)-1,2,4-oxadiazol-3-yl]phenyl]methyl]urea |
| B.19 | 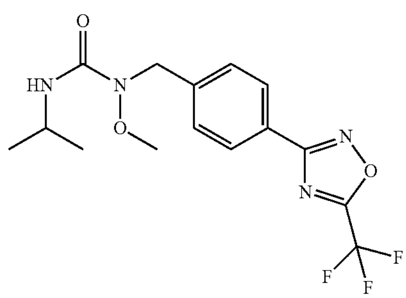 [SMILES: CON(Cc1ccc(-c2noc(C(F)(F)F)n2)cc1)C(=O)NC(C)C] | 3-isopropyl-1-methoxy-1-[[4-[5-(trifluoromethyl)-1,2,4-oxadiazol-3-yl]phenyl]methyl]urea |
| B.20 | 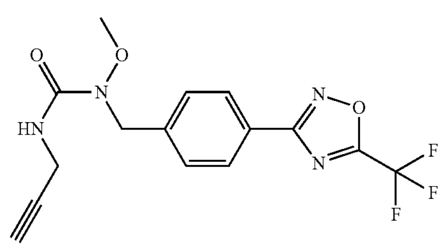 [SMILES: C#CCNC(=O)N(Cc1ccc(-c2noc(C(F)(F)F)n2)cc1)OC] | 1-methoxy-3-prop-2-ynyl-1-[[4-[5-(trifluoromethyl)-1,2,4-oxadiazol-3-yl]phenyl]methyl]urea |
| B.21 | 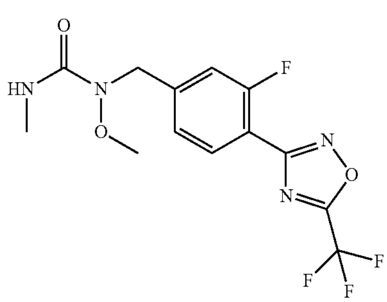 [SMILES: CNC(=O)N(Cc1ccc(-c2noc(C(F)(F)F)n2)c(F)c1)OC] | 1-[[3-fluoro-4-[5-(trifluoromethyl)-1,2,4-oxadiazol-3-yl]phenyl]methyl]-1-methoxy-3-methyl-urea |

TABLE B-continued
| Compound number | Compound structure | IUPAC name |
|---|---|---|
| B.22 | 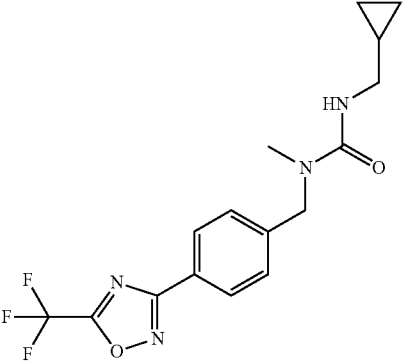 [SMILES: CN(Cc1ccc(-c2noc(C(F)(F)F)n2)cc1)C(=O)NCC1CC1] | 3-(cyclopropylmethyl)-1-methyl-1-[[4-[5-(trifluoromethyl)-1,2,4-oxadiazol-3-yl]phenyl]methyl]urea |
| B.23 | 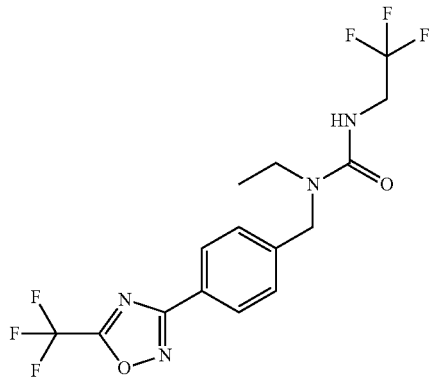 [SMILES: CCN(Cc1ccc(-c2noc(C(F)(F)F)n2)cc1)C(=O)NCC(F)(F)F] | 1-ethyl-3-(2,2,2-trifluoroethyl)-1-[[4-[5-(trifluoromethyl)-1,2,4-oxadiazol-3-yl]phenyl]methyl]urea |
| B.24 | 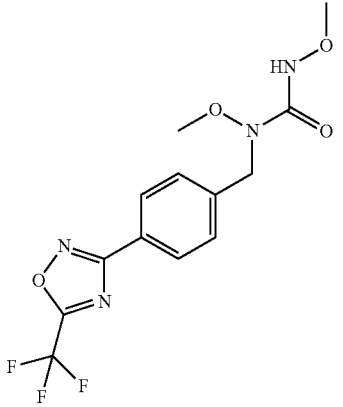 [SMILES: CONC(=O)N(Cc1ccc(-c2noc(C(F)(F)F)n2)cc1)OC] | 1,3-dimethoxy-1-[[4-[5-(trifluoromethyl)-1,2,4-oxadiazol-3-yl]phenyl]methyl]urea |

TABLE B-continued
| Compound number | Compound structure | IUPAC name |
|---|---|---|
| B.25 | 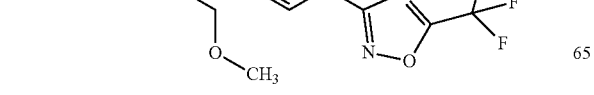 | 3-ethyl-1-methoxy-1-[[4-[5-(trifluoromethyl)-1,2,4-oxadiazol-3-yl]phenyl]methyl]urea |
The presence of an asymmetric carbon atom in compounds B.04, B.06, B.12 and B.13 means that these compounds may occur in chiral enantiomeric forms, i.e., (R)- and (S)-enantiomers as depicted below.
B.04(a)
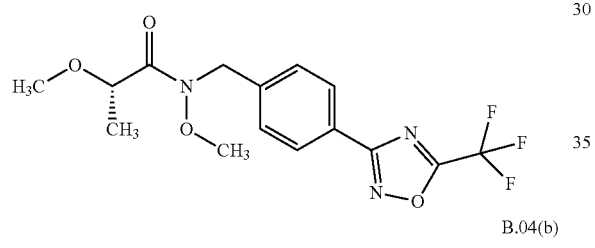
B.04(b)
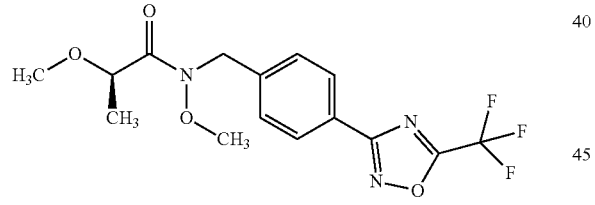
B.06(a)
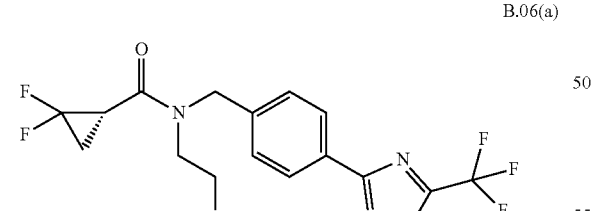
B.06(b)
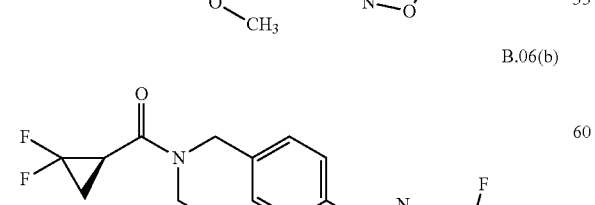
-continued
B.12(a)
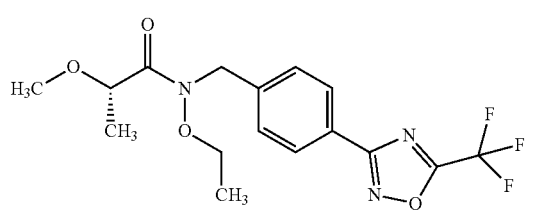
B.12(b)
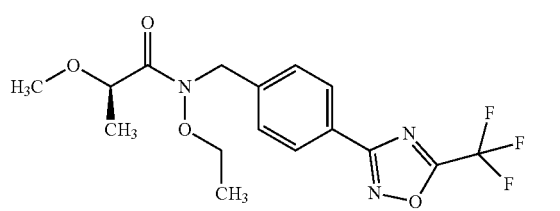
B.13(a)
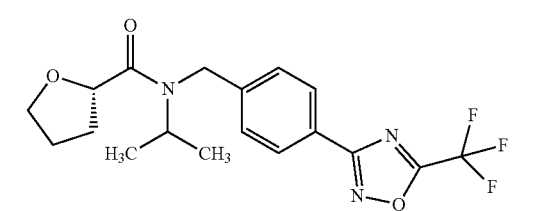
B.13(b)
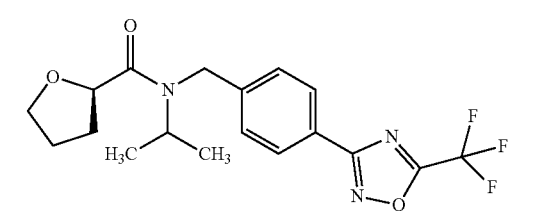

According to an embodiment of the process of the invention, a compound of Formula (I) is selected from compounds no. C.01, C.02, C.03, C.04, C.05, C.06, C.07, C.08, C.09, C.10, C.11, C.12, C.13, C.14, C.15, C.16, C.17, C.18, C.19, C.20, or C.21 as defined in the Table C below. More preferably, a compound of Formula (I) is selected from compounds no. C.03, C.06, C.07, C.15, C.16, or C.17 as defined in the Table C below.

TABLE C

| Compound number | Compound structure | IUPAC name |
|---|---|---|
| C.01 | 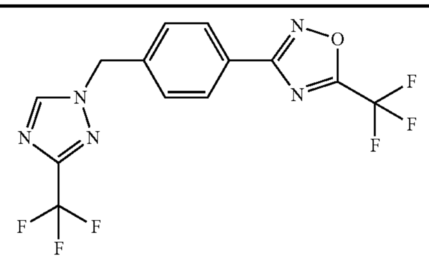 | 5-(trifluoromethyl)-3-[4-[[3-(trifluoromethyl)-1,2,4-triazol-1-yl]methyl]phenyl]-1,2,4-oxadiazole |
| C.02 | 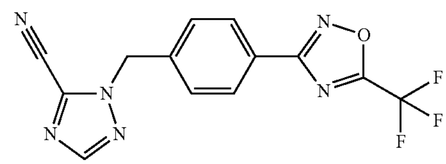 [SMILES: N#Cc1ncnn1Cc1ccc(-c2noc(C(F)(F)F)n2)cc1] | 2-[[4-[5-(trifluoromethyl)-1,2,4-oxadiazol-3-yl]phenyl]methyl]-1,2,4-triazole-3-carbonitrile |
| C.03 | 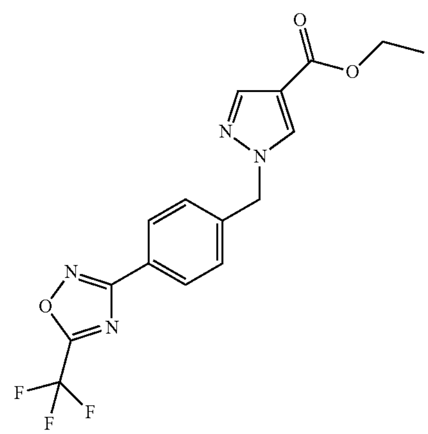 [SMILES: CCOC(=O)c1cnn(Cc2ccc(-c3noc(C(F)(F)F)n3)cc2)c1] | ethyl 1-[[4-[5-(trifluoromethyl)-1,2,4-oxadiazol-3-yl]phenyl]methyl]pyrazole-4-carboxylate |
| C.04 | 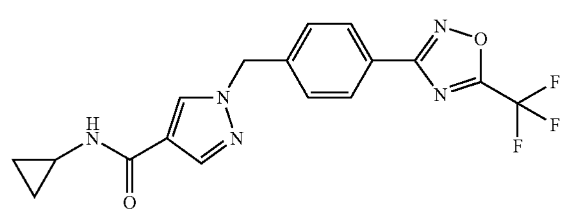 [SMILES: O=C(NC1CC1)c1cnn(Cc2ccc(-c3noc(C(F)(F)F)n3)cc2)c1] | N-cyclopropyl-1-[[4-[5-(trifluoromethyl)-1,2,4-oxadiazol-3-yl]phenyl]methyl]pyrazole-4-carboxamide |
| C.05 | 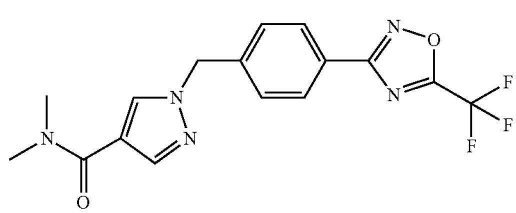 [SMILES: CN(C)C(=O)c1cnn(Cc2ccc(-c3noc(C(F)(F)F)n3)cc2)c1] | N,N-dimethyl-1-[[4-[5-(trifluoromethyl)-1,2,4-oxadiazol-3-yl]phenyl]methyl]pyrazole-4-carboxamide |
| C.06 | 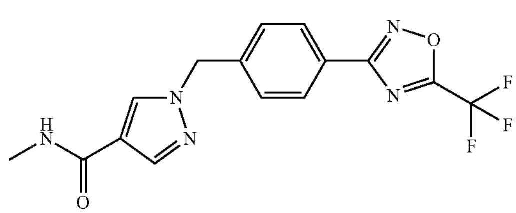 [SMILES: CNC(=O)c1cnn(Cc2ccc(-c3noc(C(F)(F)F)n3)cc2)c1] | N-methyl-1-[[4-[5-(trifluoromethyl)-1,2,4-oxadiazol-3-yl]phenyl]methyl]pyrazole-4-carboxamide |

TABLE C-continued
| Compound number | Compound structure | IUPAC name |
|---|---|---|
| C.07 | 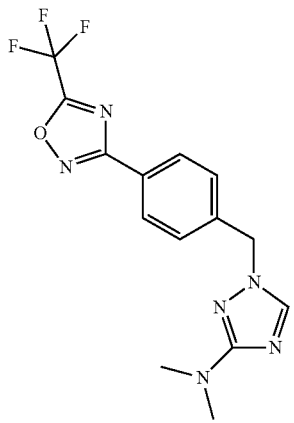 [SMILES: CN(C)c1ncn(Cc2ccc(-c3noc(C(F)(F)F)n3)cc2)n1] | N,N-dimethyl-1-[[4-[5-(trifluoromethyl)-1,2,4-oxadiazol-3-yl]phenyl]methyl]-1,2,4-triazol-3-amine |
| C.08 | 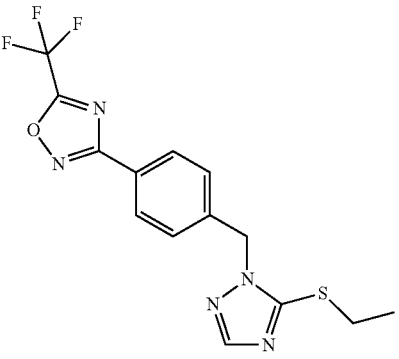 [SMILES: CCSc1ncnn1Cc1ccc(-c2noc(C(F)(F)F)n2)cc1] | 3-[4-[(5-ethylsulfanyl-1,2,4-triazol-1-yl)methyl]phenyl]-5-(trifluoromethyl)-1,2,4-oxadiazole |
| C.09 | 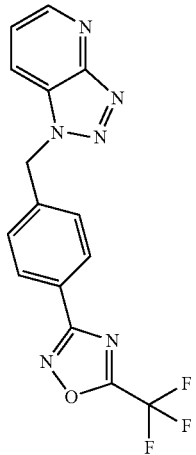 [SMILES: FC(F)(F)c1nc(-c2ccc(Cn3nnc4ncccc43)cc2)no1] | 3-[4-(triazolo[4,5-b]pyridin-1-ylmethyl)phenyl]-5-(trifluoromethyl)-1,2,4-oxadiazole |

TABLE C-continued

| Compound number | Compound structure | IUPAC name |
| --- | --- | --- |
| C.10 | 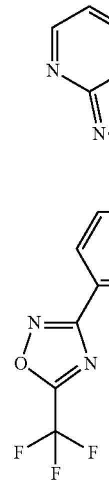 | 3-[4-(triazolo[4,5-b]pyridin-2-ylmethyl)phenyl]-5-(trifluoromethyl)-1,2,4-oxadiazole |
| C.11 | 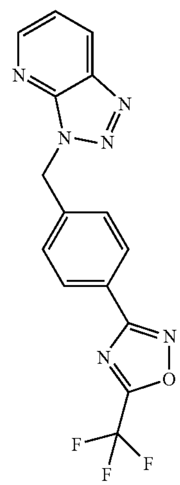 [SMILES: FC(F)(F)c1nc(-c2ccc(Cn3nnc4cccnc43)cc2)no1] | 3-[4-(triazolo[4,5-b]pyridin-3-ylmethyl)phenyl]-5-(trifluoromethyl)-1,2,4-oxadiazole |
| C.12 | 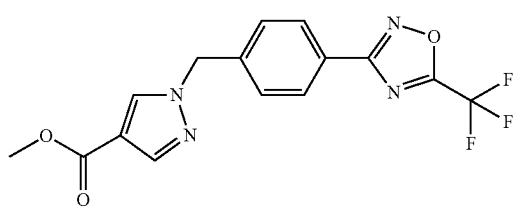 [SMILES: COC(=O)c1cnn(Cc2ccc(-c3noc(C(F)(F)F)n3)cc2)c1] | methyl 1-[[4-[5-(trifluoromethyl)-1,2,4-oxadiazol-3-yl]phenyl]methyl]pyrazole-4-carboxylate |
| C.13 | 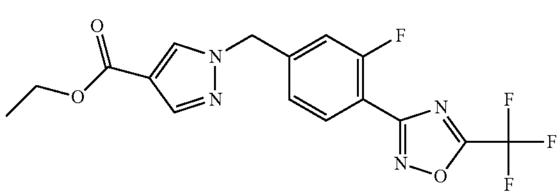 [SMILES: CCOC(=O)c1cnn(Cc2ccc(-c3noc(C(F)(F)F)n3)c(F)c2)c1] | ethyl 1-[[3-fluoro-4-[5-(trifluoromethyl)-1,2,4-oxadiazol-3-yl]phenyl]methyl]pyrazole-4-carboxylate |
| C.14 | 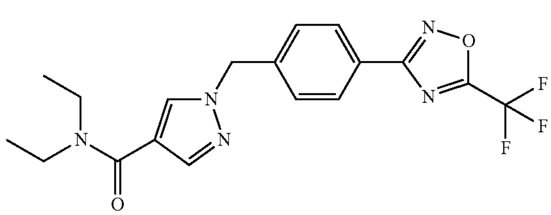 [SMILES: CCN(CC)C(=O)c1cnn(Cc2ccc(-c3noc(C(F)(F)F)n3)cc2)c1] | N,N-diethyl-1-[[4-[5-(trifluoromethyl)-1,2,4-oxadiazol-3-yl]phenyl]methyl]pyrazole-4-carboxylate |

TABLE C-continued

| Compound number | Compound structure | IUPAC name |
|---|---|---|
| C.15 | 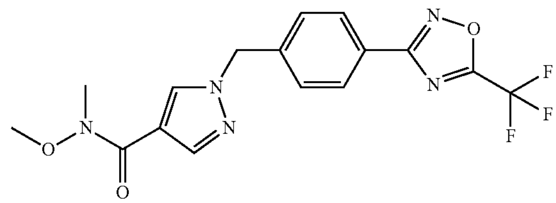 [SMILES: CON(C)C(=O)c1cnn(Cc2ccc(-c3noc(C(F)(F)F)n3)cc2)c1] | N-methoxy-N-methyl-1-[[4-[5-(trifluoromethyl)-1,2,4-oxadiazol-3-yl]phenyl]methyl]pyrazole-4-carboxylate |
| C.16 | 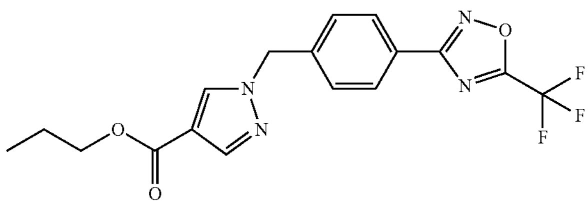 [SMILES: CCCOC(=O)c1cnn(Cc2ccc(-c3noc(C(F)(F)F)n3)cc2)c1] | propyl 1-[[4-[5-(trifluoromethyl)-1,2,4-oxadiazol-3-yl]phenyl]methyl]pyrazole-4-carboxylate |
| C.17 | 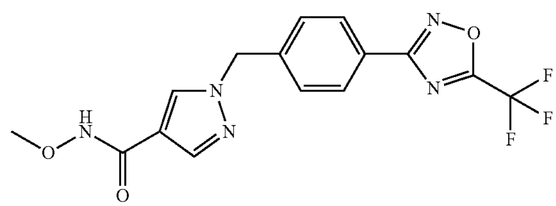 [SMILES: CONC(=O)c1cnn(Cc2ccc(-c3noc(C(F)(F)F)n3)cc2)c1] | N-methoxy-1-[[4-[5-(trifluoromethyl-1,2,4-oxadiazol-3-yl]phenyl]methyl]pyrazole-4-carboxamide |
| C.18 | 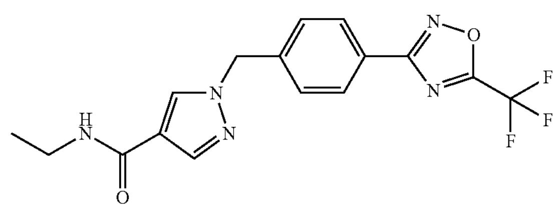 [SMILES: CCNC(=O)c1cnn(Cc2ccc(-c3noc(C(F)(F)F)n3)cc2)c1] | N-ethyl-1-[[4-[5-(trifluoromethyl)-1,2,4-oxadiazol-3-yl]phenyl]methyl]pyrazole-4-carboxamide |
| C.19 | 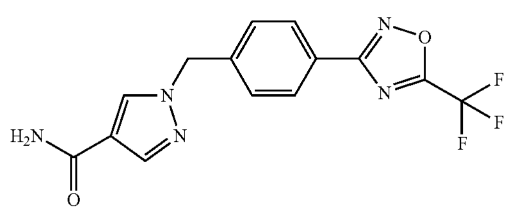 [SMILES: NC(=O)c1cnn(Cc2ccc(-c3noc(C(F)(F)F)n3)cc2)c1] | 1-[[4-[5-(trifluoromethyl)-1,2,4-oxadiazol-3-yl]phenyl]methyl]pyrazole-4-carboxamide |
| C.20 | 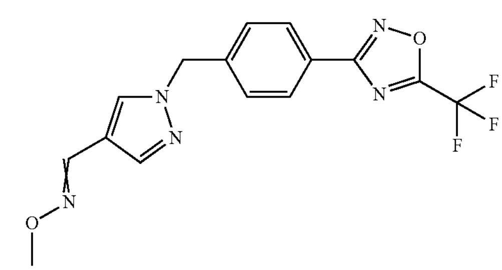 [SMILES: CON=Cc1cnn(Cc2ccc(-c3noc(C(F)(F)F)n3)cc2)c1] | N-methoxy-1-[1-[[4-[5-(trifluoromethyl)-1,2,4-oxadiazol-3-yl]phenyl]methyl]pyrazol-4-yl]methanimine |

TABLE C-continued

| Compound number | Compound structure | IUPAC name |
|---|---|---|
| C.21 | 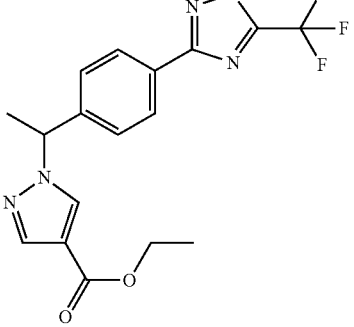 | ethyl 1-[1-[4-[5-(trifluoromethyl)-1,2,4-oxadiazol-3-yl]phenyl]ethyl]pyrazole-4-carboxylate |

The presence of an asymmetric carbon atom in compound C.21 means that these compounds may occur in chiral enantiomeric forms, i.e., (R)- and (S)-enantiomers as depicted below.

C.21(a)

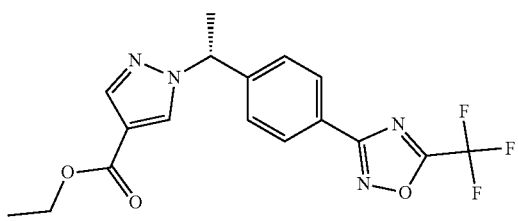

C.21(b)

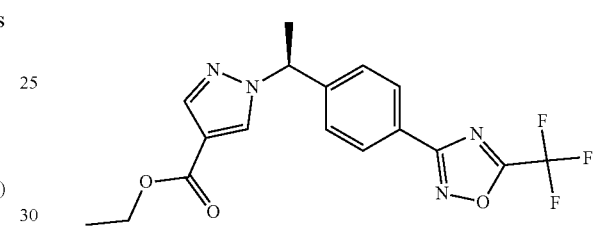

According to an embodiment of the process of the invention, a compound of Formula (I) is selected from compounds no. D.01, D.02, D.03, D.04, D.05, D.06, D.07, D.08, D.09, D.10, D.11, D.12, D.13, D.14, D.15, D.16, D.17, D.18, or D.19 as defined in the Table D below. More preferably, a compound of Formula (I) is selected from compounds no. D.01, D.02, D.03, D.04, D.05, D.06, D.07, D.10, or D.19 as defined in the Table D below.

TABLE D

| Compound number | Compound structure | IUPAC name |
|---|---|---|
| D.01 | 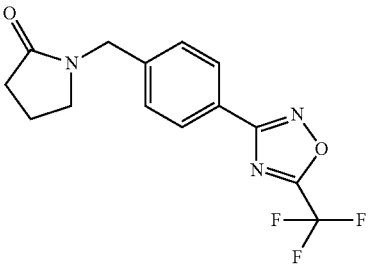 [SMILES: O=C1CCCN1Cc1ccc(-c2noc(C(F)(F)F)n2)cc1] | 1-[[4-[5-(trifluoromethyl)-1,2,4-oxadiazol-3-yl]phenyl]methyl]pyrrolidin-2-one |
| D.02 | 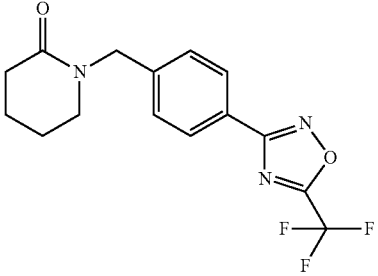 [SMILES: O=C1CCCCN1Cc1ccc(-c2noc(C(F)(F)F)n2)cc1] | 1-[[4-[5-(trifluoromethyl)-1,2,4-oxadiazol-3-yl]phenyl]methyl]piperidin-2-one |

TABLE D-continued

| Compound number | Compound structure | IUPAC name |
| --- | --- | --- |
| D.03 | 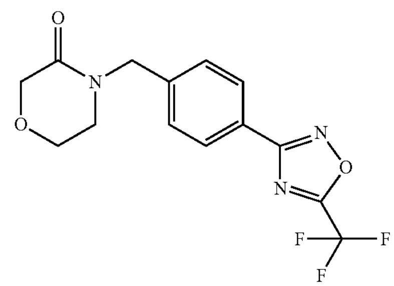 [SMILES: O=C1COCCN1Cc1ccc(-c2noc(C(F)(F)F)n2)cc1] | 4-[[4-[5-(trifluoromethyl)-1,2,4-oxadiazol-3-yl]phenyl]methyl]morpholin-3-one |
| D.04 | 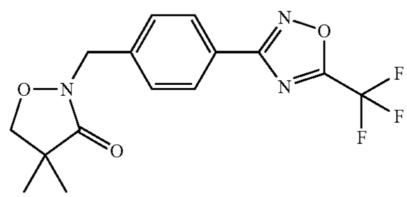 [SMILES: CC1(C)CON(Cc2ccc(-c3noc(C(F)(F)F)n3)cc2)C1=O] | 4,4-dimethyl-2-[[4-[5-(trifluoromethyl)-1,2,4-oxadiazol-3-yl]phenyl]methyl]isoxazolidin-3-one |
| D.05 | 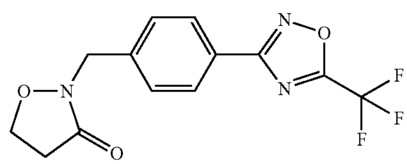 [SMILES: O=C1CCON1Cc1ccc(-c2noc(C(F)(F)F)n2)cc1] | 2-[[4-[5-(trifluoromethyl)-1,2,4-oxadiazol-3-yl]phenyl]methyl]isoxazolidin-3-one |
| D.06 | 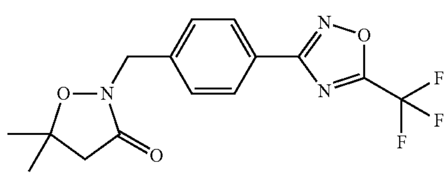 [SMILES: CC1(C)CC(=O)N(Cc2ccc(-c3noc(C(F)(F)F)n3)cc2)O1] | 5,5-dimethyl-2-[[4-[5-(trifluoromethyl)-1,2,4-oxadiazol-3-yl]phenyl]methyl]isoxazolidin-3-one |
| D.07 | 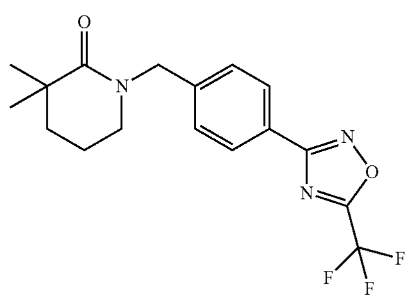 [SMILES: CC1(C)CCCN(Cc2ccc(-c3noc(C(F)(F)F)n3)cc2)C1=O] | 3,3-dimethyl-1-[[4-[5-(trifluoromethyl)-1,2,4-oxadiazol-3-yl]phenyl]methyl]piperidin-2-one |
| D.08 | 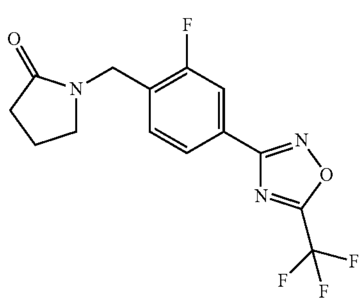 [SMILES: O=C1CCCN1Cc1ccc(-c2noc(C(F)(F)F)n2)cc1F] | 1-[[2-fluoro-4-[5-(trifluoromethyl)-1,2,4-oxadiazol-3-yl]phenyl]methyl]pyrrolidin-2-one |

TABLE D-continued

| Compound number | Compound structure | IUPAC name |
| --- | --- | --- |
| D.09 | 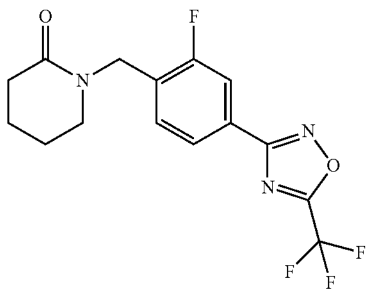 [SMILES: O=C1CCCCN1Cc1ccc(-c2noc(C(F)(F)F)n2)cc1F] | 1-[[2-fluoro-4-[5-(trifluoromethyl)-1,2,4-oxadiazol-3-yl]phenyl]methyl]piperidin-2-one |
| D.10 | 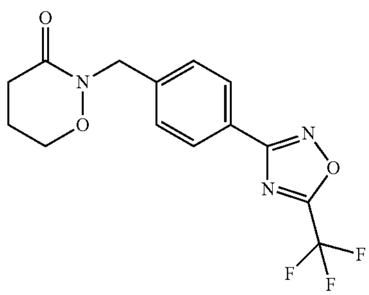 [SMILES: O=C1CCCON1Cc1ccc(-c2noc(C(F)(F)F)n2)cc1] | 2-[[4-[5-(trifluoromethyl)-1,2,4-oxadiazol-3-yl]phenyl]methyl]oxazinan-3-one |
| D.11 | 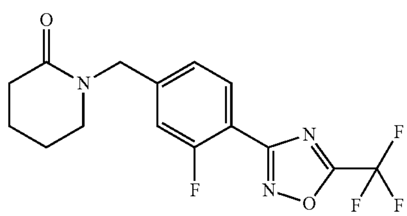 [SMILES: O=C1CCCCN1Cc1ccc(-c2noc(C(F)(F)F)n2)c(F)c1] | 1-[[3-fluoro-4-[5-(trifluoromethyl)-1,2,4-oxadiazol-3-yl]phenyl]methyl]piperidin-2-one |
| D.12 | 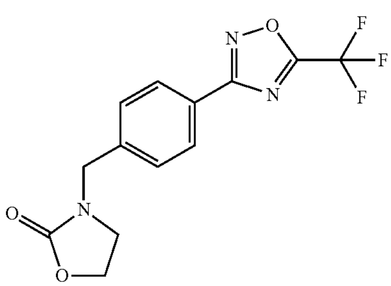 [SMILES: O=C1OCCN1Cc1ccc(-c2noc(C(F)(F)F)n2)cc1] | 3-[[4-[5-(trifluoromethyl)-1,2,4-oxadiazol-3-yl]phenyl]methyl]oxazolidin-2-one |
| D.13 | 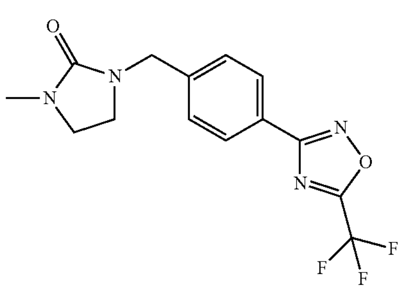 [SMILES: CN1CCN(Cc2ccc(-c3noc(C(F)(F)F)n3)cc2)C1=O] | 1-methyl-3-[[4-[5-(trifluoromethyl)-1,2,4-oxadiazol-3-yl]phenyl]methyl]imidazolidin-2-one |
| D.14 | 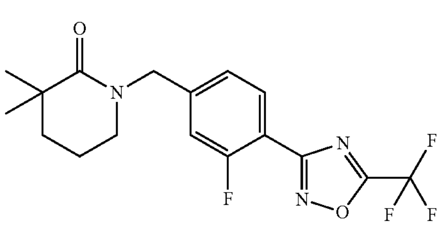 [SMILES: CC1(C)CCCN(Cc2ccc(-c3noc(C(F)(F)F)n3)c(F)c2)C1=O] | 1-[[3-fluoro-4-[5-(trifluoromethyl)-1,2,4-oxadiazol-3-yl]phenyl]methyl]-3,3-dimethyl-piperidin-2-one |

TABLE D-continued

| Compound number | Compound structure | IUPAC name |
| --- | --- | --- |
| D.15 | 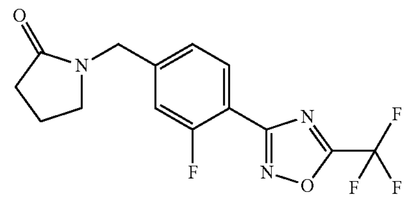 [SMILES: O=C1CCCN1Cc1ccc(-c2noc(C(F)(F)F)n2)c(F)c1] | 1-[[3-fluoro-4-[5-(trifluoromethyl)-1,2,4-oxadiazol-3-yl]phenyl]methyl]pyrrolidin-2-one |
| D16 | 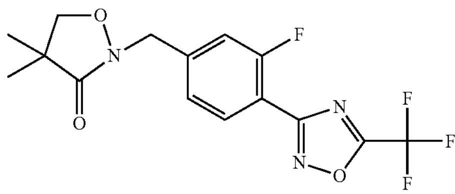 [SMILES: CC1(C)CON(Cc2ccc(-c3noc(C(F)(F)F)n3)c(F)c2)C1=O] | 2-[[3-fluoro-4-[5-(trifluoromethyl)-1,2,4-oxadiazol-3-yl]phenyl]methyl]-4,4-dimethyl-isoxazolidin-3-one |
| D.17 | 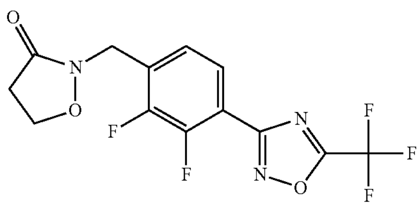 [SMILES: O=C1CCON1Cc1ccc(-c2noc(C(F)(F)F)n2)c(F)c1F] | 2-[[2,3-difluoro-4-[5-(trifluoromethyl)-1,2,4-oxadiazol-3-yl]phenyl]methyl]isoxazolidin-3-one |
| D.18 | 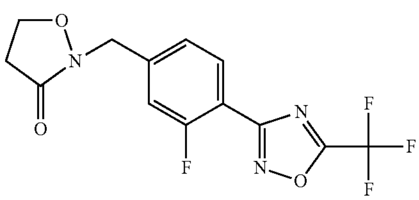 [SMILES: O=C1CCON1Cc1ccc(-c2noc(C(F)(F)F)n2)c(F)c1] | 2-[[3-fluoro-4-[5-(trifluoromethyl)-1,2,4-oxadiazol-3-yl]phenyl]methyl]isoxazolidin-3-one |
| D.19 | 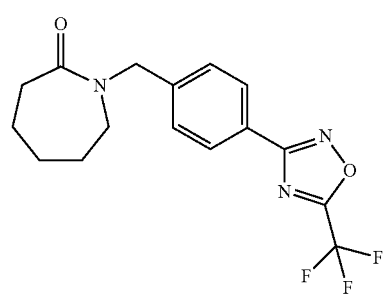 [SMILES: O=C1CCCCCN1Cc1ccc(-c2noc(C(F)(F)F)n2)cc1] | 1-[[4-[5-(trifluoromethyl)-1,2,4-oxadiazol-3-yl]phenyl]methyl]azepan-2-one |

According to an embodiment of the process of the invention, a compound of Formula (I) is selected from compounds no. E.01, E.02, E.03, E.04, E.05, E.06, E.07, E.08, E.09, E.10, E.11, E.12, E.13, E.14, E.15, E.16, E.17, E.18, E.19, E.20, E.21, or E.22 as defined in the Table E below. More preferably, a compound of Formula (I) is selected from compounds no. E.01, E.02, E.03, E.05, E.10, E.12, E.13, E.14, E.15, E.16, E.17, E.18, E.19, E.20, or E.22 as defined in the Table E below.

TABLE E

| Compound number | IUPAC name | Compound structure |
| --- | --- | --- |
| E.01 | | N-methyl-1-[[5-[5-(trifluoromethyl)-1,2,4-oxadiazol-3-yl]-2-thienyl]methyl]imidazole-2-carboxamide |
| E.02 | | (5-methylpyrazin-2-yl)-[5-[5-(trifluoromethyl)-1,2,4-oxadiazol-3-yl]-2-thienyl]methanone |
| E.03 | | (5-methylpyrazin-2-yl)-[5-[5-(trifluoromethyl)-1,2,4-oxadiazol-3-yl]-2-thienyl]methanol |
| E.04 | | 2-methoxy-N-methyl-2-[5-[5-(trifluoromethyl)-1,2,4-oxadiazol-3-yl]-2-thienyl]acetamide |
| E.05 | | (5-methylpyrazin-2-yl)-[4-[5-(trifluoromethyl)-1,2,4-oxadiazol-3-yl]phenyl]methanol |
| E.06 | | N-cyclopropyl-2-methoxy-2-[4-[5-(trifluoromethyl)-1,2,4-oxadiazol-3-yl]phenyl]acetamide |
| E.07 | | (5-methyl-2-pyridyl)-[5-[5-(trifluoromethyl)-1,2,4-oxadiazol-3-yl]-2-thienyl]methanol |

TABLE E-continued

| Compound number | IUPAC name | Compound structure |
| --- | --- | --- |
| E.08 | 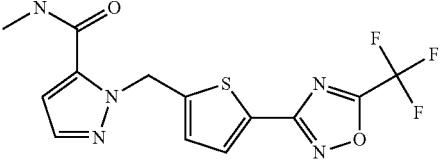 | N-methyl-2-[[5-[5-(trifluoromethyl)-1,2,4-oxadiazol-3-yl]-2-theinyl]methyl]pyrazole-3-carboxamide |
| E.09 | 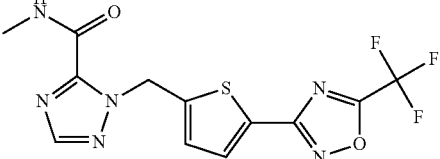 | N-methyl-2-[[5-[(trifluoromethyl)-1,2,4-oxadiazol-3-yl]-2-thienyl]methyl]-1,2,4-triazole-3-carboxamide |
| E.10 | 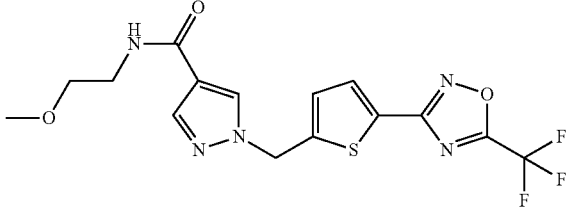 [SMILES: COCCNC(=O)c1cnn(Cc2ccc(-c3noc(C(F)(F)F)n3)s2)c1] | N-(2-methoxyethyl)-1-[[5-[5-(trifluoromethyl)-1,2,4-oxadiazol-3-yl]-2-thienyl]methyl]pyrazole-4-carboxamide |
| E.11 | 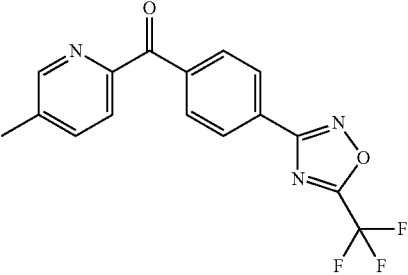 [SMILES: Cc1ccc(C(=O)c2ccc(-c3noc(C(F)(F)F)n3)cc2)nc1] | (5-methyl-2-pyridyl)-[4-[5-(trifluoromethyl)-1,2,4-oxadiazol-3-yl]phenyl]methanone |
| E.12 | 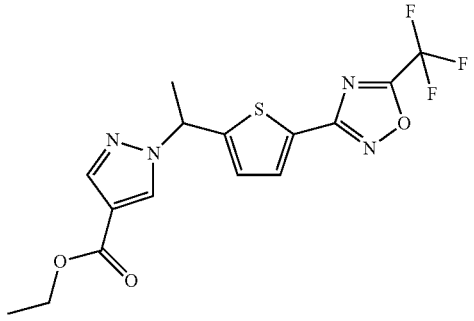 [SMILES: CCOC(=O)c1cnn(C(C)c2ccc(-c3noc(C(F)(F)F)n3)s2)c1] | ethyl 1-[1-[5-[5-(trifluoromethyl)-1,2,4-oxadiazol-3-yl]-2-thienyl]ethyl]pyrazole-4-carboxylate |
| E.13 | 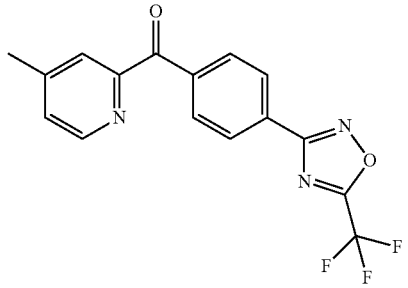 [SMILES: Cc1ccnc(C(=O)c2ccc(-c3noc(C(F)(F)F)n3)cc2)c1] | (4-methyl-2-pyridyl)-[4-[5-(trifluoromethyl)-1,2,4-oxadiazol-3-yl]phenyl]methanone |

TABLE E-continued

| Compound number | IUPAC name | Compound structure |
|---|---|---|
| E.14 | 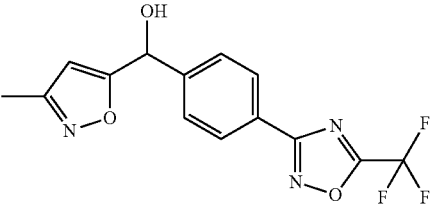 [SMILES: Cc1cc(C(O)c2ccc(-c3noc(C(F)(F)F)n3)cc2)on1] | (3-methylisoxazol-5-yl)-[4-[5-(trifluoromethyl)-1,2,4-oxadiazol-3-yl]phenyl]methanol |
| E.15 | 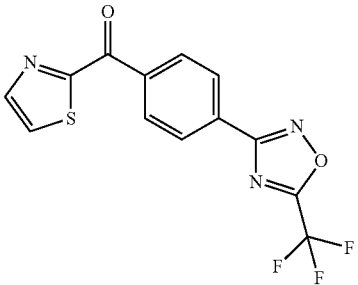 [SMILES: O=C(c1ccc(-c2noc(C(F)(F)F)n2)cc1)c1nccs1] | thiazol-2-yl-[4-[5-(trifluoromethyl)-1,2,4-oxadiazol-3-yl]phenyl]methanone |
| E.16 | 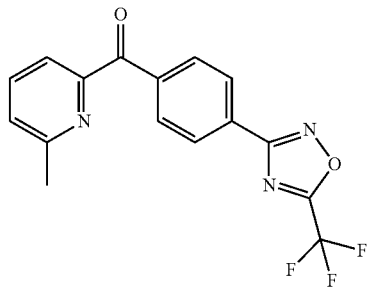 [SMILES: Cc1cccc(C(=O)c2ccc(-c3noc(C(F)(F)F)n3)cc2)n1] | (6-methyl-2-pyridyl)-[4-[5-(trifluoromethyl)-1,2,4-oxadiazol-3-yl]phenyl]methanone |
| E.17 | 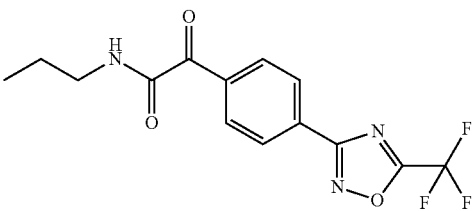 [SMILES: CCCNC(=O)C(=O)c1ccc(-c2noc(C(F)(F)F)n2)cc1] | 2-oxo-N-propyl-2-[4-[5-(trifluoromethyl)-1,2,4-oxadiazol-3-yl]phenyl]acetamide |
| E.18 | 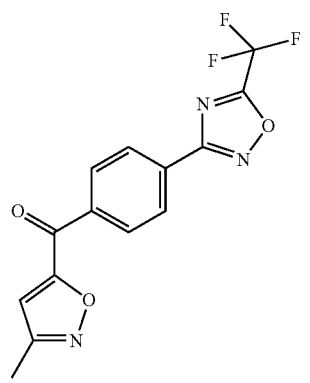 [SMILES: Cc1cc(C(=O)c2ccc(-c3noc(C(F)(F)F)n3)cc2)on1] | (3-methylisoxazol-5-yl)-[4-[5-(trifluoromethyl)-1,2,4-oxadiazol-3-yl]phenyl]methanone |

TABLE E-continued

| Compound number | IUPAC name | Compound structure |
|---|---|---|
| E.19 | 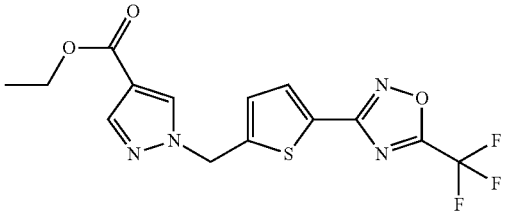 [SMILES: CCOC(=O)c1cnn(Cc2ccc(-c3noc(C(F)(F)F)n3)s2)c1] | ethyl 1-[[4-[5-(trifluoromethyl)-1,2,4-oxadiazol-3-yl]-2-thienyl]methyl]pyrazole-4-carboxylate |
| E.20 | 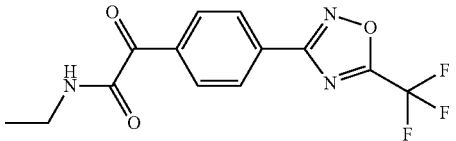 [SMILES: CCNC(=O)C(=O)c1ccc(-c2noc(C(F)(F)F)n2)cc1] | N-ethyl-2-oxo-2-[4-[5-(trifluoromethyl)-1,2,4-oxadiazol-3-yl]phenyl]acetamide |
| E.21 | 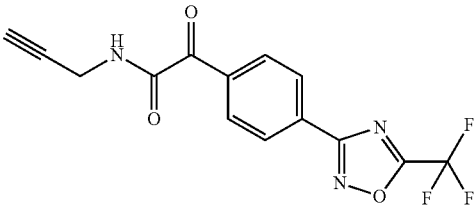 [SMILES: C#CCNC(=O)C(=O)c1ccc(-c2noc(C(F)(F)F)n2)cc1] | 2-oxo-N-prop-2-ynyl-2-[4-[5-(trifluoromethyl)-1,2,4-oxadiazol-3-yl]phenyl]acetamide |
| E.22 | 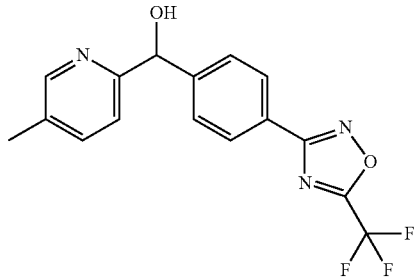 [SMILES: Cc1ccc(C(O)c2ccc(-c3noc(C(F)(F)F)n3)cc2)nc1] | (5-methyl-2-pyridyl)-[4-[5-(trifluoromethyl)-1,2,4-oxadiazol-3-yl]phenyl]methanol |

The presence of an asymmetric carbon atom in compound E.03, E.04, E.05, E.06, E.07, E.12, E.14 and E.22 means that these compounds may occur in chiral enantiomeric forms, i.e., (R)- and (S)-enantiomers as depicted below.

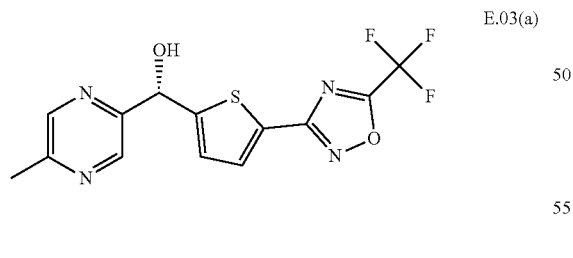

E.03(a)

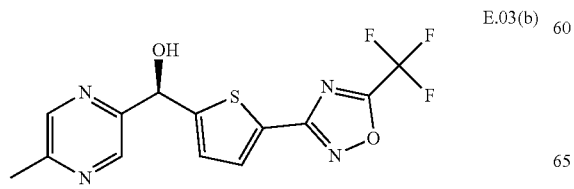

E.03(b)

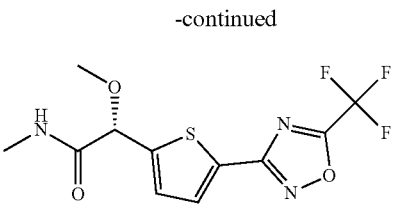

E.04(a)

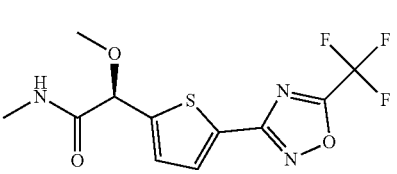

E.04(b)

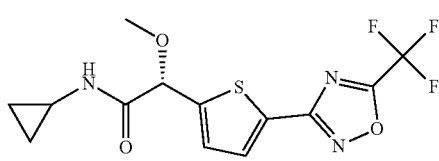

E.06(a)

-continued

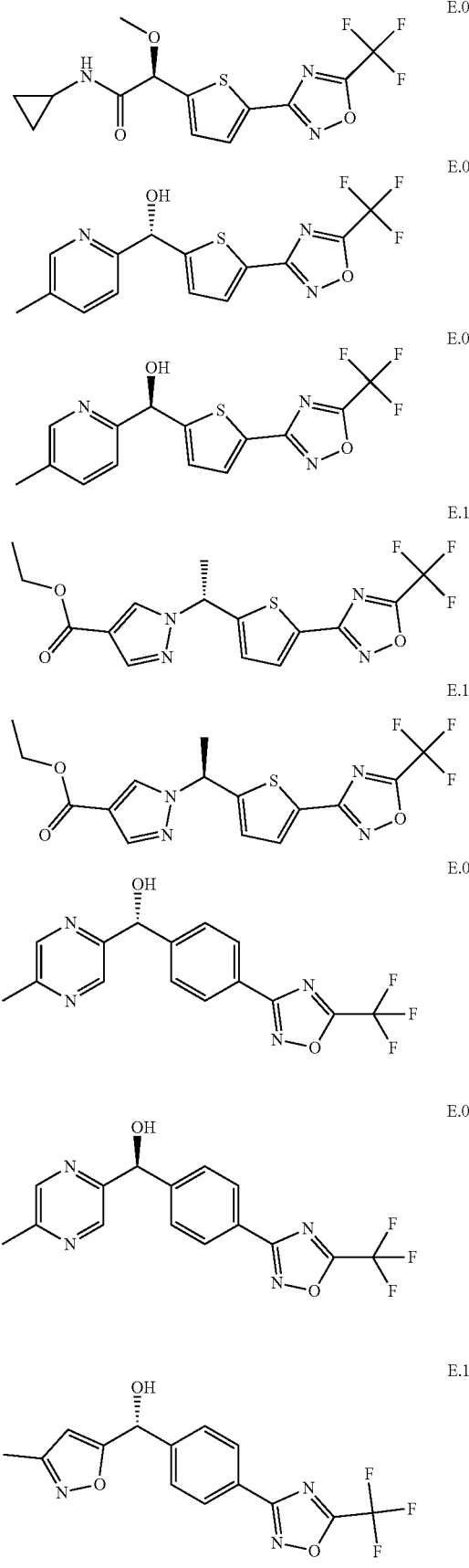

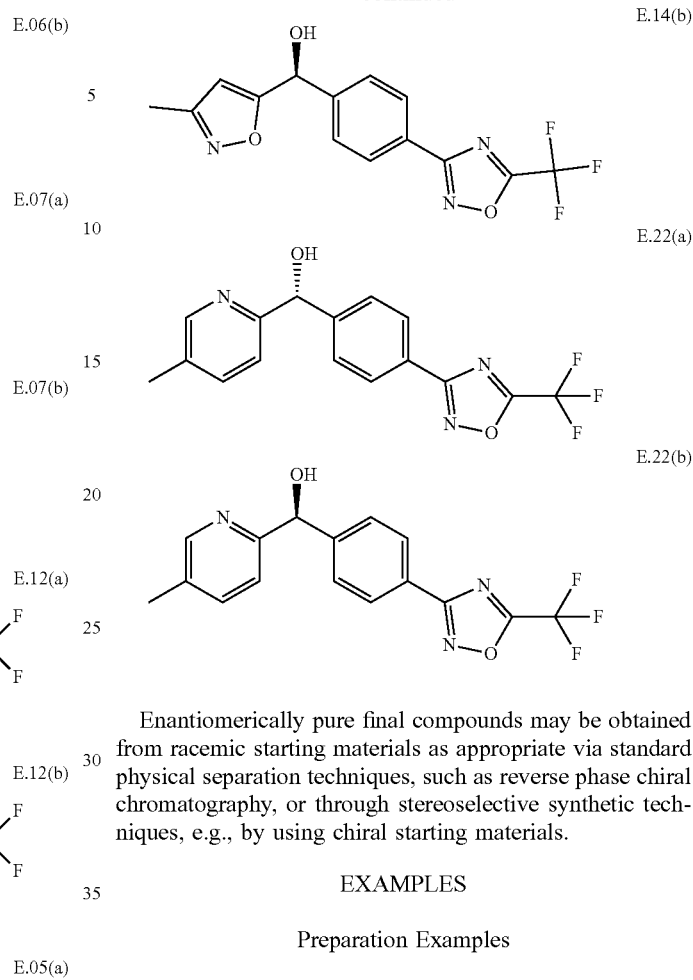

Enantiomerically pure final compounds may be obtained from racemic starting materials as appropriate via standard physical separation techniques, such as reverse phase chiral chromatography, or through stereoselective synthetic techniques, e.g., by using chiral starting materials.

EXAMPLES

Preparation Examples

The Examples which follow serve to illustrate the invention. The compounds of Formula (I) may be prepared according to the synthetic techniques described above.

The preparation of N-[[4-(N-hydroxycarbamimidoyl)phenyl]methyl]-N-methoxy-cyclopropanecarboxamide and N'-hydroxy-4-methyl-benzamidine are detailed in WO 2018/177894 and WO 2017/055473.

Example 1: This Example Illustrates the Preparation of N-methoxy-N-[[4-[5-(trifluoromethyl)-1,2,4-oxadiazol-3-yl]phenyl]methyl]cyclopropanecarboxamide

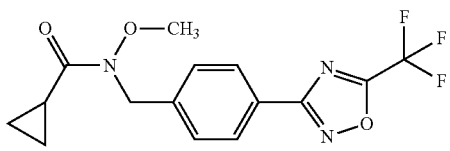 [SMILES: CON(Cc1ccc(-c2noc(C(F)(F)F)n2)cc1)C(=O)C1CC1]

To a 50 mL flask was added N-[[4-(N-hydroxycarbamimidoyl)phenyl]methyl]-N-methoxy-cyclopropanecarboxamide (89% purity, 0.20 g, 0.7 mmol) and tetrahydrofuran (2 mL) and 4 Å molecular sieves (150 mg). After cooling to 0° C., sodium tert-butoxide (0.1 g, 1 mmol) was introduced portionwise over 5 minutes. To the resultant suspension, ethyl 2,2,2-trifluoroacetate (0.58 g, 4.40 mmol) was added dropwise over 5 minutes and the ice bath was removed. After 2 hours, water (20 mL) and ethyl acetate (40 mL) were introduced and the contents were stirred for 10 minutes, the layers were separated, and the aqueous layer was extracted with ethyl acetate. The total combined organic layer was dried over sodium sulfate, filtered, and concentrated under reduced pressure to afford 0.18 g (60% yield, 82% purity) of the title compound as a brown amorphous solid.

$^{1}$H NMR (400 MHz, CDCl$_{3}$) δ ppm: 8.09 (d, 2H), 7.53 (d, 2H), 4.87 (s, 2H), 3.73 (s, 3H), 2.19 (m, 1H), 1.05 (m, 2H), 0.86 (m, 2H).

$^{19}$F NMR (400 MHz, CDCl$_{3}$) δ ppm: −65.33 (s).

Example 2: This Example Illustrates the Preparation of 3-(p-tolyl)-5-(trifluoromethyl)-1,2,4-oxadiazole

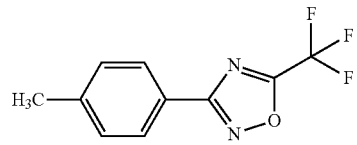 [SMILES: Cc1ccc(-c2noc(C(F)(F)F)n2)cc1]

To a 50 mL flask was added N'-hydroxy-4-methyl-benzamidine (96% purity, 1.0 g, 6.39 mmol), tetrahydrofuran (10 mL), 4 Å molecular sieves (150 mg). After cooling to 0° C., a 1M tetrahydrofuran solution of potassium tert-butoxide (6.39 mL, 6.39 mmol) was introduced dropwise. To the resultant suspension, ethyl 2,2,2-trifluoroacetate (0.58 g, 4.40 mmol) was added over 5 minutes and the ice bath was removed. After 1 hour, the reaction conversion was 92% complete with a reaction mixture having a pH of 10.3 (measured using a pH meter). Citric acid (50 g) was added portionwise, and the contents stirred for 10 minutes to achieve a pH 5.9 reaction mixture. The crude reaction contents were filtered over celite, washed twice with tetrahydrofuran (20 mL), and the filtrate was concentrated under reduced pressure. The resultant crude mass was diluted with dichloromethane (20 mL) and water (5 mL). The layers were separated and the aqueous layer was extracted twice with dichloromethane. The total combined organic layer was dried over sodium sulfate and concentrated under reduced pressure to afford 1.22 g of the title compound as a pale yellow liquid (80% yield, QNMR purity 96%).

$^{1}$H NMR (400 MHz, CDCl$_{3}$) δ ppm: 8.00 (d, 2H), 7.32 (d, 2H), 2.45 (s, 3H).

$^{19}$F NMR (400 MHz, CDCl$_{3}$) δ ppm: −65.41 (s).

The Table T1 below depicts additional variations of the conditions of reaction detailed in 3-(p-tolyl)-5-(trifluoromethyl)-1,2,4-oxadiazole.

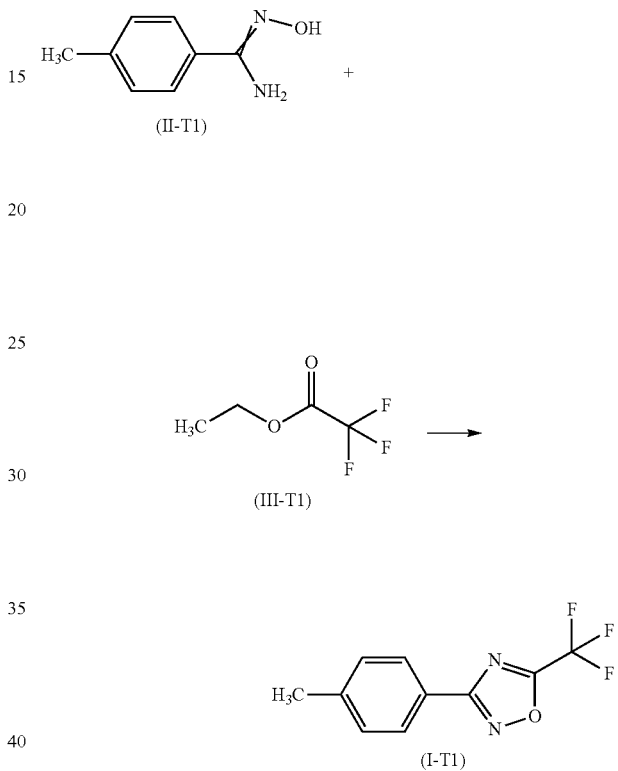

TABLE T1

| No. | III-T1 (eq) | Scale (gm) | Base/acid | Base/acid (eq) | Solvent (0.7M) | Time (h) | Temp. (° C.) | HPLC I-T1 conversion | Work-up acid | Yield I-T1 (%) | Purity (%) |
|---|---|---|---|---|---|---|---|---|---|---|---|
| 1 | 2 | 1 | KO$^t$Bu (1M THF) | 1 | THF | 2 | 24 | 93 | — | 68 | 95 |
| 2 | 2 | 1 | KO$^t$Bu (1M THF) | 1 | THF | 1 | 24 | 92 | citric acid | 80 | 96 |

The invention claimed is:

1. A process for the preparation of a compound of formula (I):

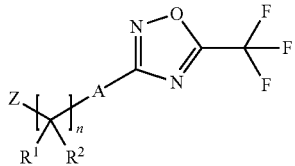
(I)

wherein
A is A-1

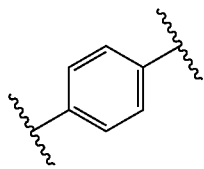
(A-1)

n is 1;
R$^1$ and R$^2$ are hydrogen
Z is Z$^1$ or Z$^2$:
Z$^1$ is hydrogen, halogen, cyano, —OH, or —SH;
Z$^2$ is —NR$^3$—C(=W)—X
W is O;
X is R$^5$;
R$^3$ is C$_{1-4}$alkyl, C$_{1-4}$haloalkyl, C$_{1-4}$alkoxy, C$_{1-4}$alkoxyC$_{1-4}$alkyl or C$_{3-8}$cycloalkyl;
R$^5$ is C$_{1-4}$alkyl, C$_{1-4}$haloalkyl, C$_{2-4}$alkenyl, C$_{2-6}$alkynyl, C$_{1-4}$alkoxy, C$_{1-4}$haloalkoxy, or C$_{1-4}$alkoxyC$_{1-4}$alkyl; or
R$^5$ is C$_{3-8}$cycloalkyl, or heterocyclyl; wherein said heterocyclyl moiety is a 4- to 6-membered non-aromatic ring which contains 1, 2 or 3 heteroatoms or groups individually selected from O, S, N, NR$^6$, C(=O) and S(=O)$_2$; and wherein any of said cycloalkyl, and heterocyclyl are unsubstituted or substituted by 1 or 2 substituents individually selected from R$^7$;
R$^6$ is hydrogen, C$_{1-4}$alkyl, C$_{1-4}$alkoxy, formyl, C$_{1-4}$alkylcarbonyl, C$_{1-4}$alkoxycarbonyl, N—C$_{1-4}$alkylaminocarbonyl, N,N-diC$_{1-4}$alkylaminocarbonyl, C$_{1-4}$alkylsulfonyl, N—C$_{1-4}$alkylaminosulfonyl, or N,N-diC$_{1-4}$alkylaminosulfonyl; and
R$^7$ is halogen;
said process comprising the step of reacting a compound of formula (II):

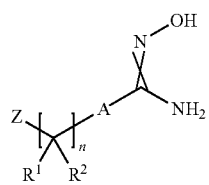
(II)

wherein A, n, R$^1$, R$^2$ and Z are as defined for the compound of formula (I), with a compound of formula (III):

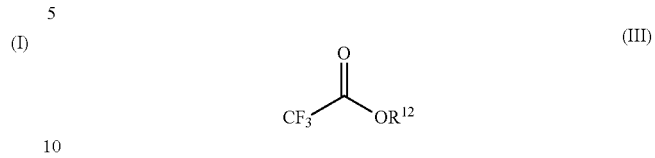
(III)

wherein R$^{12}$ is C$_{1-4}$alkyl,
wherein the process is carried out in the presence of at least one base;
wherein said base is selected from the group consisting of alkali metal C$_{1-6}$alkoxylates and alkaline earth metal C$_{1-6}$alkoxylates, and
said process further comprising the step of isolating the compound of formula (I) using an aqueous acidic medium.

2. The process according to claim 1, wherein the base is sodium tert-butoxide or potassium tert-butoxide.

3. The process according to claim 1, said process further comprising the step of reacting a compound of formula (VII):

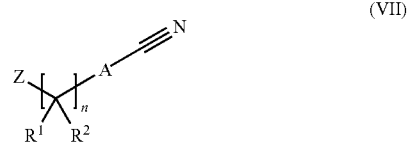
(VII)

wherein A, n, R$^1$, R$^2$ and Z are defined as in the compound of formula (I), with hydroxylamine or a salt thereof to obtain the compound of formula (II), wherein A, n, R$^1$, R$^2$ and Z are as defined for the compound of formula (I).

4. The process according to claim 1, said process further comprising the step of reacting an intermediate compound of Formula (I), wherein Z is Z$^1$, to obtain a compound of formula (I), wherein Z is Z$^2$.

5. The process according to claim 1, said process further comprising the step of reacting the compound of formula (I), wherein Z$^1$ is a halogen, with an amine of formula (V) or a salt thereof:

(V)

wherein R$^3$ is defined as in the compound of formula (I), to obtain a compound of formula (I-a) or a salt thereof:

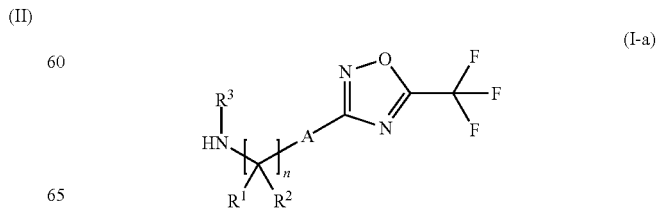
(I-a)

wherein A, n, $R^1$, $R^2$ and $R^3$ are defined as in the compound of formula (I).

6. The process according to claim 5, said process further comprising the step of reacting the compound of formula (I-a) or a salt thereof with a compound of formula (VI):

(VI)

wherein X and W are defined as in the compound of formula (I) and T is halogen, hydroxy or $C_{1-4}$alkoxy, to obtain a compound of formula (I-A):

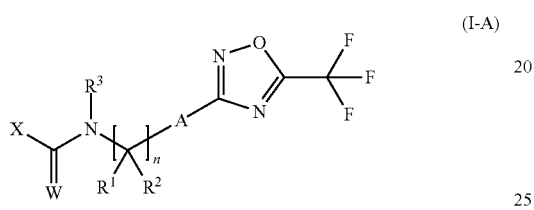

(I-A)

wherein A, n, $R^1$, $R^2$, $R^3$, X and W are defined as in the compound of formula (I).

7. The process according to claim 1, wherein the aqueous acidic medium comprises citric acid.

8. The process according to claim 1, wherein the aqueous acidic medium has a pH of from 2.0 to 6.0.

* * * * *